(12) United States Patent
Kirsch et al.

(10) Patent No.: US 6,372,731 B1
(45) Date of Patent: Apr. 16, 2002

(54) VITAMIN D DERIVATIVES WITH C-25 SUBSTITUENTS, PROCESS FOR THEIR PREPARATION, INTERMEDIATE PRODUCTS AND THEIR USE IN PREPARING MEDICAMENTS

(75) Inventors: Gerald Kirsch; Andreas Steinmeyer; Günter Neef; Katica Schwarz; Ruth Thieroff-Ekerdt; Herbert Wiesinger; Andreas Menrad; Martin Haberey, all of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 08/981,819
(22) PCT Filed: Apr. 30, 1996
(86) PCT No.: PCT/EP96/01788
 § 371 Date: Mar. 31, 1998
 § 102(e) Date: Mar. 31, 1998
(87) PCT Pub. No.: WO97/00242
 PCT Pub. Date: Jan. 3, 1997

(30) Foreign Application Priority Data

Jun. 14, 1995 (DE) .......................... 195 22 797

(51) Int. Cl.⁷ .................... A01N 45/00; C07C 401/00
(52) U.S. Cl. ...................... 514/167; 552/653
(58) Field of Search ............. 552/653; 514/167

(56) References Cited

U.S. PATENT DOCUMENTS 5,182,396 A * 1/1993 Tachinbana .............. 552/653

FOREIGN PATENT DOCUMENTS

WO    9407853    *    4/1994

* cited by examiner

*Primary Examiner*—Jose' G. Dees
*Assistant Examiner*—Alton Pryor
(74) *Attorney, Agent, or Firm*—Millen, White, Zelano & Branigan, P.C.

(57) ABSTRACT

A vitamin D derivative and its uses with substituents at C-25 of general formula I

6 Claims, 14 Drawing Sheets

VITAMIN D DERIVATIVES WITH C-25 SUBSTITUENTS, PROCESS FOR THEIR PREPARATION, INTERMEDIATE PRODUCTS AND THEIR USE IN PREPARING MEDICAMENTS

This application is a 371 of PCT/EP96/01788 filed Apr. 30, 1996.

This invention relates to vitamin D derivatives with substituents at C-25 of general formula I in which
- $Y_1$ means a hydrogen atom, a hydroxyl group, an alkanoyloxy group with 1 to 12 C atoms or an aroyloxy group,
- $Y_2$ means a hydrogen atom or an alkanoyl group with 1 to 12 C atoms or an aroyl group,
- $R_1$ and $R_2$ each mean a hydrogen atom or together an exocyclic methylene group,
- $R_3$ and $R_4$, independently of one another, mean a hydrogen atom, a chlorine or fluorine atom, an alkyl group with 1 to 4 carbon atoms, together a methylene group or together with quaternary carbon atom 20 a 3- to 7-membered, saturated or unsaturated carbocyclic ring,
- A and B together mean a keto group or A means a group OR' and B means a hydrogen atom or B means a group OR' and A means a hydrogen atom, whereby R' is a hydrogen atom or a straight-chain or branched-chain, saturated alkanoyl group with up to 9 carbon atoms or an aroyl group,
- $R_5$ and $R_6$ at the same time each mean a hydrogen atom, a chlorine or fluorine atom, a trifluoromethyl group, a straight-chain or branched-chain, saturated or unsaturated hydrocarbon radical with up to 4 carbon atoms or $R_5$ and $R_6$ together with carbon atom 25 mean a 3- to 7-membered, saturated or unsaturated carbocyclic ring and
- Z means a straight-chain or branched-chain, saturated or unsaturated hydrocarbon radical with up to 12 carbon atoms, which can also have a carbocyclic or heterocyclic partial structure and at any positions can exhibit keto groups, hydroxy groups (in α- or β-position) that in turn can be etherified or esterified, amino groups, halogen atoms or carboxylic acid ester or amide units and is linked by a carbonyl group, a hydroxymethylene group or an ethenediyl unit C—CH=CH—, E- or Z-geometry) with carbon atom 25, and processes for their production, intermediate products for these processes, pharmaceutical preparations that contain these compounds as well as their use for the production of pharmaceutical agents.

The alkanoyl or alkanoyloxy groups with 1 to 12 C atoms that are possible for radicals $Y_1$ and $Y_2$ are derived especially from saturated carboxylic acids. These radicals can be cyclic, acyclic, carbocyclic or heterocyclic. The preferred radicals are derived from $C_1$ to $C_9$, especially $C_2$ to $C_5$ alkanecarboxylic acids, such as, for example, acetyl(oxy), propionyl(oxy), butyryl(oxy).

As aroyl(oxy) groups, the benzoyl(oxy) groups and substituted benzoyl(oxy) groups are preferred.

For $R_3$ and $R_4$, the following preferred combinations apply: $R_3$=H, $R_4$=methyl or $R_3$=methyl, $R_4$=H; $R_3$=F, $R_4$=methyl or $R_3$=methyl, $R_4$=F; $R_3$, $R_4$=methyl; $R_3$ and $R_4$ together form a methylene group or together with tertiary carbon atom 20 form a cyclopropyl ring.

For A and B, the following preferred combinations apply: A=OH, B=H or A=H, B=OH and A and B form a carbonyl group.

For $R_5$ and $R_6$, the following preferred combinations apply:
$R_5$, $R_6$=methyl or ethyl; $R_5$ and $R_6$ together with carbon atom 25 form a cyclopropyl, cyclobutyl, cyclopentyl or cyclohexyl ring.

Especially preferred are the cases $R_5$, $R_6$=methyl, and $R_5$ and $R_6$ together with carbon atom 25 form a cyclopropyl ring.

For Z, the following preferences apply:
Z=—C(O)—$R_9$ or Z=—CH(OH)—$R_9$ (α- or β-hydroxy), whereby $R_9$ is a straight-chain or branched-chain, saturated or unsaturated hydrocarbon radical with up to 12 carbon atoms or else $R_9$ can be carbocyclic or heterocyclic or can exhibit such partial structures and can also be perfluorinated.

For $R_9$, the following special preferences apply:
$R_9$=methyl, ethyl, propyl, butyl, pentyl, hexyl, heptyl, i-propyl, i-butyl, t-butyl, 1-butenyl, 1-pentenyl, 1-butinyl, 1-pentinyl, phenyl, furanyl, pyridinyl, trifluoromethyl, perfluoroethyl, perfluoropropyl, perfluorobutyl, perfluoropentyl or perfluorohexyl.

Also, for Z, the following preference applies:

$$Z = \diagup\!\!\!\diagdown\!\!\!\diagup\!\!\!\overset{O}{\diagdown}\!\!R_{12},$$

with $R_{12}$=$C_1$–$C_{10}$ alkyl or alkoxy (straight-chain, branched, saturated, unsaturated, cyclic) or $$Z = \quad Z = \quad \text{———}\equiv\text{———}R_{13},$$

with $R_{13}$=$C_1$–$C_{10}$ alkyl (straight-chain, branched, saturated, unsaturated, cyclic), whereby $R_{13}$ can also have substituents (keto groups, hydroxy groups, carboxylic acid esters, carboxylic acid amides, halogens).

Especially preferred according to this invention are the following compounds:

(5Z,7E,22E)-(1S,3R,24R)-25-(1-Oxopentyl)-26,27-cyclo-9,10-secocholesta-5,7,10(19),22-tetraene-1,3,24-triol
(5Z,7E,22E)-(1S,3R,24S)-25-(1-oxopentyl)-26,27-cyclo-9,10-secocholesta-5,7,10(19),22-tetraene-1,3,24-triol
(5Z,7E,22E)-(1S,3R,24R)-25-acetyl-26,27-cyclo-9,10-secocholesta-5,7,10(19),22-tetraene-1,3,24-triol
(5Z,7E,22E)-(1S,3R,24S)-25-acetyl-26,27-cyclo-9,10-secocholesta-5,7,10(19),22-tetraene-1,3,24-triol (5Z,7E,22E)-(1S,3R,24R)-25-(1-oxopropyl)-26,27-cyclo-9,10-secocholesta-5,7,10(19),22-tetraene-1,3,24-triol
(5Z,7E,22E)-(1S,3R,24S)-25-(1-oxopropyl)-26,27-cyclo-9,10-secocholesta-5,7,10(19),22-tetraene-1,3,24-triol
(5Z,7E,22E)-(1S,3R,24R)-25-(1-oxobutyl)-26,27-cyclo-9,10-secocholesta-5,7,10(19),22-tetraene-1,3,24-triol
(5Z,7E,22E)-(1S,3R,24S)-25-(1-oxobutyl)-26,27-cyclo-9,10-secocholesta-5,7,10(19),22-tetraene-1,3,24-triol
(5Z,7E,22E)-(1S,3R,24R)-25-(1-oxohexyl)-26,27-cyclo-9,10-secocholesta-5,7,10(19),22-tetraene-1,3,24-triol
(5Z,7E,22E)-(1S,3R,24S)-25-(1-oxohexyl)-26,27-cyclo-9,10-secocholesta-5,7,10(19),22-tetraene-1,3,24-triol
(5Z,7E,22E)-(1S,3R,24R)-25-(1-oxoheptyl)-26,27-cyclo-9,10-secocholesta-5,7,10(19),22-tetraene-1,3,24-triol
(5Z,7E,22E)-(1S,3R,24S)-25-(1-oxoheptyl)-26,27-cyclo-9,10-secocholesta-5,7,10(19),22-tetraene-1,3,24-triol
(5Z,7E,22E)-(1S,3R,24R)-25-(1-oxooctyl)-26,27-cyclo-9,10-secocholesta-5,7,10(19),22-tetraene-1,3,24-triol
(5Z,7E,22E)-(1S,3R,24S)-25-(1-oxooctyl)-26,27-cyclo-9,10-secocholesta-5,7,10(19),22-tetraene-1,3,24-triol
(5Z,7E,22E)-(1S,3R,24R)-25-(1-oxononyl)-26,27-cyclo-9,10-secocholesta-5,7,10(19),22-tetraene-1,3,24-triol
(5Z,7E,22E)-(1S,3R,24S)-25-(1-oxononyl)-26,27-cyclo-9,10-secocholesta-5,7,10(19),22-tetraene-1,3,24-triol
(5Z,7E,22E)-(1S,3R,24R)-25-benzoyl-26,27-cyclo-9,10-secocholesta-5,7,10(19),22-tetraene-1,3,24-triol
(5Z,7E,22E)-(1S,3R,24S)-25-benzoyl-26,27-cyclo-9,10-secocholesta-5,7,10(19),22-tetraene-1,3,24-triol
(5Z,7E,22E)-(1S,3R,24R)-25-(2-furanylcarbonyl)-26,27-cyclo-9,10-secocholesta-5,7,10(19),22-tetraene-1,3,24-triol
(5Z,7E,22E)-(1S,3R,24S)-25-(2-furanylcarbonyl)-26,27-cyclo-9,10-secocholesta-5,7,10(19),22-tetraene-1,3,24-triol
(5Z,7E,22E)-(1S,3R,24R)-25-(2,2-dimethyl-1-oxopropyl)-26,27-cyclo-9,10-secocholesta-5,7,10(19),22-tetraene-1,3,24-triol
(5Z,7E,22E)-(1S,3R,24S)-25-(2,2-dimethyl-1-oxopropyl)-26,27-cyclo-9,10-secocholesta-5,7,10(19),22-tetraene-1,3,24-triol
(5Z,7E,22E)-(1S,3R,24R)-25-(2-pyridinylcarbonyl)-26,27-cyclo-9,10-secocholesta-5,7,10(19),22-tetraene-1,3,24-triol
(5Z,7E,22E)-(1S,3R,24S)-25-(2-pyridinylcarbonyl)-26,27-cyclo-9,10-secocholesta-5,7,10(19),22-tetraene-1,3,24-triol
[5Z,7E,22E,25(E)]-(1S,3R,24R)-25-(1-oxo-2-hexenyl)-26,27-cyclo-9,10-secocholesta-5,7,10(19),22-tetraene-1,3,24-triol
[5Z,7E,22E,25(E)]-(1S,3R,24S)-25-(1-oxo-2-hexenyl)-26,27-cyclo-9,10-secocholesta-5,7,10(19),22-tetraene-1,3,24-triol
(5Z,7E,22E)-(1S,3R,24R)-25-(1-oxo-2-hexenyl)-26,27-cyclo-9,10-secocholesta-5,7,10(19),22-tetraene-1,3,24-triol
(5Z,7E,22E)-(1S,3R,24S)-25-(1-oxo-2-hexinyl)-26,27-cyclo-9,10-secocholesta-5,7,10(19),22-tetraene-1,3,24-triol
(5Z,7E,22E)-(1S,3R,24R)-25-(cyclopropylcarbonyl)-26,27-cyclo-9,10-secocholesta-5,7,10(19),22-tetraene-1,3,24-triol
(5Z,7E,22E)-(1S,3R,24S)-25-(cyclopropylcarbonyl)-26,27-cyclo-9,10-secocholesta-5,7,10(19),22-tetraene-1,3,24-triol
[5Z,7E,22E,25(E)]-(1S,3R,24R)-25-(3-ethoxy-3-oxo-1-propenyl)-26,27-cyclo-9,10-secocholesta-5,7,10(19),22-tetraene-1,3,24-triol
[5Z,7E,22E,25(E)]-(1S,3R,24S)-25-(3-ethoxy-3-oxo-1-propenyl)-26,27-cyclo-9,10-secocholesta-5,7,10(19),22-tetraene-1,3,24-triol
[5Z,7E,22E,25(E)]-(1S,3R,24R)-25-[3-(1,1-dimethylethoxy)-3-oxo-1-propenyl]-26,27-cyclo-9,10-secocholesta-5,7,10(19),22-tetraene-1,3,24-triol
[5Z,7E,22E,25(E)]-(1S,3R,24S)-25-[3-(1,1-dimethylethoxy)-3-oxo-1-propenyl]-26,27-cyclo-9,10-secocholesta-5,7,10(19),22-tetraene-1,3,24-triol
[5Z,7E,22E,25(E)]-(1S,3R,24R)-25-(3-propoxy-3-oxo-1-propenyl)-26,27-cyclo-9,10-secocholesta-5,7,10(19),22-tetraene-1,3,24-triol
[5Z,7E,22E,25(E)]-(1S,3R,24S)-25-(3-propoxy-3-oxo-1-propenyl)-26,27-cyclo-9,10-secocholesta-5,7,10(19),22-tetraene-1,3,24-triol
[5Z,7E,22E,25(E)]-(1S,3R,24R)-25-(3-butoxy-3-oxo-1-propenyl)-26,27-cyclo-9,10-secocholesta-5,7,10(19),22-tetraene-1,3,24-triol
[5Z,7E,22E,25(E)]-(1S,3R,24S)-25-(3-butoxy-3-oxo-1-propenyl)-26,27-cyclo-9,10-secocholesta-5,7,10(19),22-tetraene-1,3,24-triol
(5Z,7E,22E)-[1S,3R,24S,25(S)]-25-(1-hydroxy-2,2,3,3,4,4,5,5,5-nonafluoropentyl)-26,27-cyclo-9,10-secocholesta-5,7,10(19),22-tetraene-1,3,24-triol
(5Z,7E,22E)-[1S,3R,24S,25(R)]-25-(1-hydroxy-2,2,3,3,4,4,5,5,5-nonafluoropentyl)-26,27-cyclo-9,10-secocholesta-5,7,10(19),22-tetraene-1,3,24-triol
(5Z,7E,22E)-[1S,3R,24R,25(S)]-25-(1-hydroxy-2,2,3,3,4,4,5,5,5-nonafluoropentyl)-26,27-cyclo-9,10-secocholesta-5,7,10(19),22-tetraene-1,3,24-triol
(5Z,7E,22E)-[1S,3R,24R,25(R)]-25-(1-hydroxy-2,2,3,3,4,4,5,5,5-nonafluoropentyl)-26,27-cyclo-9,10-secocholesta-5,7,10(19),22-tetraene-1,3,24-triol
(5Z,7E,22E)-[1S,3R,24S,25(S)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol
(5Z,7E,22E)-[1S,3R,24S,25(R)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol
(5Z,7E,22E)-[1S,3R,24R,25(S)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol
(5Z,7E,22E)-[1S,3R,24R,25(R)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol
(5Z,7E,22E)-(1S,3R,24R)-25-(trifluoroacetyl)-26,27-cyclo-9,10-secocholesta-5,7,10(19),22-tetraene-1,3,24-triol
(5Z,7E,22E)-(1S,3R,24S)-25-(trifluoroacetyl)-26,27-cyclo-9,10-secocholesta-5,7,10(19),22-tetraene-1,3,24-triol
(5Z,7E,22E)-(1S,3R,24R)-25-(perfluoroethylcarbonyl)-26,27-cyclo-9,10-secocholesta-5,7,10(19),22-tetraene-1,3,24-triol
(5Z,7E,22E)-(1S,3R,24S)-25-(perfluoroethylcarbonyl)-26,27-cyclo-9,10-secocholesta-5,7,10(19),22-tetraene-1,3,24-triol
(5Z,7E,22E)-(1S,3R,24R)-25-(perfluoropropylcarbonyl)-26,27-cyclo-9,10-secocholesta-5,7,10(19),22-tetraene-1,3,24-triol
(5Z,7E,22E)-(1S,3R,24S)-25-(perfluoropropylcarbonyl)-26,27-cyclo-9,10-secocholesta-5,7,10(19),22-tetraene-1,3,24-triol
(5Z,7E,22E)-(1S,3R,24R)-25-(perfluorobutylcarbonyl)-26,27-cyclo-9,10-secocholesta-5,7,10(19),22-tetraene-1,3,24-triol
(5Z,7E,22E)-(1S,3R,24S)-25-(perfluorobutylcarbonyl)-26,27-cyclo-9,10-secocholesta-5,7,10(19),22-tetraene-1,3,24-triol (5Z,7E,22E)-(1S,3R,24R)-25-(perfluoropentylcarbonyl)-26,27-cyclo-9,10-secocholesta-5,7,10(19),22-tetraene-1,3,24-triol (5Z,7E,22E)-(1S,3R,24S)-25-(perfluoropentylcarbonyl)-26,27-cyclo-9,10-secocholesta-5,7,10(19),22-tetraene-1,3,24-triol (5Z,7E,22E)-(1S,3R,24R)-25-(perfluorohexylcarbonyl)-26,27-cyclo-9,10-secocholesta-5,7,10(19),22-tetraene-1,3,24-triol (5Z,7E,22E)-(1S,3R,24S)-25-(perfluorohexylcarbonyl)-26,27-cyclo-9,10-secocholesta-5,7,10(19),22-tetraene-1,3,24-triol (5Z,7E,22E)-(1S,3R,24R)-25-acetyl-20-methyl-26,27-cyclo-9,10-secocholesta-5,7,10(19),22-tetraene-1,3,24-triol (5Z,7E,22E)-(1S,3R,24S)-25-acetyl-20-methyl-26,27-cyclo-9,10-secocholesta-5,7,10(19),22-tetraene-1,3,24-triol (5Z,7E,22E)-(1S,3R,24R)-20-methyl-25-(1-oxopropyl)-26,27-cyclo-9,10-secocholesta-5,7,10(19),22-tetraene-1,3,24-triol (5Z,7E,22E)-(1S,3R,24S)-20-methyl-25-(1-oxopropyl)-26,27-cyclo-9,10-secocholesta-5,7,10(19),22-tetraene-1,3,24-triol (5Z,7E,22E)-(1S,3R,24R)-20-methyl-25-(1-oxobutyl)-26,27-cyclo-9,10-secocholesta-5,7,10(19),22-tetraene-1,3,24-triol (5Z,7E,22E)-(1S,3R,24S)-20-methyl-25-(1-oxobutyl)-26,27-cyclo-9,10-secocholesta-5,7,10(19),22-tetraene-1,3,24-triol (5Z,7E,22E)-(1S,3R,24R)-20-methyl-25-(1-oxopentyl)-26,27-cyclo-9,10-secocholesta-5,7,10(19),22-tetraene-1,3,24-triol (5Z,7E,22E)-(1S,3R,24S)-20-methyl-25-(1-oxopentyl)-26,27-cyclo-9,10-secocholesta-5,7,10(19),22-tetraene-1,3,24-triol (5Z,7E,22E)-(1S,3R,24R)-20-methyl-25-(1-oxohexyl)-26,27-cyclo-9,10-secocholesta-5,7,10(19),22-tetraene-1,3,24-triol (5Z,7E,22E)-(1S,3R,24S)-20-methyl-25-(1-oxohexyl)-26,27-cyclo-9,10-secocholesta-5,7,10(19),22-tetraene-1,3,24-triol (5Z,7E,22E)-(1S,3R,24R)-20-methyl-25-(1-oxoheptyl)-26,27-cyclo-9,10-secocholesta-5,7,10(19),22-tetraene-1,3,24-triol (5Z,7E,22E)-(1S,3R,24S)-20-methyl-25-(1-oxoheptyl)-26,27-cyclo-9,10-secocholesta-5,7,10(19),22-tetraene-1,3,24-triol (5Z,7E,22E)-(1S,3R,24R)-20-methyl-25-(1-oxooctyl)-26,27-cyclo-9,10-secocholesta-5,7,10(19),22-tetraene-1,3,24-triol (5Z,7E,22E)-(1S,3R,24S)-20-methyl-25-(1-oxooctyl)-26,27-cyclo-9,10-secocholesta-5,7,10(19),22-tetraene-1,3,24-triol (5Z,7E,22E)-(1S,3R,24R)-20-methyl-25-(1-oxononyl)-26,27-cyclo-9,10-secocholesta-5,7,10(19),22-tetraene-1,3,24-triol (5Z,7E,22E)-(1S,3R,24S)-20-methyl-25-(1-oxononyl)-26,27-cyclo-9,10-secocholesta-5,7,10(19),22-tetraene-1,3,24-triol (7E,22E)-(1R,3R,24R)-25-acetyl-26,27-cyclo-19-nor-9,10-secocholesta-5,7,22-triene-1,3,24-triol (7E,22E)-(1R,3R,24S)-25-acetyl-26,27-cyclo-19-nor-9,10-secocholesta-5,7,22-triene-1,3,24-triol (7E,22E)-(1R,3R,24R)-25-(1-oxopropyl)-26,27-cyclo-19-nor-9,10-secocholesta-5,7,22-triene-1,3,24-triol (7E,22E)-(1R,3R,24S)-25-(1-oxopropyl)-26,27-cyclo-19-nor-9,10-secocholesta-5,7,22-triene-1,3,24-triol (7E,22E)-(1R,3R,24R)-25-(1-oxobutyl)-26,27-cyclo-19-nor-9,10-secocholesta-5,7,22-triene-1,3,24-triol (7E,22E)-(1R,3R,24S)-25-(1-oxobutyl)-26,27-cyclo-19-nor-9,10-secocholesta-5,7,22-triene-1,3,24-triol (7E,22E)-(1R,3R,24R)-25-(1-oxopentyl)-26,27-cyclo-19-nor-9,10-secocholesta-5,7,22-triene-1,3,24-triol (7E,22E)-(1R,3R,24S)-25-(1-oxopentyl)-26,27-cyclo-19-nor-9,10-secocholesta-5,7,22-triene-1,3,24-triol (7E,22E)-(1R,3R,24R)-25-(1-oxohexyl)-26,27-cyclo-19-nor-9,10-secocholesta-5,7,22-triene-1,3,24-triol (7E,22E)-(1R,3R,24S)-25-(1-oxohexyl)-26,27-cyclo-19-nor-9,10-secocholesta-5,7,22-triene-1,3,24-triol (7E,22E)-(1R,3R,24R)-25-(1-oxoheptyl)-26,27-cyclo-19-nor-9,10-secocholesta-5,7,22-triene-1,3,24-triol (7E,22E)-(1R,3R,24S)-25-(1-oxoheptyl)-26,27-cyclo-19-nor-9,10-secocholesta-5,7,22-triene-1,3,24-triol (7E,22E)-(1R,3R,24R)-25-(1-oxooctyl)-26,27-cyclo-19-nor-9,10-secocholesta-5,7,22-triene-1,3,24-triol (7E,22E)-(1R,3R,24S)-25-(1-oxooctyl)-26,27-cyclo-19-nor-9,10-secocholesta-5,7,22-triene-1,3,24-triol (7E,22E)-(1R,3R,24R)-25-(1-oxononyl)-26,27-cyclo-19-nor-9,10-secocholesta-5,7,22-triene-1,3,24-triol (7E,22E)-(1R,3R,24S)-25-(1-oxononyl)-26,27-cyclo-19-nor-9,10-secocholesta-5,7,22-triene-1,3,24-triol (7E,22E)-(1R,3R,24R)-25-acetyl-20-methyl-26,27-cyclo-19-nor-9,10-secocholesta-5,7,22-triene-1,3,24-triol (7E,22E)-(1R,3R,24S)-25-acetyl-20-methyl-26,27-cyclo-19-nor-9,10-secocholesta-5,7,22-triene-1,3,24-triol (7E,22E)-(1R,3R,24R)-20-methyl-25-(1-oxopropyl)-26,27-cyclo-19-nor-9,10-secocholesta-5,7,22-triene-1,3,24-triol (7E,22E)-(1R,3R,24S)-20-methyl-25-(1-oxopropyl)-26,27-cyclo-19-nor-9,10-secocholesta-5,7,22-triene-1,3,24-triol (7E,22E)-(1R,3R,24R)-20-methyl-25-(1-oxobutyl)-26,27-cyclo-19-nor-9,10-secocholesta-5,7,22-triene-1,3,24-triol (7E,22E)-(1R,3R,24S)-20-methyl-25-(1-oxobutyl)-26,27-cyclo-19-nor-9,10-secocholesta-5,7,22-triene-1,3,24-triol (7E,22E)-(1R,3R,24R)-20-methyl-25-(1-oxopentyl)-26,27-cyclo-19-nor-9,10-secocholesta-5,7,22-triene-1,3,24-triol (7E,22E)-(1R,3R,24S)-20-methyl-25-(1-oxopentyl)-26,27-cyclo-19-nor-9,10-secocholesta-5,7,22-triene-1,3,24-triol (7E,22E)-(1R,3R,24R)-20-methyl-25-(1-oxohexyl)-26,27-cyclo-19-nor-9,10-secocholesta-5,7,22-triene-1,3,24-triol (7E,22E)-(1R,3R,24S)-20-methyl-25-(1-oxohexyl)-26,27-cyclo-19-nor-9,10-secocholesta-5,7,22-triene-1,3,24-triol (7E,22E)-(1R,3R,24R)-20-methyl-25-(1-oxoheptyl)-26,27-cyclo-19-nor-9,10-secocholesta-5,7,22-triene-1,3,24-triol (7E,22E)-(1R,3R,24S)-20-methyl-25-(1-oxoheptyl)-26,27-cyclo-19-nor-9,10-secocholesta-5,7,22-triene-1,3,24-triol (7E,22E)-(1R,3R,24R)-20-methyl-25-(1-oxooctyl)-26,27-cyclo-19-nor-9,10-secocholesta-5,7,22-triene-1,3,24-triol (7E,22E)-(1R,3R,24S)-20-methyl-25-(1-oxooctyl)-26,27-cyclo-19-nor-9,10-secocholesta-5,7,22-triene-1,3,24-triol (7E,22E)-(1R,3R,24R)-20-methyl-25-(1-oxononyl)-26,27-cyclo-19-nor-9,10-secocholesta-5,7,22-triene-1,3,24-triol (7E,22E)-(1R,3R,24S)-20-methyl-25-(1-oxononyl)-26,27-cyclo-19-nor-9,10-secocholesta-5,7,22-triene-1,3,24-triol (5Z,7E,22E)-(1S,3R,25(R)]-1,3-dihydroxy-25-(1-hydroxy-2,2,3,3,4,4,5,5,5-nonafluoropentyl)-26,27-cyclo-9,10-secocholesta-5,7,10(19),22-tetraen-24-one (5Z,7E,22E)-(1S,3R,25(S)]-1,3-dihydroxy-25-(1-hydroxy-2,2,3,3,4,4,5,5,5-nonafluoropentyl)-26,27-cyclo-9,10-secocholesta-5,7,10(19),22-tetraen-24-one (5Z,7E,22E)-[1S,3R,25(R)]-1,3-dihydroxy-25-(1-hydroxy-2,2,3,3,4,4,5,5,6,6,7,7,7-tridecafluoroheptyl)-26,27-cyclo-9,10-secocholesta-5,7,10(19),22-tetraen-24-one (5Z,7E,22E)-[1S,3R,25(S)]-1,3-dihydroxy-25-(1-hydroxy-2,2,3,3,4,4,5,5,6,6,7,7,7-tridecafluoroheptyl)-26,27-cyclo-9,10-secocholesta-5,7,10(19),22-tetraen-24-one (5Z,7E,22E)-(3S,24R)-25-acetyl-26,27-cyclo-9,10-secocholesta-5,7,10(19),22-tetraene-3,24-diol
(5Z,7E,22E)-(3S,24S)-25-acetyl-26,27-cyclo-9,10-secocholesta-5,7,10(19),22-tetraene-3,24-diol
(5Z,7E,22E)-(3S,24R)-25-(1-oxopropyl)-26,27-cyclo-9,10-secocholesta-5,7,10(19),22-tetraene-3,24-diol
(5Z,7E,22E)-(3S,24S)-25-(1-oxopropyl)-26,27-cyclo-9,10-secocholesta-5,7,10(19),22-tetraene-3,24-diol
(5Z,7E,22E)-(3S,24R)-25-(1-oxobutyl)-26,27-cyclo-9,10-secocholesta-5,7,10(19),22-tetraene-3,24-diol
(5Z,7E,22E)-(3S,24S)-25-(1-oxobutyl)-26,27-cyclo-9,10-secocholesta-5,7,10(19),22-tetraene-3,24-diol
(5Z,7E,22E)-(3S,24R)-25-(1-oxopentyl)-26,27-cyclo-9,10-secocholesta-5,7,10(19),22-tetraene-3,24-diol
(5Z,7E,22E)-(3S,24S)-25-(1-oxopentyl)-26,27-cyclo-9,10-secocholesta-5,7,10(19),22-tetraene-3,24-diol
(5Z,7E,22E)-(3S,24R)-25-(1-oxohexyl)-26,27-cyclo-9,10-secocholesta-5,7,10(19),22-tetraene-3,24-diol
(5Z,7E,22E)-(3S,24S)-25-(1-oxohexyl)-26,27-cyclo-9,10-secocholesta-5,7,10(19),22-tetraene-3,24-diol
(5Z,7E,22E)-(3S,24R)-25-(1-oxoheptyl)-26,27-cyclo-9,10-secocholesta-5,7,10(19),22-tetraene-3,24-diol
(5Z,7E,22E)-(3S,24S)-25-(1-oxoheptyl)-26,27-cyclo-9,10-secocholesta-5,7,10(19),22-tetraene-3,24-diol
(5Z,7E,22E)-(3S,24R)-25-(1-oxooctyl)-26,27-cyclo-9,10-secocholesta-5,7,10(19),22-tetraene-3,24-diol
(5Z,7E,22E)-(3S,24S)-25-(1-oxooctyl)-26,27-cyclo-9,10-secocholesta-5,7,10(19),22-tetraene-3,24-diol
(5Z,7E,22E)-(3S,24R)-25-(1-oxononyl)-26,27-cyclo-9,10-secocholesta-5,7,10(19),22-tetraene-3,24-diol
(5Z,7E,22E)-(3S,24S)-25-(1-oxononyl)-26,27-cyclo-9,10-secocholesta-5,7,10(19),22-tetraene-3,24-diol
[5Z,7E,22E,25(E)]-(1S,3R,24R)-25-[3-(1,1-dimethylethoxy)-3-oxo-1-propenyl]-24-methoxy-26,27-cyclo-9,10-secocholesta-5,7,10(19),22-tetraene-1,3diol
[5Z,7E,22E,25(E)]-(1S,3R,24S)-25-[3-(1,1-dimethylethoxy)-3-oxo-1-propenyl]-24-methoxy-26,27-cyclo-9,10-secocholesta-5,7,10(19),22-tetraene-1,3diol
(5Z,7E,22E)-(1S,3R,24R)-25-hydroxymethyl-26,27-cyclo-9,10-secocholesta-5,7,10(19),22-tetraene-1,3,24-triol
(5Z,7E,22E)-(1S,3R,24S)-25-hydroxymethyl-26,27-cyclo-9,10-secocholesta-5,7,10(19),22-tetraene-1,3,24-triol
[5Z,7E,22E,25(E)]-(1S,3R,24R)-25-(3-oxo-1-heptenyl)-26,27-cyclo-9,10-secocholesta-5,7,10(19),22-tetraene-1,3,24-triol
[5Z,7E,22E,25(E)]-(1S,3R,24S)-25-(3-oxo-1-heptenyl)-26,27-cyclo-9,10-secocholesta-5,7,10(19),22-tetraene-1,3,24-triol
[5Z,7E,22E,25(E,E)]-(1S,3R,24R)-25-(1-oxo-2,4-hexadienyl)-26,27-cyclo-9,10-secocholesta-5,7,10(19),22-tetraene-1,3,24-triol
[5Z,7E,22E,25(E,E)]-(1S,3R,24S)-25-(1-oxo-2,4-hexadienyl)-26,27-cyclo-9,10-secocholesta-5,7,10(19),22-tetraene-1,3,24-triol The natural vitamins $D_2$ and $D_3$ (cf. general formula of vitamin D) are inherently biologically inactive and are converted into biologically active metabolites [1α,25-dihydroxy vitamin $D_3$ (calcitriol) or -$D_2$] only after hydroxylation at C-atom 25 in the liver and at C-atom 1 in the kidney. The action of the active metabolites involves the regulation of the calcium and phosphate concentration in the serum; they counteract a dropping of the calcium concentration in the serum by increasing the calcium absorption in the intestine and under certain circumstances promoting calcium mobilization from the bones.

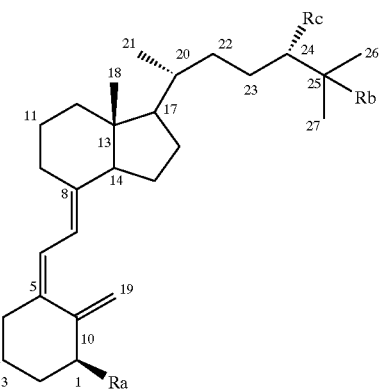

Ergocalciferol: Ra = Rb = H, Rc = $CH_3$ vitamin $D_2$
Double bond C-22/23

Cholecalciferol: Ra = Rb = Rc = H vitamin $D_3$
25-hydroxycholecalciferol: Ra = Rc = H, Rb = OH
1α-hydroxycholecalciferol: Ra = OH, Rb = Rc = H
1α, 25-dihydroxycholecalciferol: Ra = Rb = OH, Rc = H Calcitriol In addition to their pronounced effect on the calcium and phosphate metabolism, the active metabolites of vitamins $D_2$ and $D_3$ and their synthetic derivatives have a proliferation-inhibiting and differentiation-stimulating action on tumor cells and normal cells, such as, for example, skin cells. In addition, a pronounced effect on cells of the immune system (inhibiting of proliferation and interleukin 2-synthesis of lymphocytes, increase of cytotoxicity and phagocytosis in vitro of monocytes) has been found, which manifests itself in an immunomodulatory action, and finally, because of a stimulating action on bone-forming cells, an increased formation of bone in normal and osteoporotic rats is found [R. Bouillon et al. "Short Term Course of 1,25(OH)$_2$D$_3$ Stimulates Osteoblasts But Not Osteoclasts." Calc. Tissue Int. 49, 168–173 (1991)].

All actions are mediated by bonding to the vitamin D receptor. Because of the bonding, the activity of specific genes is regulated.

When using biologically active metabolites of vitamins $D_2$ and $D_3$, a toxic effect on the calcium metabolism is produced (hypercalcemia).

By structural manipulations of the side chain, therapeutically usable effectiveness can be separated from undesirable hypercalcemic activity. A suitable structural variation is the introduction of 24-hydroxy derivatives.

1α-Cholecalciferols that are hydroxylated in 24-position are already described in DE 25 26 981. They have a lower toxicity than the corresponding non-hydroxylated 1α-cholecalciferol. Further, 24-hydroxy derivatives are described in the following patent applications: DE 39 33 034, DE 40 03 854, DE 40 34 730, EP 0 421 561, EP 0 441 467, WO 91/12238.

Finally, 25-carboxylic acid derivatives of calcitriol that are hydroxylated at C-24 are described in WO 94/07853, which exhibit a more advantageous spectrum of action than calcitriol. While the ability to trigger a hypercalcemia is considerably weakened, the proliferation-inhibiting and differentiation-stimulating actions are maintained.

Relative to these structurally allied compounds, the substances according to the invention are distinguished in that they show a greater effect on cell differentiation, whereby the effect on the calcium balance does not increase.

The vitamin D activity of the substances according to the invention is determined with the aid of the calcitriol-receptor test. It is carried out with use of a specific receptor protein from the intestines of juvenile pigs.

Receptor-containing binding protein is incubated in a test tube with $^3$H-calcitriol ($5 \times 10^{-10}$ mol/l) in a reaction volume of 0.270 ml in the absence and in the presence of test substances for two hours at 4° C. To separate free and receptor-bound calcitriol, a charcoal-dextran absorption is carried out. 250 µl of a charcoal-dextran suspension is fed to each test tube and incubated at 4° C. for 20 minutes. Then, the samples are centrifuged at 10,000×g for 5 minutes at 4° C. The supernatant is decanted and measured in a β-counter after 1 hour of equilibration in Picofluor 15™.

The competition curves that are obtained with various concentrations of test substance as well as of reference substance (unlabeled calcitriol) at constant concentration of the reference substance ($^3$H-calcitriol) are placed in relation to one another and a competition factor (KF) is determined.

It is defined as a quotient of the concentrations of the respective test substance and the reference substance, which are necessary for 50% competition:

KF=Concentration of test substance at 50% competition/ Concentration of reference substance at 50% competition It is common to the compounds according to the invention that they all have a considerable affinity to the calcitriol receptor.

To determine the acute hypercalcemic action of various calcitriol derivatives, the test that is described below is carried out:

The action of control (solution base), reference substance (1,25(OH)$_2$-D$_3$=calcitriol) and test substance is tested in each case after one-time subcutaneous administration in groups of 10 healthy male rats (140–170 g). During the testing time, the rats are kept in special cages to determine the excretion of water and mineral substances. Urine is collected in 2 fractions (0–16 hours and 16–22 hours). An oral dose of calcium (0.1 mmol of calcium in 6.5% alpha-hydroxypropylcellulose, 5 ml/animal) replaces at 1600 hours the calcium intake that is lacking by food deprivation. At the end of the test, the animals are killed by decapitation and exsanguinated to determine the serum-calcium values. For the primary screen test in vivo, an individual standard dose (200 µg/kg) is tested. For selected substances, the result is supported by establishing a dose-effect relation.

A hypercalcemic action is shown in serum-calcium level values that are higher than in the control.

The significance of differences between substance groups and controls and between test substance and reference substance are supported with suitable statistical processes. The result is indicated as dose ratio DR (DR=factor of test substance dose/reference substance dose for comparable effects).

The differentiation-stimulating action of calcitriol analogues is also detected quantitatively.

It is known in the literature (Mangelsdorf, D. J. et al., J. Cell. Biol. 98: 391–398 (1984)), that the treatment of human leukemia cells (promyelocyte cell line HL 60) in vitro with calcitriol induces the differentiation of cells to macrophages.

HL 60 cells are cultivated in tissue culture medium (RPMI 10% fetal calf serum) at 37° C. in an atmosphere of 5% CO$_2$ in air.

For substance testing, the cells are centrifuged off, and $2.0 \times 10^5$ cells/ml in phenol red-free tissue culture medium is taken up. The test substances are dissolved in ethanol and diluted with tissue culture medium without phenol red to the desired concentration. The dilution stages are mixed with the cell suspension at a ratio of 1:10, and 100 µl each of this cell suspension that is mixed with substance is pipetted into an indentation of a 96-hole plate. For control, a cell suspension is mixed analogously with the solvent.

After incubation for 96 hours at 37° C. in 5% CO$_2$ in air, 100 µl of an NBT-TPA solution (nitro blue tetrazolium (NBT), final concentration in the batch of 1 mg/ml, tetradecanoyl phorbolmyristate-13-acetate (TPA), final concentration in the batch of $2 \times 10^{-7}$ mol/l) is pipetted into each indentation of the 96-hole plate in the cell suspension.

By incubation for 2 hours at 37° C. and 5% CO$_2$ in air, NBT is reduced to insoluble formazan because of the intracellular oxygen radical release, stimulated by TPA, in the cells that are differentiated to macrophages.

To complete the reaction, the indentations of the 96-hole plate are suctioned off, and the cells are affixed to the bottom of the plate by adding methanol and dried after affixing. To dissolve the intracellular formazan crystals that are formed, 100 µl of potassium hydroxide (2 mol/l) and 100 µl of dimethyl sulfoxide are pipetted into each indentation and ultrasonically treated for 1 minute. The concentration of formazan is measured by spectrophotometry at 650 nm.

As a yardstick for the differentiation induction of HL 60 cells to macrophages, the concentration of formed formazan applies. The result is indicated as a dose ratio (DR=factor of test substance dose/reference substance dose for comparable semi-maximum effects).

The results of the calcitriol-receptor test and the determination of the dose ratio of the differentiation induction of HL 60 cells and the dose ratio for hypercalcemia are summarized below (Tab. 1):

Selected Test Compounds (5Z,7E,22E)-(1S,3R,24R)-25-Acetyl-26,27-cyclo-9,10-secocholesta-5,7,10(19),22-tetraene-1,3,24-triol 7b (5Z,7E,22E)-(1S,3R,24R)-25-(1-oxobutyl)-26,27-cyclo-9,10-secocholesta-5,7,10(19),22-tetraene-1,3,24-triol 8b (5Z,7E,22E)-(1S,3R,24R)-25-benzoyl-26,27-cyclo-9,10-secocholesta-5,7,10(19),22-tetraene-1,3,24-triol 10b (5Z,7E,22E)-(1S,3R,24R)-25-(cyclopropylcarbonyl)-26,27-cyclo-9,10-secocholesta-5,7,10(19),22-tetraene-1,3,24-triol 12b (5Z,7E,22E)-(1S,3R,24R)-25-(2,2-dimethyl-1-oxopropyl)-26,27-cyclo-9,10-secocholesta-5,7,10(19),22-tetraene-1,3,24-triol 15b (5Z,7E,22E)-(1S,3R,24R)-25-(1-oxo-2-hexinyl)-26,27-cyclo-9,10-secocholesta-5,7,10(19),22-tetraene-1,3,24-triol 19b (5Z,7E,22E)-(1S,3R,24S)-25-acetyl-20-methyl-26,27-cyclo-9,10-secocholesta-5,7,10(19),22-tetraene-1,3,24-triol 33a (5Z,7E,22E)-(1S,3R,24R)-25-acetyl-20-methyl-26,27-cyclo-9,10-secocholesta-5,7,10(19),22-tetraene-1,3,24-triol 33b (5Z,7E,22E)-(1S,3R,24S)-20-methyl-25-(1-oxobutyl)-26,27-cyclo-9,10-secocholesta-5,7,10(19),22-tetraene-1,3,24-triol 35a (5Z,7E,22E)-(1S,3R,24R)-20-methyl-25-(1-oxobutyl)-26,27-cyclo-9,10-secocholesta-5,7,10(19),22-tetraene-1,3,24-triol 35b (7E,22E)-(1R,3R,24R)-25-acetyl-26,27-cyclo-19-nor-9,10-secocholesta-5,7,22-triene-1,3,24-triol 55b (7E,22E)-(1R,3R,24S)-25-acetyl-20-methyl-26,27-cyclo-19-nor-9,10-secocholesta-5,7,22-triene-1,3,24-triol 81a (7E,22E)-(1R,3R,24R)-25-acetyl-20-methyl-26,27-cyclo-19-nor-9,10-secocholesta-5,7,22-triene-1,3,24-triol 81b Comparison Compound
Calcitriol

TABLE 1

| Compound | Competition Factor KF for Receptor Bonding | Dose Ratio for Differentiation Induction in HL 60 Cells |
| --- | --- | --- |
| 7b | 1 | 0.5 |
| 8b | 2 | 0.9 |
| 10b | 2 | 6 |
| 12b | 2 | 0.2 |
| 15b | 6 | 1.1 |
| 19b | 2 | 1.5 |
| 33a | 4 | 0.5 |
| 33b | 4 | 0.4 |
| 35a | 7 | 0.3 |
| 35b | 2 | 0.2 |
| 55b | 4.5 | 0.2 |
| 81a | 10 | 0.2 |
| 81b | 3 | 0.1 |
| Calcitriol | 1 | 1 |

In addition to an affinity to the vitamin D receptor, which is comparable to that of calcitriol, the compounds listed partially show a greater cell-differentiating activity.

The induction of a hypercalcemia is carried out, however, only at very much higher doses than in the case of calcitriol (e.g., dose ratio for 7b=300, 8b=100, 15b=300, 19b>300, calcitriol DR=1).

By the reduced property of triggering a hypercalcemia, the substances according to the invention are suitable in a special way for the production of pharmaceutical agents for the treatment of diseases that are characterized by hyperproliferation and deficient cell differentiation. Included in these are, for example, hyperproliferative diseases of the skin (psoriasis, pityriasis subia pilasis, acne, ichthyosis) as well as tumor diseases and precancerous stages (for example, tumors of the intestines, carcinomas of the breast, lung tumors, prostate carcinomas, leukemias, T-cell lymphomas, melanomas, Batazell Larzin, squamous carcinoma, actinic keratoses, cervix dysplasias, metastasizing tumors of any type).

Also, for the treatment and prophylaxis of diseases that are characterized by a disequilibrium of the immune system, the substances according to the invention are suitable. These include eczemas and diseases of the atopic Formon series, as well as auto-immune diseases, such as, for example, multiple scleroses, diabetes mellitus type I, myasthenia gravis, lupus erythematosus, scleroderma, bullous skin diseases (pemphigus, pemphigoid), further rejection reactions in the case of autologous, allogeneic or xenogeneic transplants, as well as AIDS. In all these diseases, the new compounds of general formula I can be combined advantageously with other substances that have an immunosuppressive action, such as cyclosporin A, FK 506, rapamycin and anti-CD 4 antibodies.

The substances are also suitable for therapy of secondary hyperparathyroidism and renal osteodystrophia because of the property of calcitriols to drop the parathormone synthesis.

Owing to the presence of the vitamin D conceptor in the insulin-producing cells of the pancreas, the substances are suitable by increasing the insulin secretion for the therapy of diabetes mellitus type II.

Further, it has been found, surprisingly enough, that by topical application of the compounds according to the invention on the skin of mice, rats and guinea pigs, an increased reddening of the skin and increase of the thickness of the epidermis can be induced. The increase in the reddening of the skin is determined from the increase in the red value of the skin surface that can be quantified with a calorimeter. The red value is typically increased 1.5-fold after the substance (dose 0.003%) is administered three times at intervals of 24 hours. The increase of the thickness of the epidermis is quantified in the histological preparation. It is typically increased 2.5-fold. The number of proliferating epidermal cells (cells in the S-phase of the cell cycle) is determined by flow cytometry and is typically increased by a factor of 6.

These properties of the 25-carboxylic acid derivatives in the vitamin D series according to the invention can appear suitable for therapeutic use in the case of atrophic skin, as it occurs in natural skin aging because of increased light exposure or medicinally-induced skin atrophy by treatment with glucocorticoids.

Further, it can be assumed that wound healing can be accelerated by topical application with the new compounds.

In cell populations of the hair follicle, which contribute decisively to hair growth or to hair cycle regulation, it was possible to detect vitamin $D_3$ receptor proteins (Stumpf, W. E. et al., Cell Tissue Res. 238: 489–496; Milde, P. et al., J. Invest., 97: 230–239, 1991). In addition, in vitro findings on isolated hair follicle keratinocytes show a proliferation-inhibiting and differentiation-stimulating influence of 1,25-$(OH)_2$-$D_3$.

From clinical observations, it is known that the vitamin $D_3$-resistant rickets often accompanies alopecia, which develops in early infancy. Experimental findings show that the vitamin $D_3$ bonding site of the VDR in this disease mutates, i.e., is defective (Kristjansson, K. et al., J. Clin. Invest. 92: 12–16, 1993). Keratinocytes, which were isolated from the hair follicles of these patients, do not react in vitro to the addition of 1,25-$(OH)_2$-$D_3$ (Arase, S. et al., J. Dermatol. Science 2: 353–360, 1991).

These findings indicate a decisive role for 1,25 D3 in the regulation of hair growth.

These analogues are therefore especially suitable for the production of pharmaceutical agents for the treatment of diseases which accompany disrupted hair growth (androgenetic alopecia, alopecia areata/totalis, chemotherapy-induced alopecia) or for supporting physiological hair growth.

Senile and postmenopausal osteoporosis is characterized by an increased bone turnover with an overall negative balance. Owing to the bone shrinkage especially of trabecular bones, fractures result to an increased extent. Owing to the stimulating action of calcitriol, both in the number and the conduct of synthesis of cells forming new bones (osteoblasts), the substances according to the invention are suitable for therapy and prophylaxis of senile and postmenopausal osteoporosis (EP 0 634 173 A1), of steroid-induced osteoporosis as well as for accelerated healing of arthroplasties. For the therapy of various forms of osteoporosis, they can be combined advantageously with estradiol or other derivatives of estrogen.

Finally, it was possible to show that calcitriol increases the synthesis of a growth substance for nerve cells (nerve growth factor) [M. S. Saporito et al. Brain Res. 633, 189–196 (1994)]. The compounds according to the invention are therefore also suitable for treating degenerative diseases of the peripheral and central nervous system, such as Alzheimer's disease and amyotrophic lateral sclerosis.

In addition, it has been found that certain compounds of general formula I in HL 60 cells antagonize, surprisingly enough, the action of calcitriol. In the series of 25-alkyl derivatives, the compounds with increasing chain length on the carbonyl group in the case of constantly good receptor affinity show considerably weaker differentiation-stimulating agonistic activity in HL 60 cells (Tab. 2).

Selected Test Compounds with Antagonistic Action (5Z,7E,22E)-(1S,3R,24R)-25-(1-Oxopentyl)-26,27-cyclo-9,10-secocholesta-5,7,10(19),22-tetraene-1,3,24-triol 6b (5Z,7E,22E)-(1S,3R,24R)-25-(1-oxohexyl)-26,27-cyclo-9,10-secocholesta-5,7,10(19),22-tetraene-1,3,24-triol 9b

[5Z,7E,22E,25(E)]-(1S,3R,24R)-25-(1-oxo-2-hexenyl)-26,27-cyclo-9,10-secocholesta-5,7,10(19),22-tetraene-1,3,24-triol 18b

[5Z,7E,22E,25(E)]-(1S,3R,24R)-25-(3-ethoxy-3-oxo-1-propenyl)-26,27-cyclo-9,10-secocholesta-5,7,10(19),22-tetraene-1,3,24-triol 24b

[5Z,7E,22E,25(E)]-(1S,3R,24R)-25-[3-(1,1-dimethylethoxy)-3-oxo-1-propenyl]-26,27-cyclo-9,10-secocholesta-5,7,10(19),22-tetraene-1,3,24-triol 26b (5Z,7E,22E)-(1S,3R,24S)-20-methyl-25-(1-oxooctyl)-26,27-cyclo-9,10-secocholesta-5,7,10(19),22-tetraene-1,3,24-triol 43a (5Z,7E,22E)-(1S,3R,24R)-20-methyl-25-(1-oxooctyl)-26,27-cyclo-9,10-secocholesta-5,7,10(19),22-tetraene-1,3,24-triol 43b (7E,22E)-(1R,3R,24R)-25-(1-oxopentyl)-26,27-cyclo-19-nor-9,10-secocholesta-5,7,22-triene-1,3,24-triol 58b (7E,22E)-(1R,3R,24R)-25-(1-oxohexyl)-26,27-cyclo-19-nor-9,10-secocholesta-5,7,22-triene-1,3,24-triol 61b (7E,22E)-(1R,3R,24S)-25-(1-oxoheptyl)-26,27-cyclo-19-nor-9,10-secocholesta-5,7,22-triene-1,3,24-triol 64a (7E,22E)-(1R,3R,24R)-20-methyl-25-(1-oxohexyl)-26,27-cyclo-19-nor-9,10-secocholesta-5,7,22-triene-1,3,24-triol 61b Comparison Compound
Calcitriol

TABLE 2

| Compound | Competition Factor KF for Receptor Bonding | Dose Ratio for Differentiation Induction in HL 60 Cells |
| --- | --- | --- |
| 6b | 2 | 0.5 |
| 6b | 2 | 58 |
| 9b | 3 | >180 |
| 18b | 2 | 330 |
| 24b | 4 | >1000 |
| 26b | 4 | >1000 |
| 43a | 48 | >1000 |
| 43b | 33 | >1000 |
| 58b | 3 | 160 |
| 61b | 3 | >1000 |
| 64a | 3.5 | 120 |
| 87b | 3 | 116 |
| Calcitriol | 1 | 1 |

The compounds 6b, 9b, 18b, 24b, 26b, 43a, 43b, 58b, 61b, 64a and 87b antagonize the action of calcitriol in HL 60 cells. This property is continued with increasing chain length in radical Z of general formula I.

Such compounds that antagonize the action of calcitriol can be used for the therapy of hypercalcemias, such as, for example, in hypervitaminosis D or intoxication with calcitriol and calcitriol-like active substances, or in the case of increased extrarenal calcitriol synthesis in granulomatous diseases (sarcoidosis, tuberculosis). Also, paraneoplastic hypercalcemias (for example, in osteolytic metastases and tumors with increased synthesis of parathormone-related peptides) as well as in hypercalcemias in hyperparathyroidism.

In addition, calcitriol antagonists can be used for birth control. In the reproductive tracts of female and male animals, the vitamin D receptor is expressed. It is known that the female and male fertility of vitamin-D-deficient animals is reduced. By short-term substitution of calcitriol, the reproductive output can be increased. Calcitriol antagonists are therefore able to influence female and male fertility.

Since calcitriol, under certain conditions, shows an immunosuppressive action, calcitriol receptor antagonists can also be used as immunostimulants, e.g., in the case of weak defenses against infections.

Calcitriol is known to be able to modulate hair growth. Calcitriol antagonists can therefore be used therapeutically in the case of undesirable hair growth, e.g., in hirsutism.

Vitamin D has long been known to play a stimulating role in the formation of arteriosclerotic plaque. In such vascular lesions, a calcitriol-regulated protein, osteopontin, is found to be increased, to which a role in vascular sclerosis is attributed [R. Eisenstein et al. Arch. Path. 77, 27–35 (1964), L. A. Fitzpatrick et al., J. Clin. Invest. 94, 1597–1604 (1994)]. Calcitriol antagonists are therefore suitable for therapy and prophylaxis of all types of arteriosclerosis.

Finally, calcitriol antagonists are suitable because of the property of calcitriol to increase unspecific immune reactions of monocytic cells, for therapy of inflammatory diseases, especially of a chronic nature, such as rheumatoid arthritis, Crohn's disease, ulcerative colitis, and granulomatous diseases such as sarcoidosis and other foreign-body reactions.

This invention thus relates to pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For topical use, the compounds are advantageously formulated as creams or ointments or in a similar form of pharmaceutical agent that is suitable for topical use. Each such formulation can also contain other pharmaceutically compatible and nontoxic adjuvants, such as, e.g., stabilizers, antioxidants, binders, dyes, emulsifiers or flavoring additives. The compounds are advantageously administered by injection or intravenous infusion of suitable sterile solutions or as oral dosage via the alimentary tract or topically in the form of creams, ointments, lotions or suitable transdermal patches, as is described in EP-A 0 387 077.

The daily dose is approximately 0.1 μg/patient/day—1000 μg (1 mg)/patient/day, preferably 1.0 μg/patient/day–500 μg/patient/day.

The production of the vitamin D derivatives of general formula I is carried out according to the invention from a compound of general formula II,

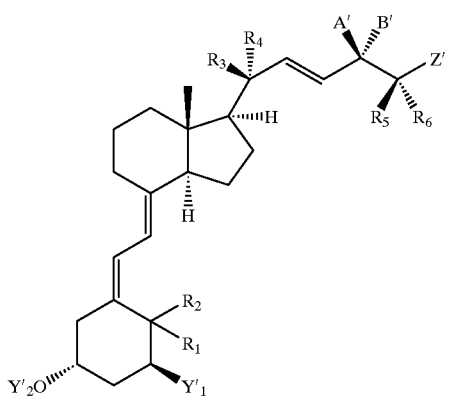

II in which Y'$_1$ means a hydrogen atom or a protected hydroxy group and Y'$_2$ means a hydroxy protective group.

The protective groups are preferably alkyl-, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or truisopropylsilyl (TIPS) groups or another standard hydroxy protective group (see T. W. Greene, P. G. M. Wuts "Protective Groups in Organic Synthesis," $2^{nd}$ Edition, John Wiley & Sons, 1991).

A' and B' together can mean a keto group or one of the two substituents can mean an optionally protected hydroxy group and the other a hydrogen atom (e.g., silyl protective group of the above definition, tetrahydrofuranyl, tetrahydropyranyl, methoxymethyl, methoxyethoxymethyl or trimethylsilylethoxymethyl group).

Z' can have a meaning analogous to Z or optionally exhibit protective group-carrying substituents (e.g., hydroxy protective groups according to the above definition).

By simultaneous or successive cleavage of the hydroxy protective groups and optionally by partial, successive or complete esterification of the free hydroxy groups, II is converted to a compound of general formula I.

In the case of the silyl protective groups or the trimethylsilylethoxymethyl group, tetrabutylammonium fluoride, hydrofluoric acid or hydrofluoric acid/pyridine is used for their cleavage; in the case of the other ether groups, the latter are cleaved under catalytic action of acid, for example, p-toluenesulfonic acid, pyridinium-p-toluenesulfonate, acetic acid, hydrochloric acid, phosphoric acid or an acidic ion exchanger.

The esterification of the free hydroxy groups can be carried out according to standard processes with the corresponding carboxylic acid chlorides, bromides or anhydrides.

Separations of diastereomers (e.g., relative to C-24) can be carried out in the final stage or any other preliminary stage.

The production of the starting compounds for general formula II starts from various starting compounds depending on the ultimately desired substitution pattern in 10- and 20-position.

For the production of compounds of general formula II, in which R$_1$ and R$_2$ together mean an exocyclic methylene group, a start is made from known aldehyde III [M. Calverley Tetrahedron 43, 4609 (1987), WO 87/00834].

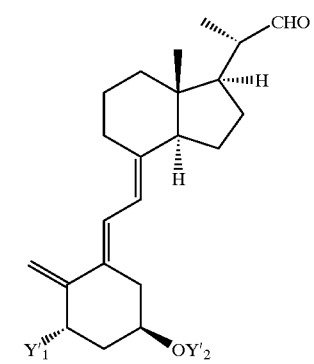

III

For Y'$_1$ and Y'$_2$, the already mentioned definitions apply. Protective groups other than those mentioned in the bibliographic references can be obtained by analogous procedure using correspondingly modified silyl chlorides (e.g., tert-butyldiphenylsilyl chloride instead of tert-butyldimethylsilyl chloride). By foregoing the corresponding stages for 1α-hydroxylation, derivatives of Y'$_1$=H type can be obtained.

The compounds of general formula III are now converted, analogously to known processes, into aldehydes of general formula IV (WO 94/07853).

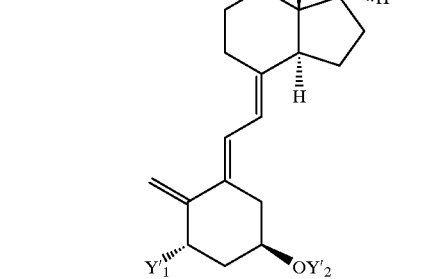

IV

For R3 and R$_4$, the definitions that are already mentioned above apply.

In building the side chain, both compounds of general formula III and compounds of general formula IV can now be used. By way of example, the reaction of compounds of general formula III is described below. Analogously to the established sequence (WO 94/07853), carboxylic acid amides of general formula V can thus be generated,

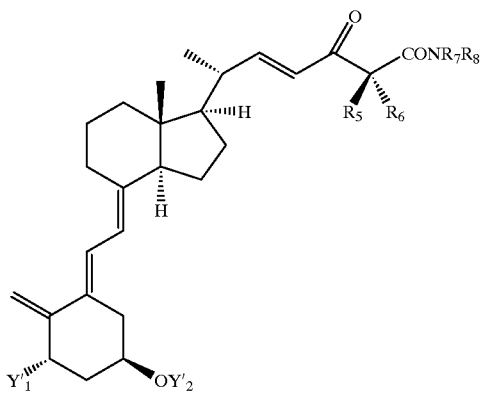

V

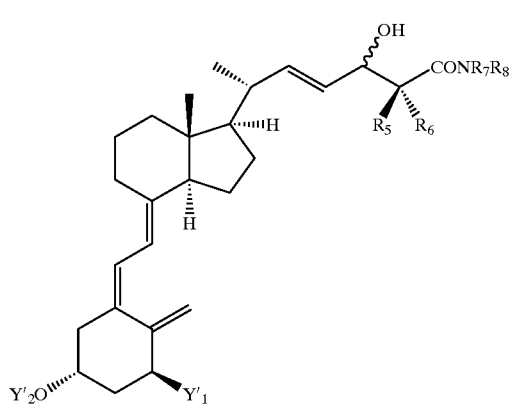

VII whereby for $Y'_1$, $Y'_2$, $R_5$ and $R_6$, the already given definitions apply. Preferably, $R_5$ and $R_6$ each are to mean a methyl group or both together with carbon atom 25 mean a cyclopropyl ring. $R_7$ and $R_8$ mean straight-chain or branched-chain alkyl groups with 1–9 carbon atoms, whereby especially methyl and ethyl groups are preferred.

Reduction of the keto group with reducing agents, such as, e.g., $NaBH_4$ or $NaBH_4/CeCl_3$, then results in alcohols of general formula VI.

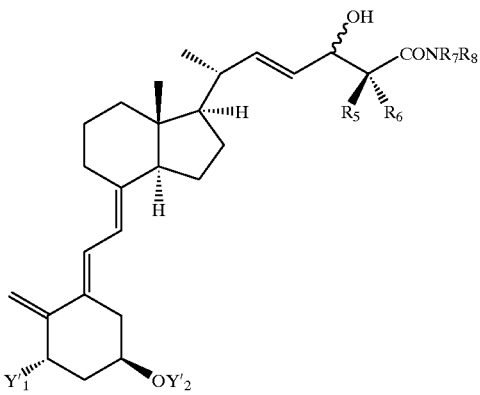

VI

To establish the natural vitamin D-triene system, a photochemical isomerization of the compounds of general formula VI is performed. Irradiation with ultraviolet light is carried out in the presence of a so-called triplet sensitizer. Within the scope of this invention, anthracene is used in this respect. By cleavage of the π-bond of the 5,6-double bond, rotation of the A ring by 180° around the 5,6-single bond and reestablishing the 5,6-double bond, the stereoisomerism on the 5,6-double bond is reversed, whereby compounds of general formula VII result, whereby $Y'_1$, $Y'_2$, $R_5$, $R_6$, $R_7$ and $R_8$ have the above-mentioned meanings. The diastereomeric alcohols at C-24 can be separated by chromatography.

In building radical Z', compounds of general formula VII are reacted at low temperature (−100 to 0° C.) with suitable lithium organyls of general formula VIII $$LiR_9 \qquad \text{VIII}$$

The lithium organyls can be generated under standard conditions (halogen-lithium exchange in the case of haloalkanes, metalizations of aromatic or heteroaromatic systems, metal-lithium exchange, definitions for $R_9$ were already mentioned). In this case, compounds of general formula II result, whereby for $Y'_1$, $Y'_2$, $R_5$ and $R_6$, the above-mentioned meanings apply; $R_1$ and R2 together mean an exocyclic methylene group; R3 and $R_4$ depending on the selection of aldehyde III or IV have the meanings derived from them; A' is a hydroxy group and B' is a hydrogen atom or A' is a hydrogen atom and B' is a hydroxy group, and Z'=C(O)—$R_9$. The hydroxyl group in 24-position (A' or B') can be converted before the final protective group cleavage optionally with an oxidizing agent such as, e.g., PCC, PDC, $BaMnO_4$, $MnO_2$, Swern conditions, Dess-Martin reagent to a 24-ketone of general formula II, whereby A' and B' together form a keto group. The subsequent protective group cleavage must then be carried out, however, under acidic reaction conditions (e.g., acidic ion exchanger, acetic acid, p-toluenesulfonic acid, pyridinium-p-toluenesulfonate), since when using the usual fluoride reagents, conjugated additions of nucleophiles to the enone system are to be feared. A temporary protection of the 24-hydroxy group can be carried out with a protective group as in $Y'_1$ and $Y'_2$ to increase in some cases the yield in the addition of lithium-organic compound VIII.

If sterically exacting, branched radicals are to be established for $R_9$, the reaction of the known ester of general formula IX (WO 94/07853) instead of amide VII is carried out with lithium-organic compound VIII, whereby a compound of general formula II results.

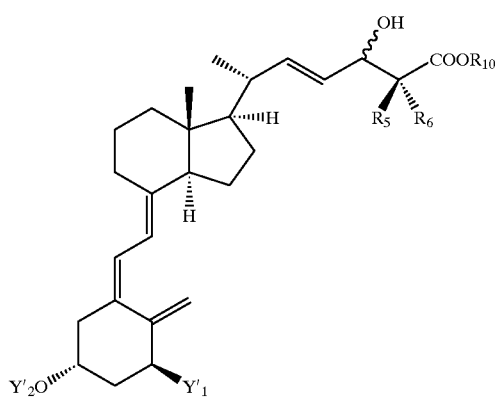

IX

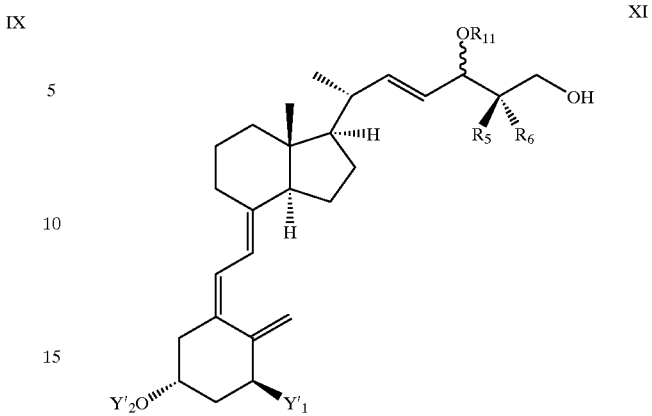

XI are obtained.

Radical $R_{10}$ means a straight-chain or branched-chain alkyl group with 1–9 carbon atoms.

In principle, the diastereomeric alcohols (relative to C-24) in the case of the above-mentioned sequences can be reacted separated in advance and reacted separately.

For the synthesis of additional modified derivatives, the compound of general formula IX is converted by protection of the 24-hydroxy group into a compound of general formula X, Under the known reaction conditions, ethers, sulfides and amines can now be generated, whereby compounds of general formula II result, for which $Z'=X—R_9$, with $X=O$, S, NH, N-alkyl, N-acyl.

For further structural variation, the compounds of general formula XI can be reacted to the aldehydes of general formula XII.

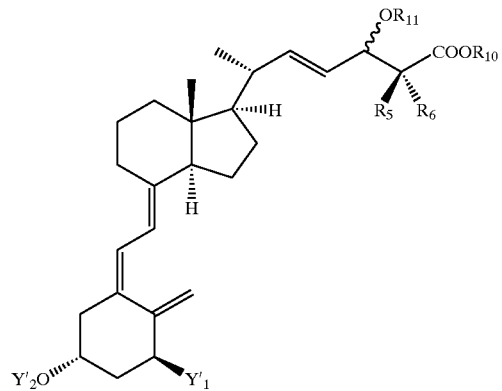

X

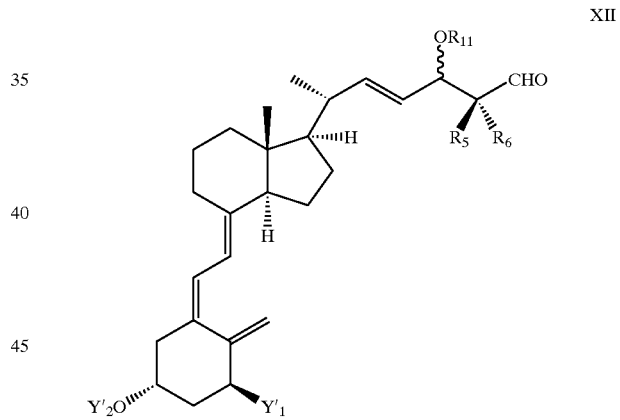

XII whereby $R_{11}$ means an acid-labile protective group that has a definition analogous to $Y'_1$ or $Y'_2$ or the tetrahydropyranyl, tetrahydrofuranyl, ethoxyethyl, methoxymethyl or methoxyethoxymethyl group. By reduction of the ester unit of general formula X with a reducing agent such as, e.g., DIBAH, TIBA, LiAlH$_4$, RedAl, compounds of general formula XI This reaction can be carried out with the reagents or methods already indicated for the oxidation of the hydroxy group in 24-position. In addition to the already mentioned lithium organyls of general formula VIII, whose use here results in compounds of general formula II, whereby $Z'=CH(OH)—R_9$, perfluorinated alkyl radicals can be introduced here according to methods known in the literature [G. K. Surya Prakash J. Org. Chem. 56, 984 (1991), H. Uno et al. Bull. Chem. Soc. Jpn. 62, 2636 (1989)]. By catalytic action of tetrabutylammonium fluoride on the readily available perfluoroalkyltrimethylsilanes (synthesis from the commercially available perfluoroalkyl iodides) or by iodine-lithium exchange of the perfluoroalkyl iodides with methyllithium/lithium bromide complex, an attack on the carbonyl group can be carried out, whereby after hydrolytic working-up, compounds of general formula XIII result,

XIII

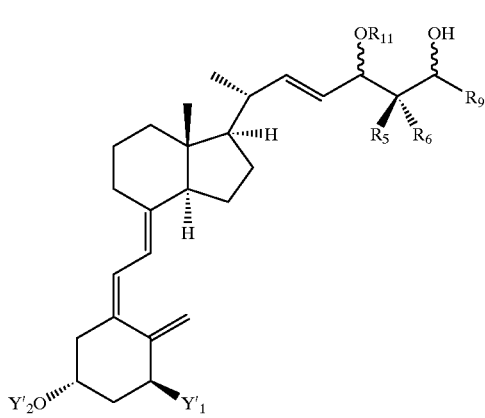

whereby R$_9$ can mean straight-chain or branched-chain perfluorinated alkyl radicals that have 1–9 carbon atoms. The diastereomeric alcohols are separated by chromatography. The compounds of general formula XIII, on the one hand, can be considered a special case of general formula II and can be further treated as described there or, on the other hand, can be converted by oxidation with one of the already previously mentioned oxidizing agents (preferably Swern conditions or Dess-Martin reagent) into a compound of general formula II, whereby Z'=C(O)—R$_9$.

Aldehyde XII can also be reacted with Wittig, Wittig-Horner or Wadsworth-Emmons reagents of type XIV

XIV

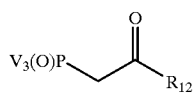

whereby V=C1–C8 alkyl or alkoxy (straight-chain or branched-chain or cyclic) preferably mean methyl, methoxy, ethyl, ethoxy, butyl, butoxy, phenyl, phenoxy and the definition for R$_{12}$ was already given above, in the presence of bases (e.g., NaH, KH, LDA, butyllithium, LiHMDS, NaHMDS, KHMDS), to compounds of general formula XV,

XV

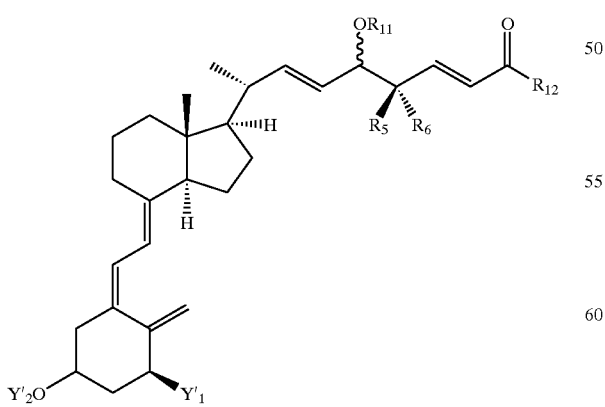

which can be considered a special case of general formula II, for which:

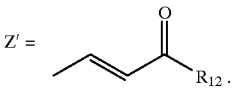

The aldehyde of general formula XII can also be converted by using methods known in the literature [L. Van Hijfte Tetrahedron Lett. 30, 3655 (1989), S. L. Schreiber J. Am. Chem. Soc. 112, 5583 (1990), J. R. Hauske Tetrahedron Lett. 33, 3715 (1992)] into compounds of general formula XVI,

XVI

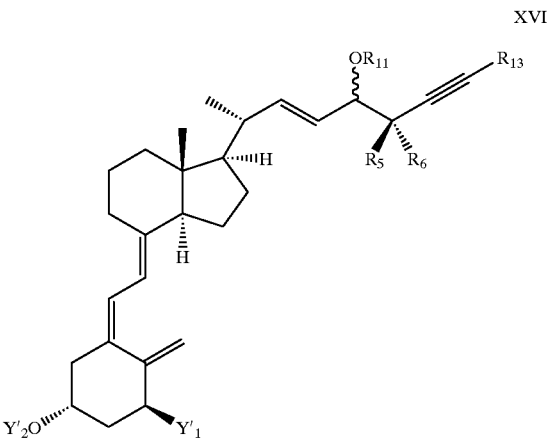

which can be considered a special case of general formula II, whereby $$Z' = \text{———}\equiv\text{———} R_{13}.$$

The production of compounds of general formula I, if R$_1$ and R$_2$ mean hydrogen atoms, is carried out in that a compound of general formula II',

II'

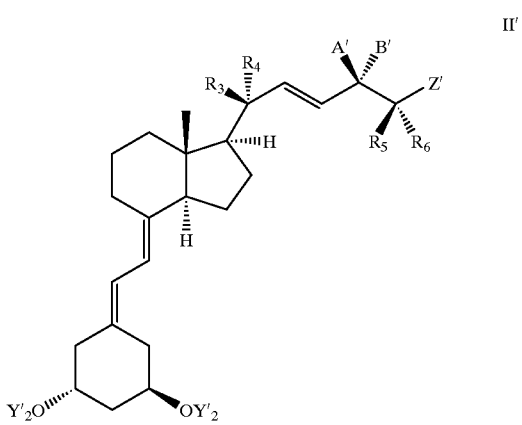

whereby the already mentioned meanings exist for Y'$_2$, R$_3$, R$_4$, R$_5$, R$_6$, A', B' and Z', is treated analogously to the conditions that are described for the reaction of II.

The production of compounds of general formula II' is carried out in a convergent synthesis method, whereby CD and A-ring fragments are separately structured. For synthesis of the CD fragments, aldehyde XVII, known in the literature [H. H. Inhoffen et al. Chem. Ber. 91, 780 (1958), Chem. Ber. 92, 1772 (1959), W. G. Dauben 30, 677 (1989)] is used,

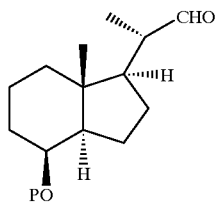
XVII in which P means an acyl-, alkyl- or aryl-substituted silyl or tetrahydropyranyl, tetrahydrofuranyl, methoxymethyl, ethoxyethyl group, an acyl group (e.g., acetyl, benzoyl) or another alcohol protective group (see T. W. Greene, P. G. M. Wuts "Protective Groups in Organic Synthesis," $2^{nd}$ Edition, John Wiley & Sons, Inc., 1991).

According to the known process (WO 94/07853), the modifications at C-20 that are already described for the normal series can be introduced, whereby a compound of general formula XVIII results.

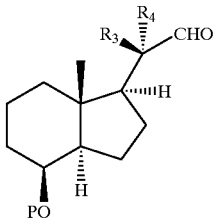
XVIII

For $R_3$ and $R_4$, the above-mentioned definitions apply.

For simplification and by way of example, the reaction of the compound of general formula XVII is described below.

If $R_5$ and $R_6$ together with tertiary carbon atom 25 form a cyclopropyl ring, as known for the normal series (WO 94/07853), by aldol reaction with an acetoacetic ester component of general formula XIX,

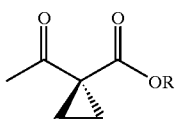
XIX whereby R means a straight-chain alkyl group with 1–6 carbon atoms, a compound of general formula XX can be obtained.

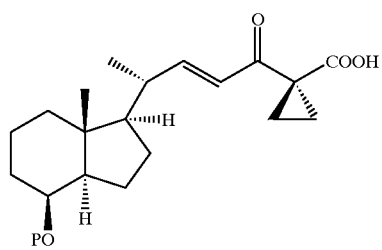
XX

Via intermediate products XXI, XXII and XXIII, the compound of general formula XXIV is then available.

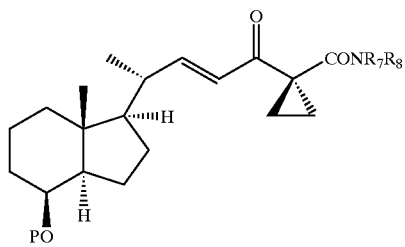
XXI

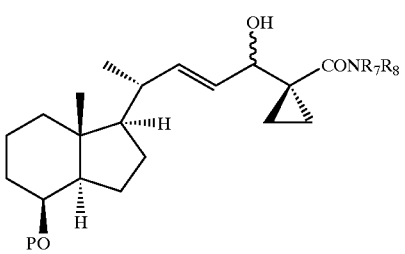
XXII

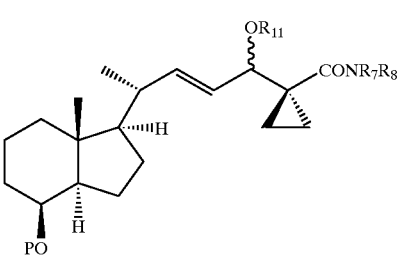
XXIII

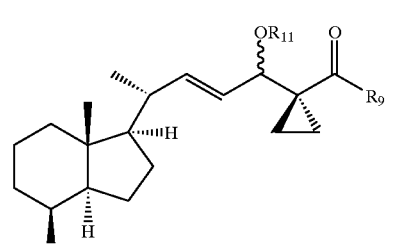
XXIV

The chemical manipulations that are necessary in this respect as well as the meanings of P, $R_7$, $R_8$, $R_9$ and $R_{11}$ have already been described elsewhere. By reduction of the keto group with a reducing agent (e.g., $NaBH_4$, $NaBH_4/CeCl_3$, $LiAlH_4$, DIBAH, TIBA, RedAl), a compound of general formula XXV is available, whose hydroxy group is provided with an acid-stable protective group that is to be removed by basic action (e.g., $R_{14}$=acetyl, propionyl, pivaloyl, benzoyl group), whereby a compound of general formula XXVI is obtained. Separations of diastereomeric hydroxy groups are carried out in each case in suitable intermediate stages.

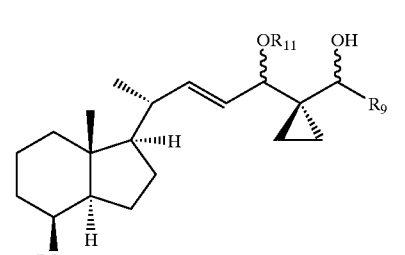
XXV

XXVI

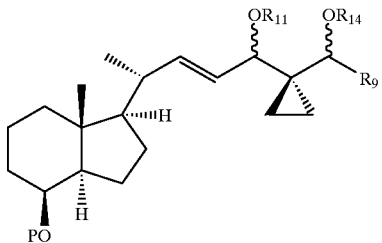

In the selection of suitable protective groups (e.g., P=Et₃Si, $R_{11}$=THP, $R_{14}$=Ac), group P can be selectively cleaved and by oxidation of the hydroxy group, the compound of general formula XXVII can be converted with an oxidizing agent (PCC, PDC, BaMnO₄, Swern conditions, Dess-Martin reagent) into a CD fragment of general formula XXVIII.

XXVII

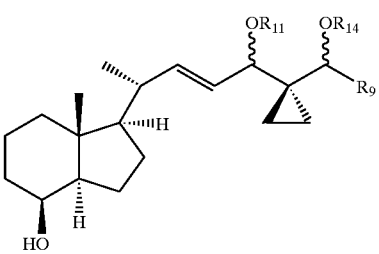

XXVIII

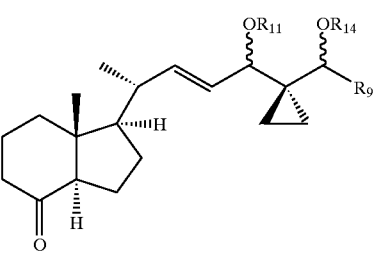

The compounds of general formula XXVIII are now converted by reaction with the anion of the phosphine oxide of general formula XXIX, known in the literature, that is produced by a base such as n-butyllithium or LDA [H. F. DeLuca et al. Tetrahedron Lett. 32, 7663, (1991)],

XXIX

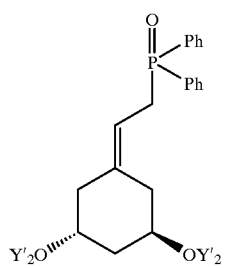

in which $Y'_2$ has the already described meaning, into the corresponding compounds of general formula XXX.

XXX

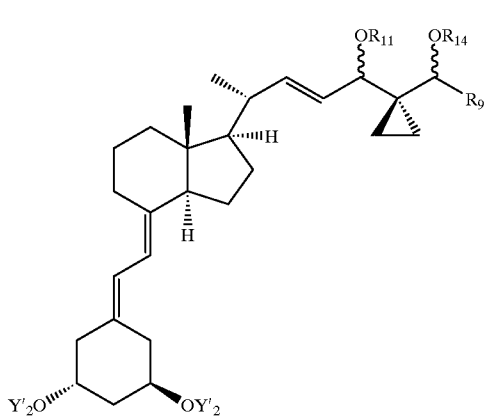

Successively or simultaneously, the protective groups are now removed ($R_{14}$ by basic hydrolysis, $R_{11}$ as well as $Y'_2$ by acid hydrolysis or fluoride reagents) and, as desired, one or both of the side chain hydroxy groups are oxidized with the already frequently mentioned oxidizing agent, whereby compounds of general formula I result, for which: $R_1$ and $R_2$ are hydrogen atoms and $R_5$ and $R_6$ together with tertiary carbon atom 25 form a cyclopropyl ring. The additional definitions were already mentioned.

As an alternative, protective group P in general formula XXIII can be selectively cleaved, if: P=silyl protective group, $R_{11}$=tetrahydropyranyl or tetrahydrofuranyl protective group. This can be carried out, e.g., with tetrabutylammonium fluoride, whereby compounds of general formula XXXI result.

XXXI

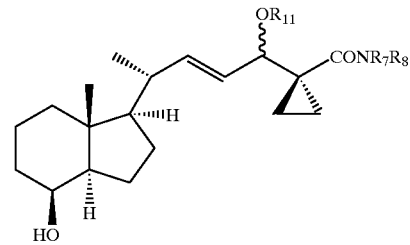

The free hydroxy group can now be oxidized with an oxidizing agent (PCC, PDC, BaMnO₄, Swern conditions, Dess-Martin reagent), whereby compounds of general formula XXXII are produced,

XXXII

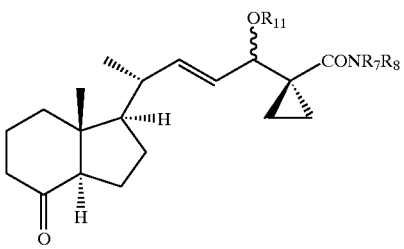

which are converted with the anion of phosphine oxide XXIX that is produced by a base (n-butyllithium, lithium diisopropylamide) into compounds of general formula XXXIII.

XXXIII

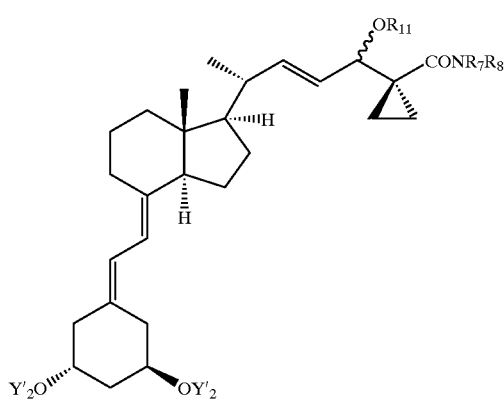

Analogously to the compounds in the normal series (e.g., VII), the building of radical Z' now takes place, whereby compounds of general formula XXXIV result.

XXXIV

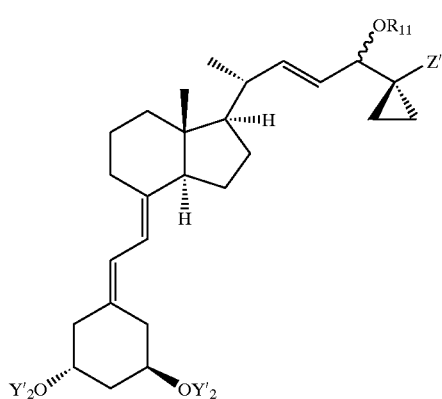

These can be considered a special case of general formula II', whereby all variables have already been described previously. The further treatment of the compounds of general formula II' has also been indicated above.

If $R_5$ and $R_6$ do not form a cyclopropyl ring together with tertiary carbon atom 25, rather the other above-mentioned definitions are to apply, the building of the side chain takes place with a somewhat modified synthesis method. The known CD-portion of general formula XXXV (WO 94/07853) can be converted, analogously to the normal series, into derivatives of general formulas XXXVI and XXXVII,

XXXV

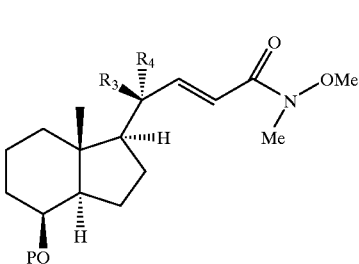

-continued

XXXVI

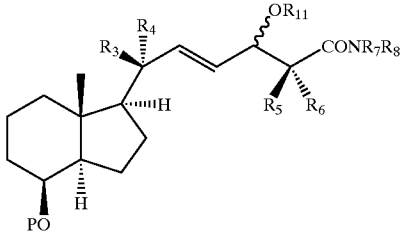

XXXVII

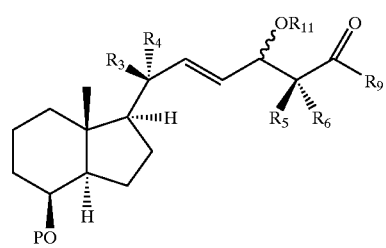

whereby all variables have the already mentioned definitions. The diastereomers can be separated into suitable intermediate stages.

By direct reaction of the lithium organyls of general formula VIII ($LiR_9$) with compounds of general formulas XXXVI and XXXVII, compounds of general formula XXXVIII can now be generated, and as shown before, are converted into a compound of general formula II'.

The diastereomeric alcohols (relative to C-24) can be reacted separated in advance and reacted separately.

XXXVIII

In principle, the introduction of correspondingly substituted side chains or their precursors can also be carried out on aldehydes of general formulas III or IV or their 5Z-isomers with use of established synthesis methods.

The following examples are used for a more detailed explanation of the invention.

EXAMPLE 1

Figure 1:
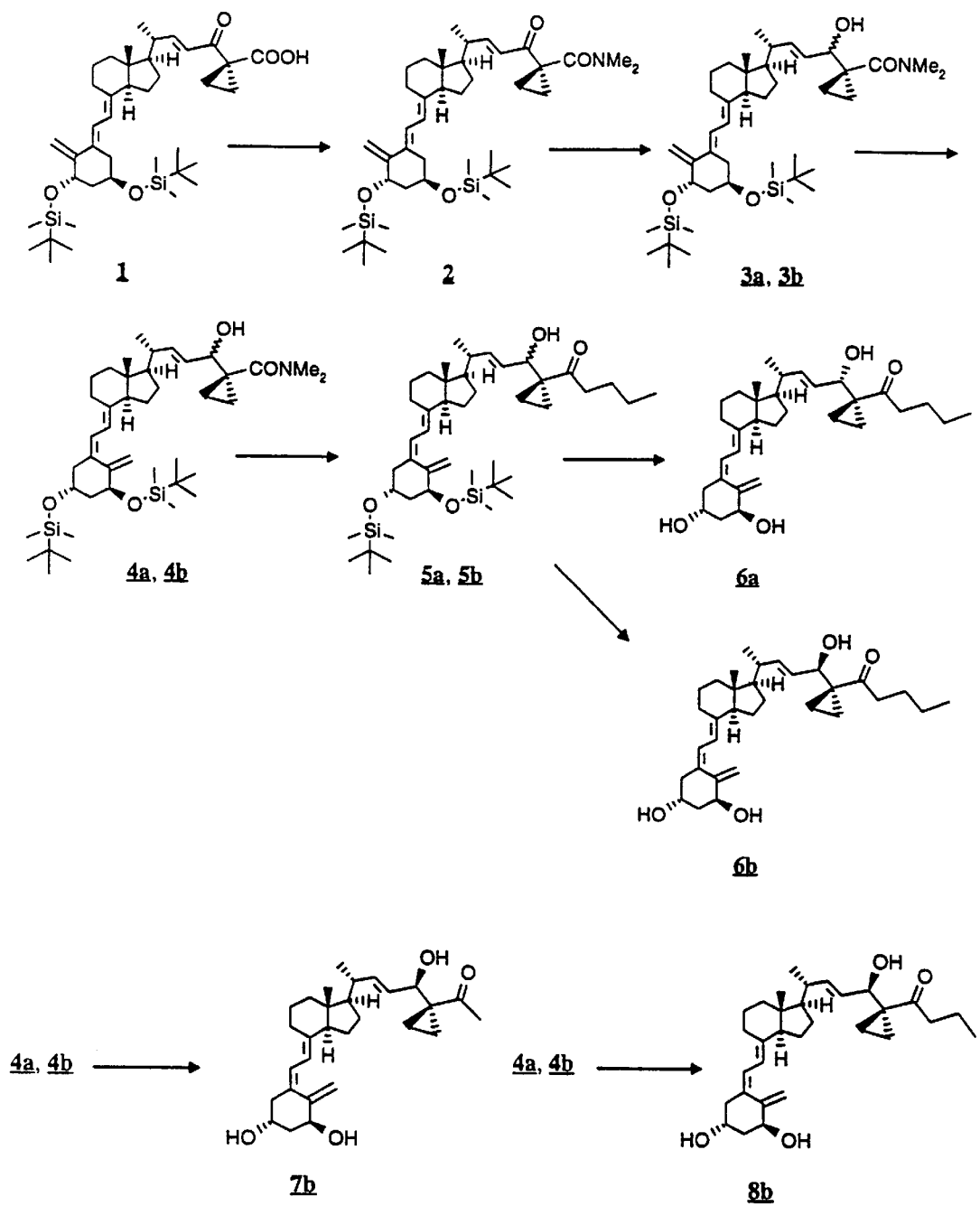
FIGS. 1–14 are reaction schemes depicting the syntheses of C-25 substituted vitamin D derivatives.
Figure 2:
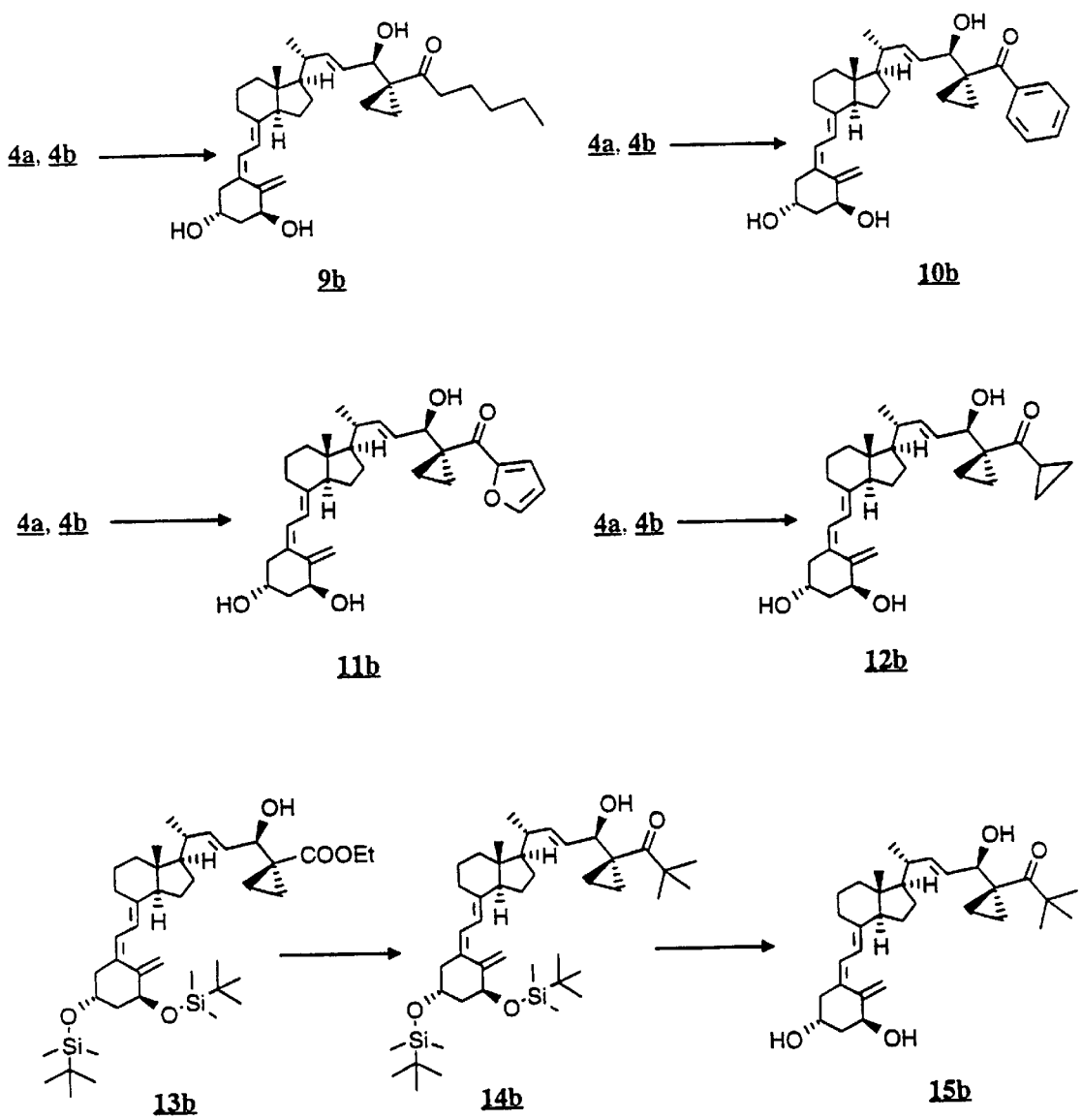
Figure 3:
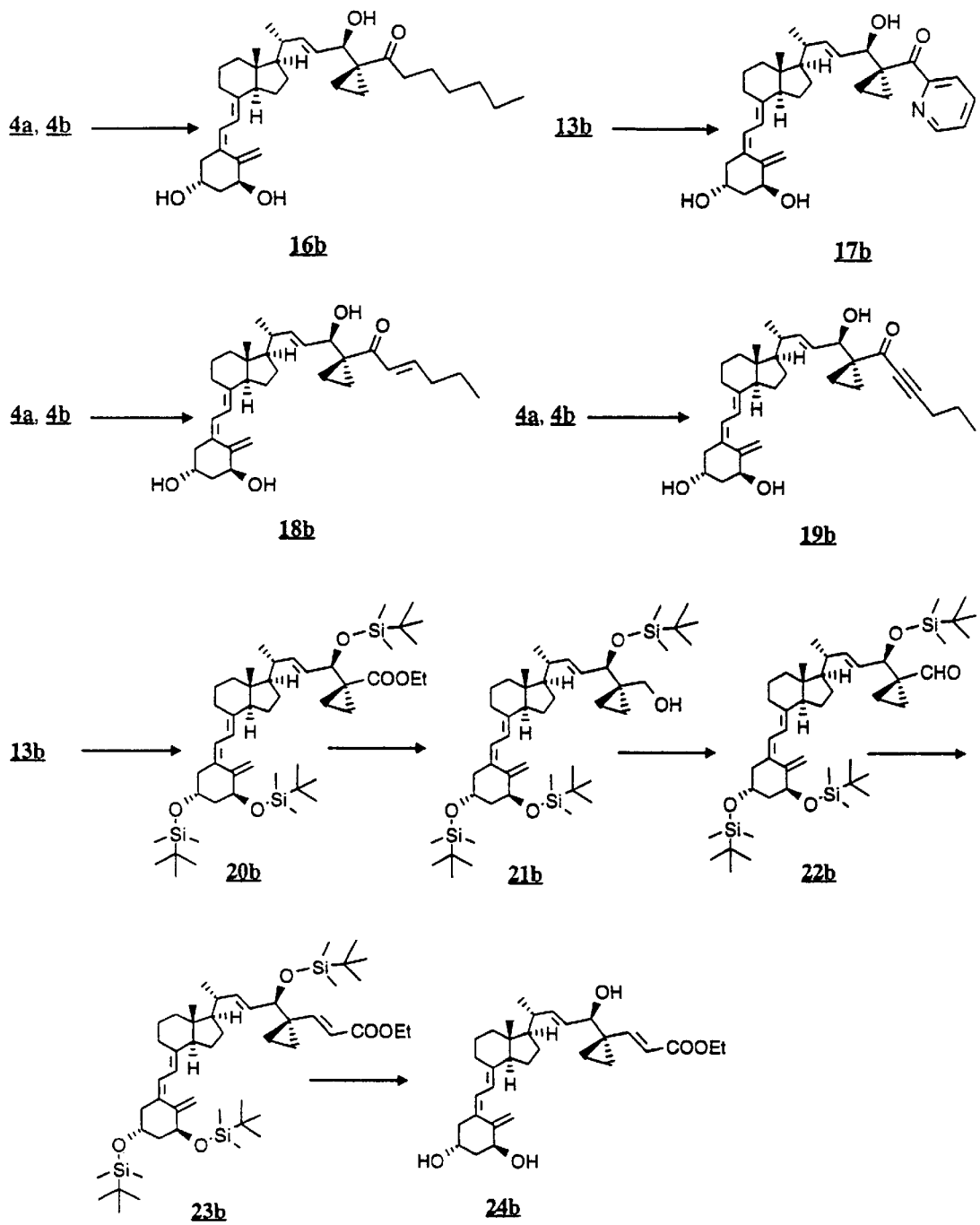
Figure 4:
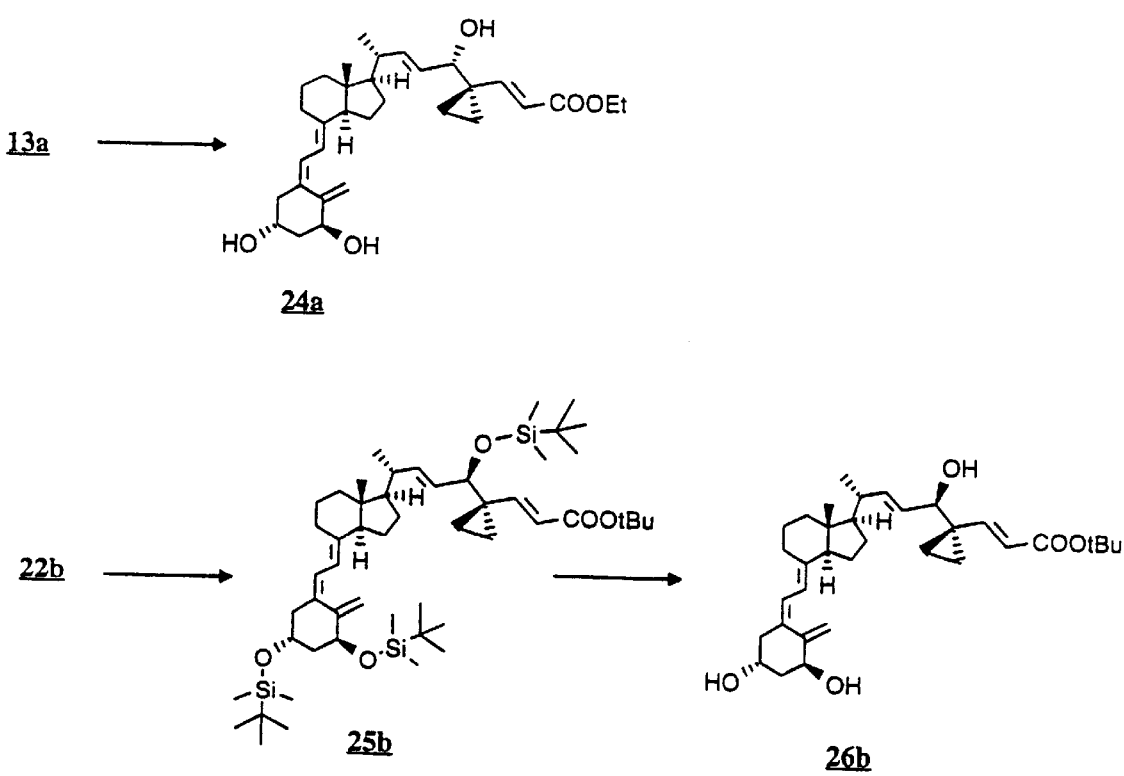
Figure 5:
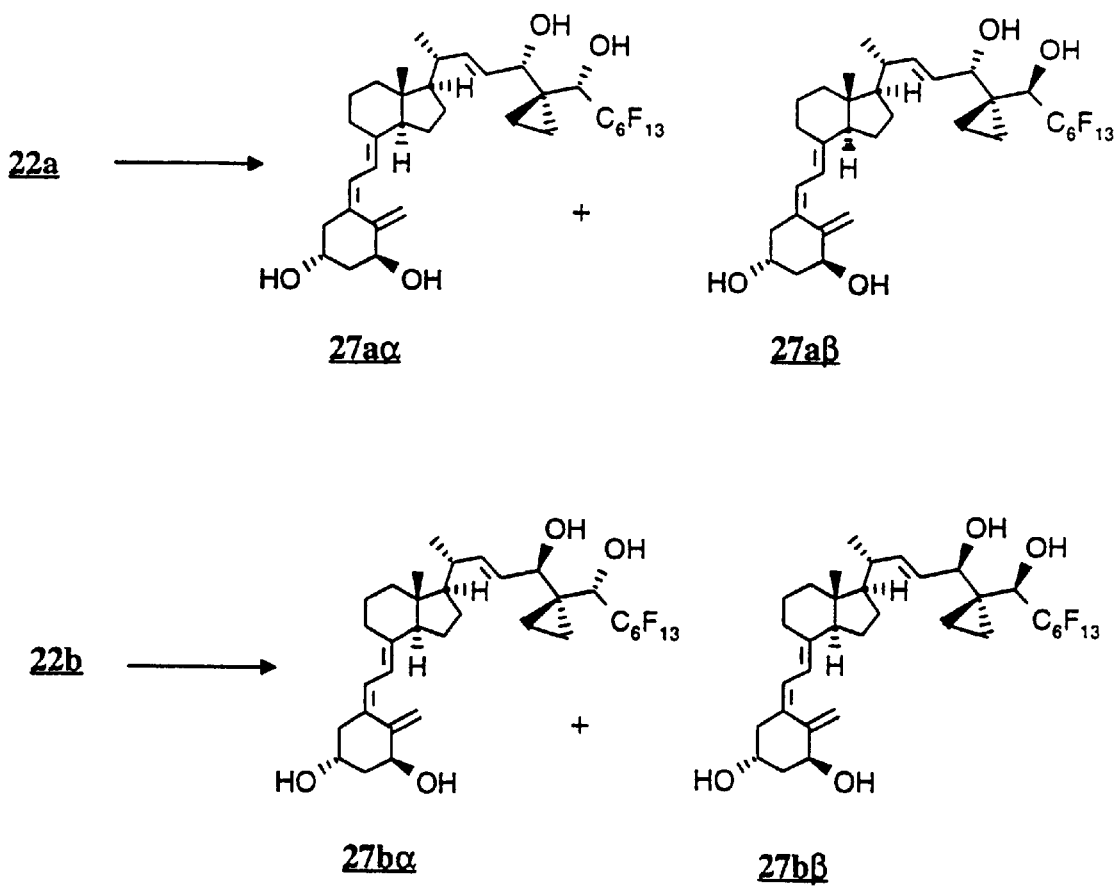
Figure 6:
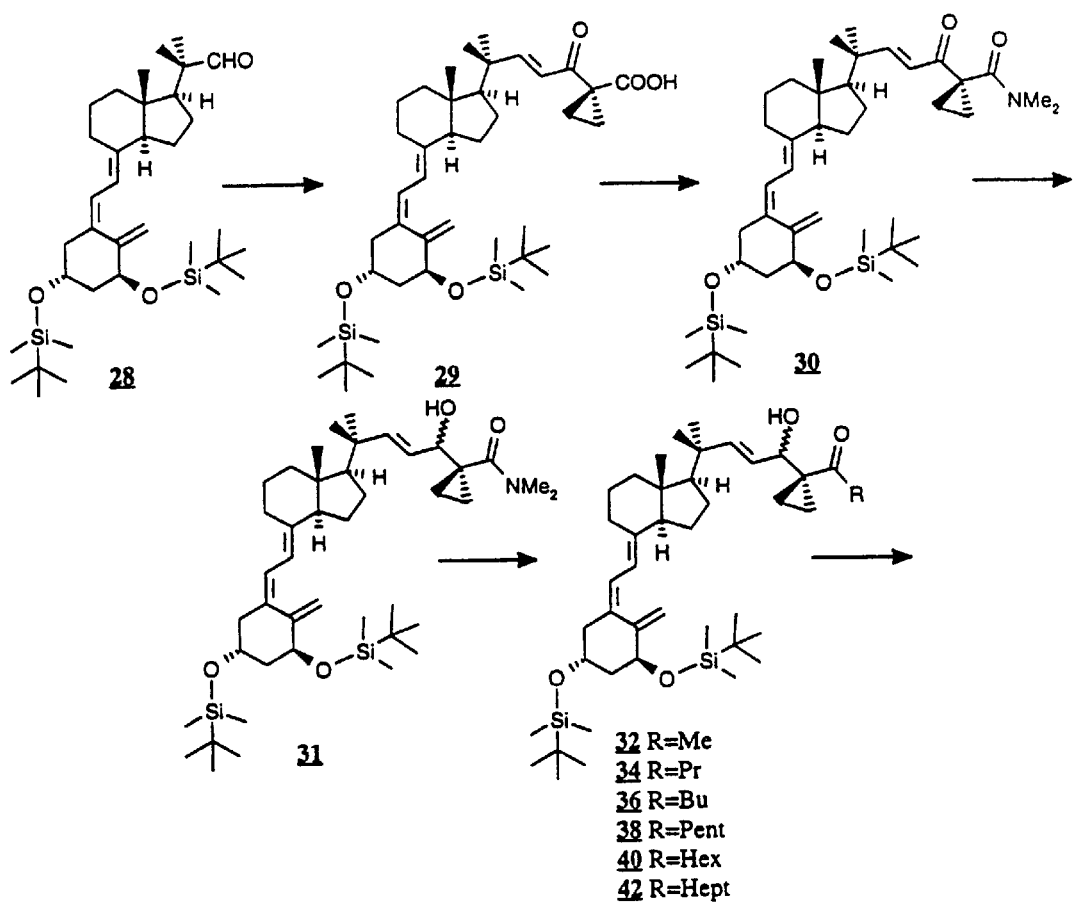
Figure 6:
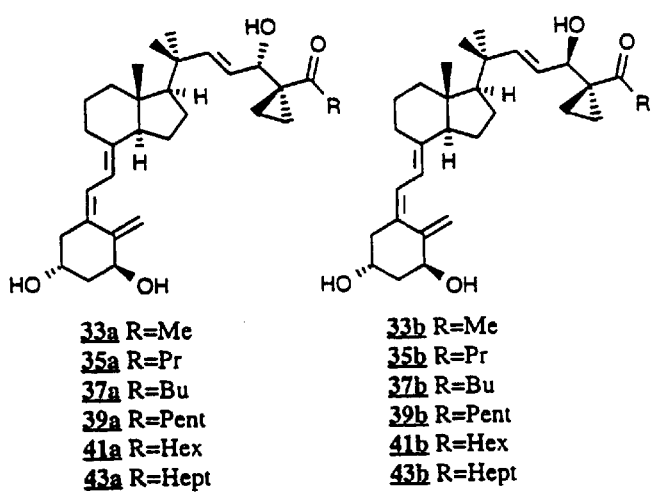
Figure 7:
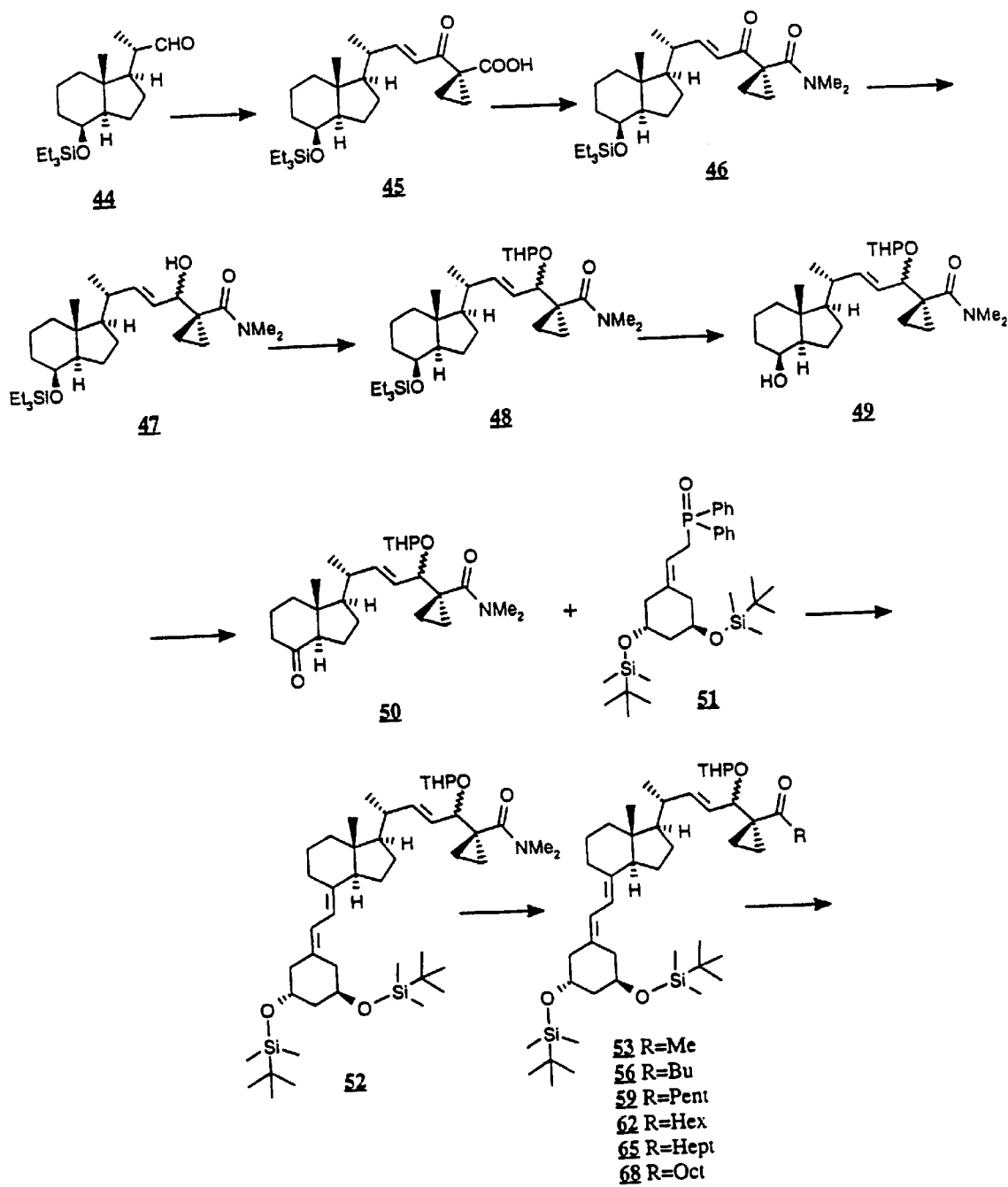
Figure 8:
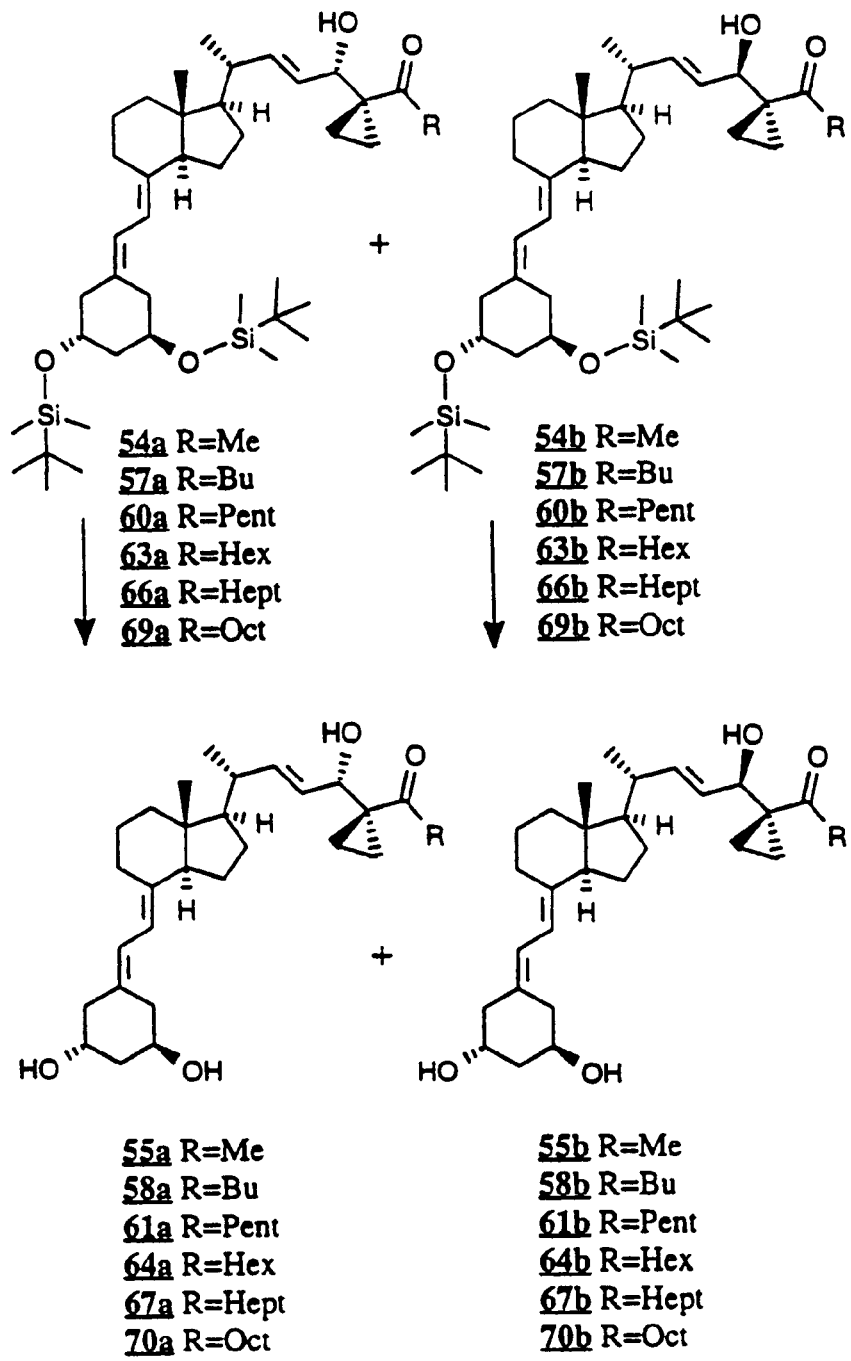
Figure 9:
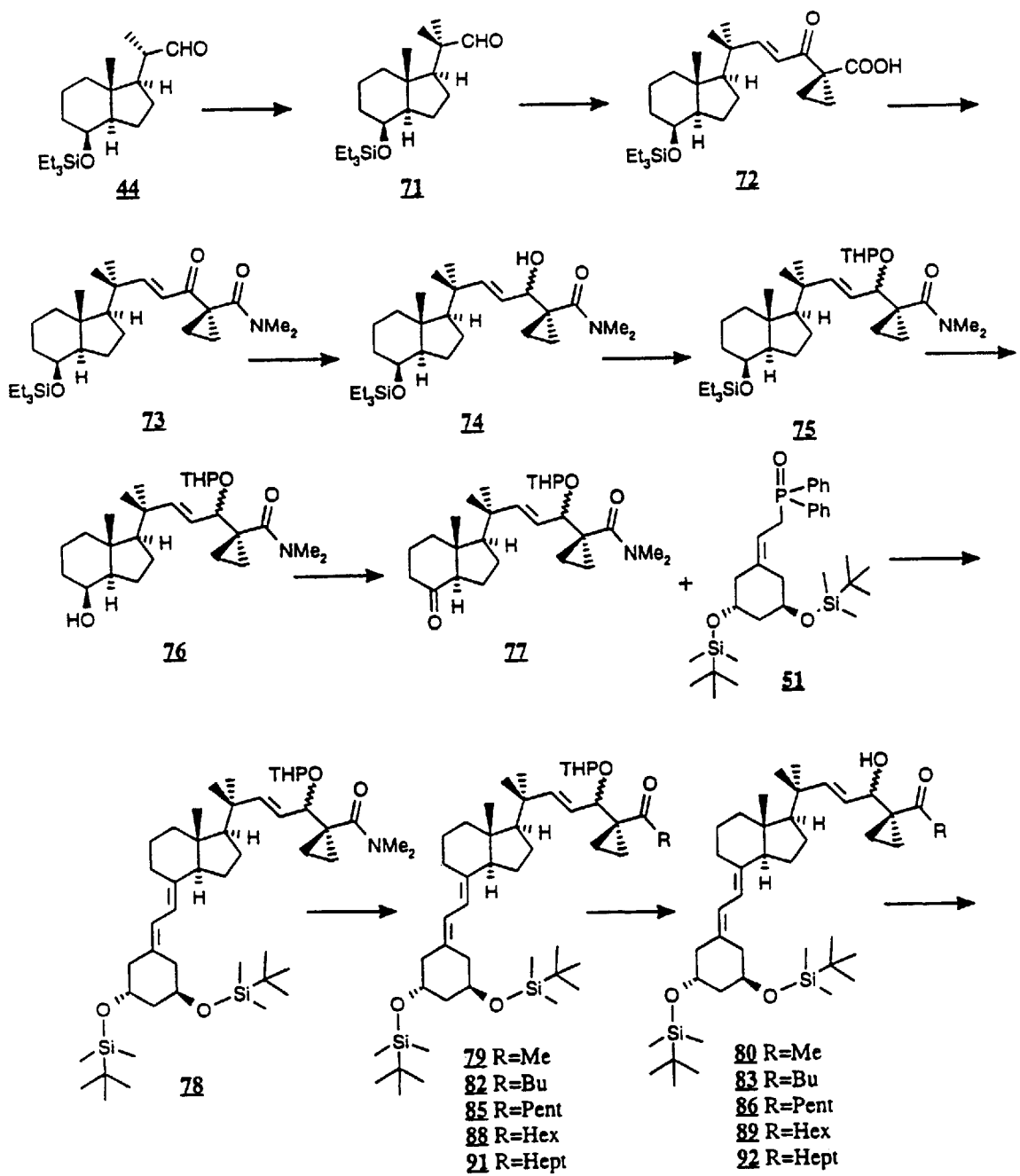
Figure 10:
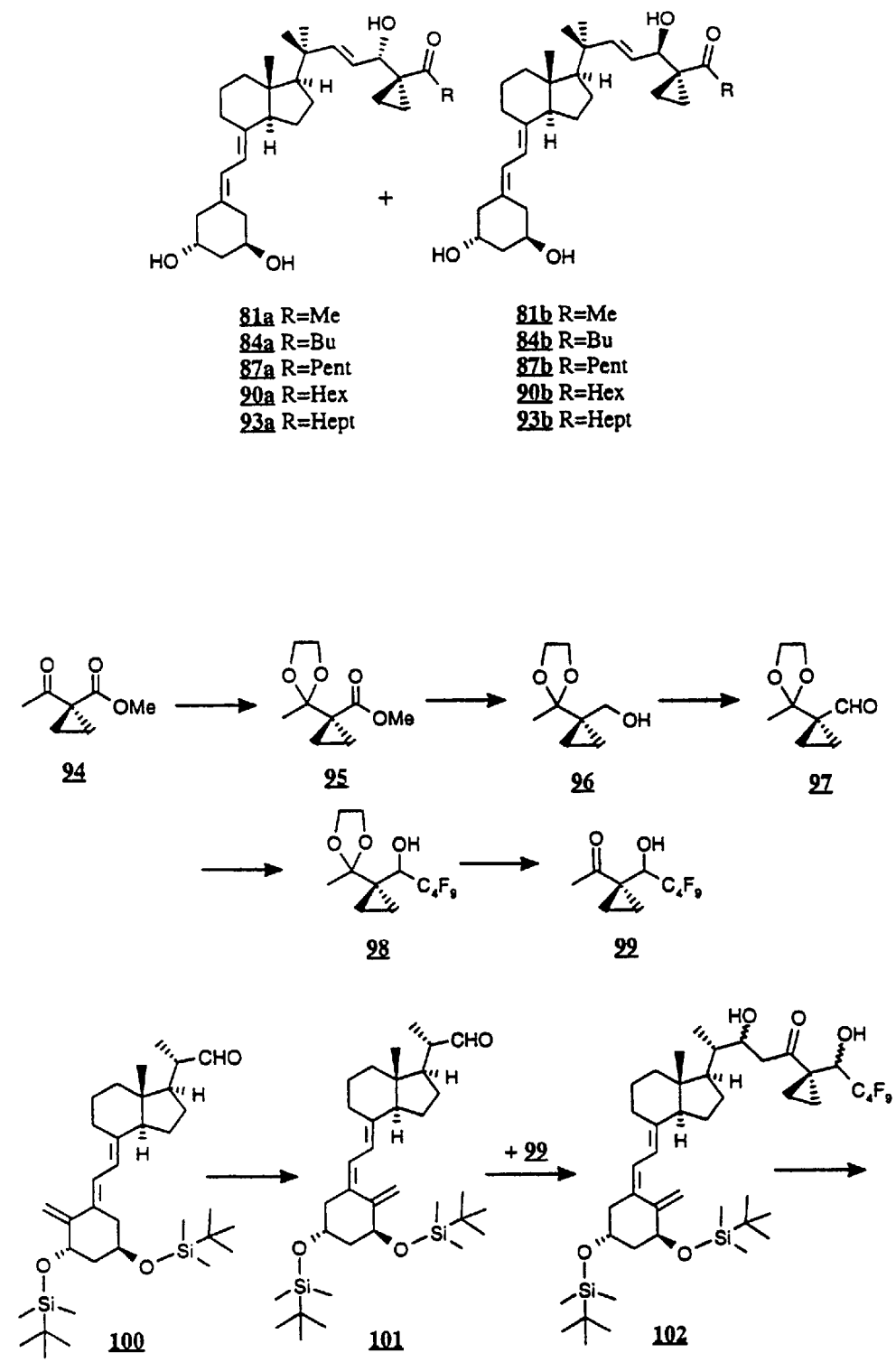
Figure 11:
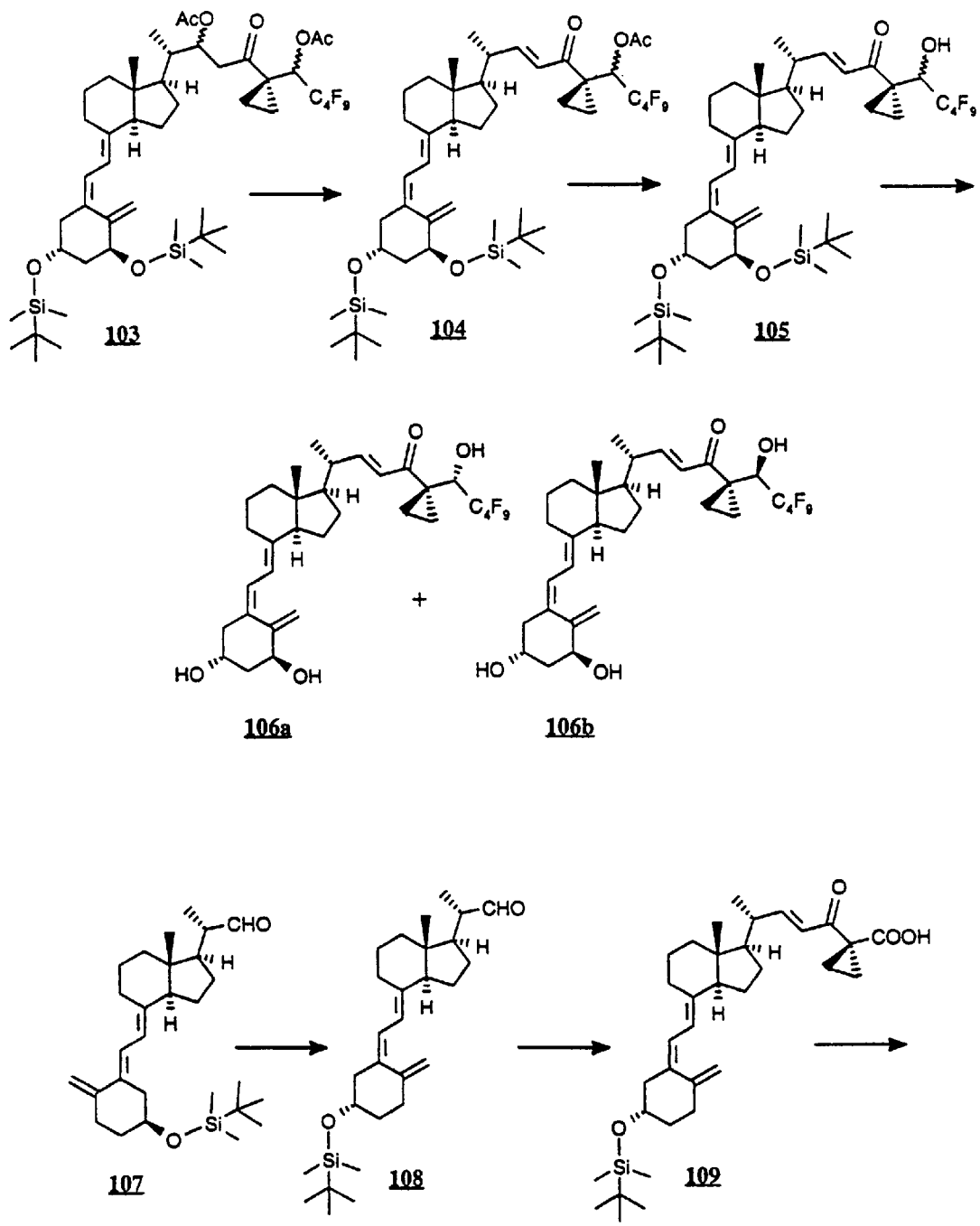
Figure 12:
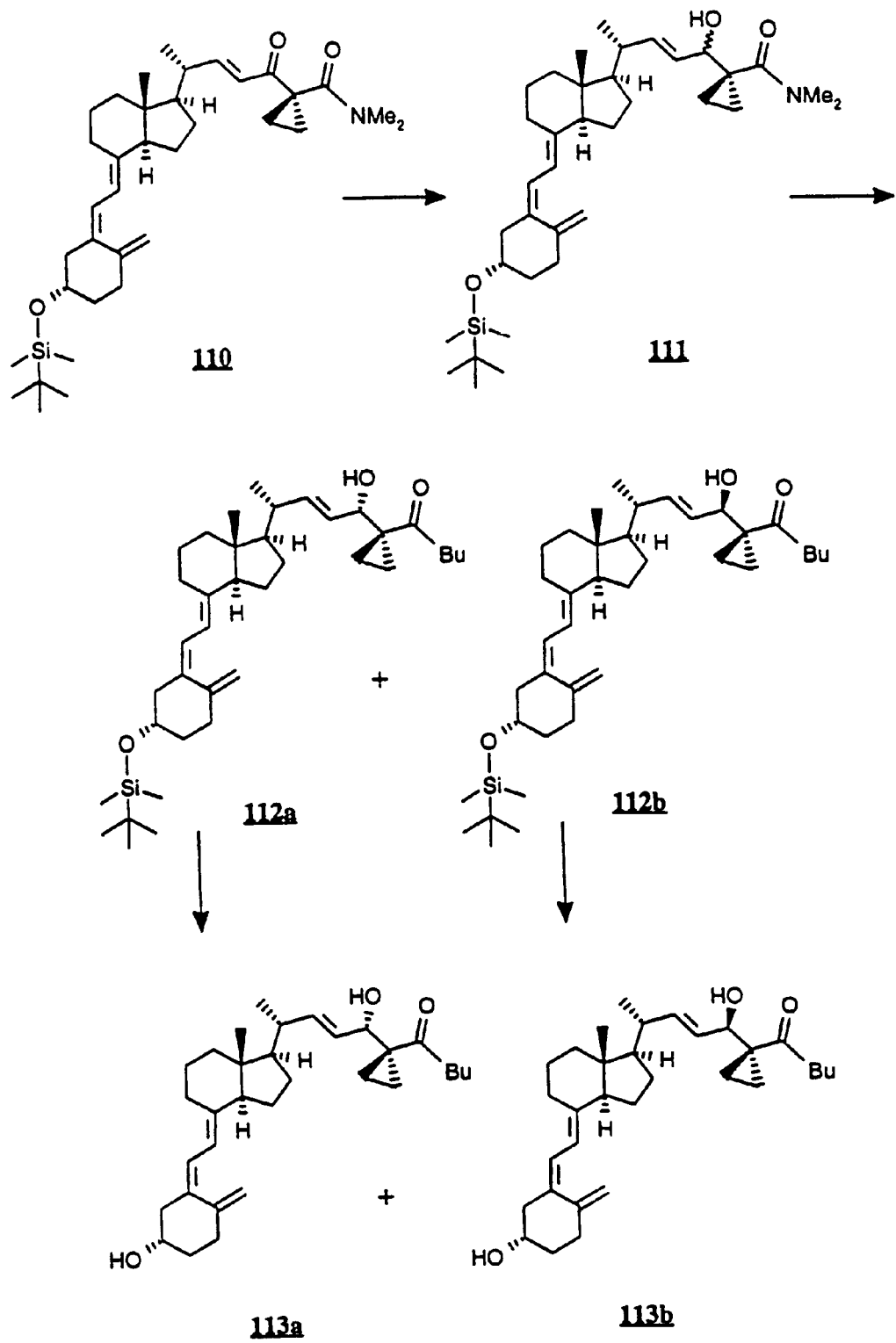
Figure 13:
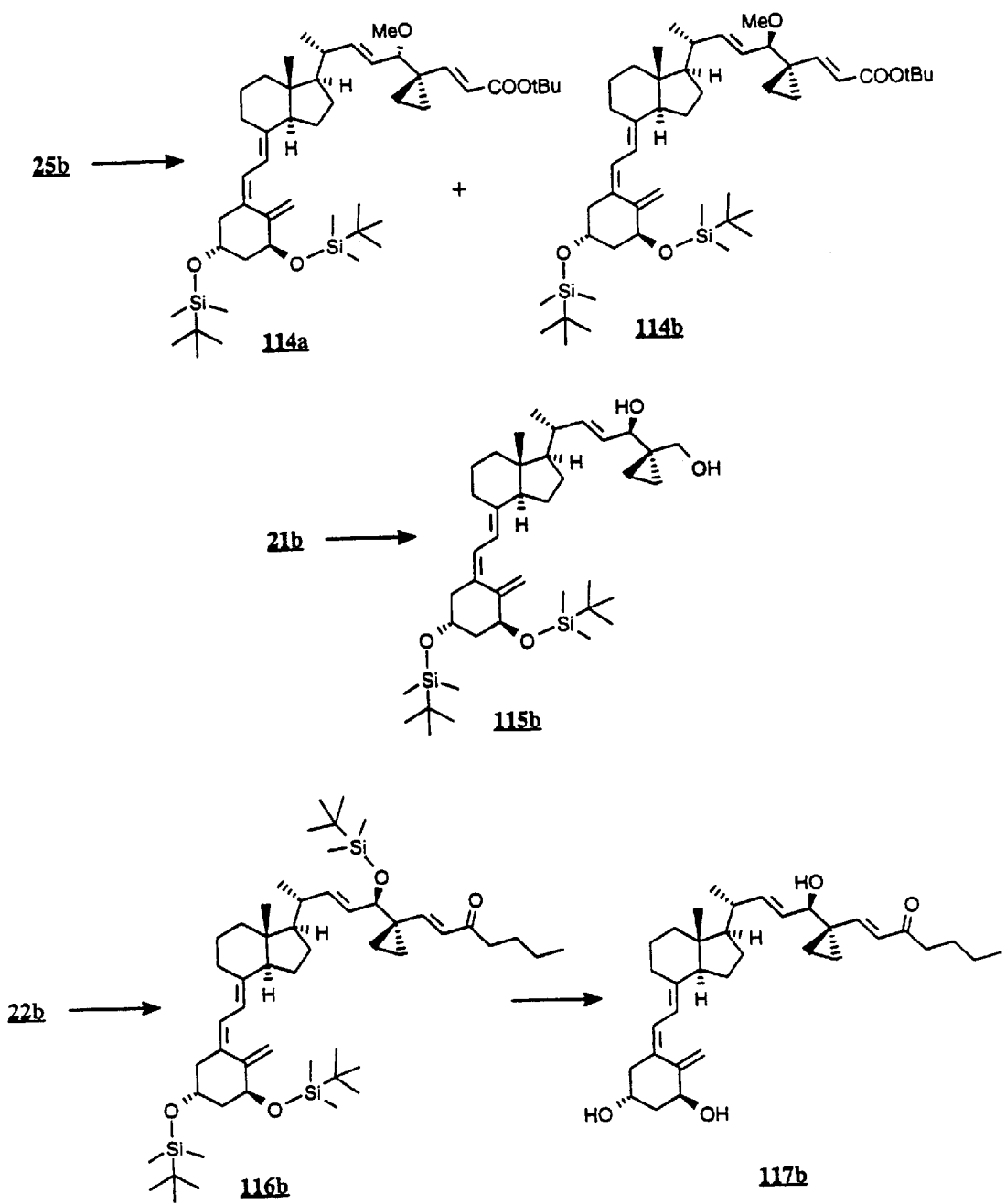
Figure 14:
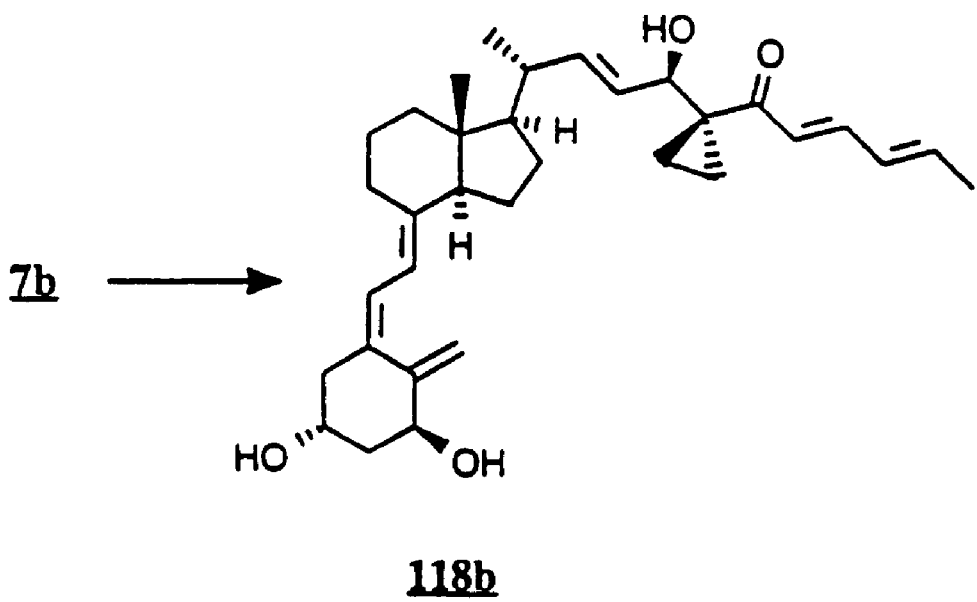

(5Z,7E,22E)-(1S,3R,24R)-25-(1-Oxopentyl)-26,27-cyclo-9,10-secocholesta-5,7,10(19),22-tetraene-1,3,24-triol (6b)

a) An amount of 5.0 g of (5E,7E,22E)-(1S,3R)-1,3-bis[[dimethyl(1,1-dimethylethyl)silyl]oxy]-24-oxo-26,27-cyclo-9,10-secocholesta-5,7,10(19),22-tetraene-25-carboxylic acid 1 (WO 94/07853) and 1.01 g of N-hydroxysuccinimide are dissolved in 21 ml of methylene chloride and mixed with 1.87 g of N,N'- dicyclohexylcarbodiimide at 0° C. After 1.5 hours, 2.04 ml of a 40% aqueous dimethylamine solution is added and stirred for another 30 minutes at 0° C. After 3 hours at room temperature, the reaction mixture is chromatographed on silica gel with ethyl acetate/hexane (1:4). 2.08 g of (5E,7E, 22E)-(1S,3R)-1,3-bis-[[dimethyl(1,1-dimethyl-ethyl)silyl] oxy]-N,N-dimethyl-24-oxo-26,27-cyclo-9,10-secocholesta-5,7,10(19),22-tetraene-25-carboxylic acid amide 2 is obtained as a colorless compound.

b) 1.39 g of amide 2 is dissolved in 3.3 ml of THF and 7.7 ml of methanol and mixed with 7.7 ml of a 0.4 molar methanolic cerium trichloride (hydrate) solution. 210 mg of sodium borohydride is now added in portions at 0° C. It is stirred for 45 more minutes at 0° C. and then mixed with an ice/water mixture. Then, it is extracted with ethyl acetate, dried on sodium sulfate and concentrated by evaporation. The oily residue (1.32 g) is a diastereomer mixture that consists of (5E,7E,22E)-(1S,3R,24S)-1,3-bis[[dimethyl(1,1-dimethylethyl)silyl]oxy]-N,N-dimethyl-24-hydroxy-26,27-cyclo-9,10-secocholesta-5,7,10(19),22-tetraene-25-carboxylic acid amide 3a and the 24R-diastereomer 3b.

c) 2.48 g of the epimer mixture 3a and 3b is dissolved in 348 ml of toluene and, after 383 mg of anthracene and 7 drops of triethylamine are added, it is irradiated through Pyrex glass with a mercury high-pressure lamp (Heraeus TQ 150) for 19 minutes under nitrogen. The reaction mixture that is concentrated by evaporation is mixed with hexane, filtered and again concentrated by evaporation. The residue of 2.82 g is a mixture of (5Z,7E,22E)-(1S,3R,24S)-1,3-bis [[dimethyl(1,1-dimethylethyl)silyl]oxy]-N,N-dimethyl-24-hydroxy-26,27-cyclo-9,10-secocholesta-5,7,10(19),22-tetraene-25-carboxylic acid amide 4a and the corresponding 24R-diastereomer 4b.

d) The diastereomer mixture that consists of 4a and 4b (2.82 g) is dissolved in 28 ml of THF and mixed drop by drop with 6.53 ml of n-butyllithium solution (1.6 M in hexane) at 0° C. After 75 minutes, saturated ammonium chloride solution is added to the reaction solution, extracted with ethyl acetate, dried on sodium sulfate and concentrated by evaporation. By chromatography of the residue on silica gel with ethyl acetate/hexane, 0.84 g of (5Z,7E,22E)-(1S, 3R,24S)-1,3-bis[[dimethyl(1,1-dimethylethyl)silyl]oxy]-25-(1-oxopentyl)-26,27-cyclo-9,10-secocholesta-5,7,10(19), 22-tetraen-24-ol 5a and 0.64 g of (5Z,7E,22E)-(1S,3R,24R)-1,3-bis[[dimethyl(1,1-dimethylethyl)silyl]oxy]-25-(1-oxopentyl)-26,27-cyclo-9,10-secocholesta-5,7,10(19),22-tetraen-24-ol 5b are obtained in the elution sequence as oils.

e) 0.62 g of epimer 5b is allowed to stand in 24.9 ml of THF with 1.32 g of tetrabutylammonium fluoride (trihydrate) overnight at room temperature. The reaction mixture is then poured onto a mixture of ice/sodium bicarbonate solution/sodium chloride solution. After extraction with ethyl acetate, the organic phase is dried on sodium sulfate and concentrated by evaporation. Chromatography of the residue on silica gel with ethyl acetate/hexane yields 125 mg of title compound 6b as a foam.

$^1$H-NMR (300 MHz, CDCl$_3$): δ=0.57 ppm (s, 3H); 0.91 (t, 3H); 1.00 (m, 2H); 1.05 (d, 3H); 1.22 (m, 2H); 2.15 (t, 2H); 3.29 (brd, 1H); 4.08 (m,1H); 4.22 (m, 1H); 4.42 (m, 1H); 5.00 (brs, 1H); 5.32 (brs, 1H); 5.35 (dd, 1H); 5.49 (dd, 1H); 6.01 (d, 1H); 6.38 (d, 1H)

EXAMPLE 2

(5Z,7E,22E)-(1S,3R,24S)-25-(1-Oxopentyl)-26,27-cyclo-9,10-secocholesta-5,7,10(19),22-tetraene-1,3,24-triol (6a)

Analogously to the implementation according to 1e), epimer 5a is reacted, whereby title compound 6a is obtained as a crystallizing oil.

$^1$H-NMR (300 MHz, CDCl$_3$): δ=0.57 ppm (s, 3H); 0.90 (t, 3H); 1.00 (m, 2H); 1.05 (d, 3H); 1.22 (m, 2H); 2.16 (t, 2H); 3.25 (brs, 1H); 4.12 (m 1H); 4.23 (m, 1H); 4.43 (m, 1H); 5.00 (brs, 1H); 5.32 (brs, 1H); 5.36 (dd, 1H); 5.55 (dd, 1H); 6.01 (d, 1H); 6.38 (d, 1H)

EXAMPLE 3

(5Z,7E,22E)-(1S,3R,24R)-25-Acetyl-26,27-cyclo-9,10-secocholesta-5,7,10(19),22-tetraene-1,3,24-triol (7b)

Starting with the epimer mixture 4a and 4b, title compound 7b is obtained, analogously to Example 1d)–e) as crystals with methyllithium (melting point: 138–140° C.).

$^1$H-NMR (300 MHz, CDCl$_3$): δ=0.57 ppm (s, 3H); 1.00 (m, 2H); 1.05 (d, 3H); 1.22 (m, 2H); 1.96 (s, 3H); 3.16 (brd, 1H); 4.12 (m, 1H); 4.23 (m, 1H); 4.43 (m, 1H); 5.00 (brs, 1H); 5.32 (brs, 1H); 5.36 (dd, 1H); 5.50 (dd, 1H); 6.01 (d, 1H); 6.38 (d, 1H)

EXAMPLE 4

(5Z,7E,22E)-(1S,3R,24R)-25-(1-Oxobutyl)-26,27-cyclo-9,10-secocholesta-5,7,10(19),22-tetraene-1,3,24-triol (8b)

Starting with the epimer mixture 4a and 4b, title compound 8b is obtained, analogously to Example 1d)–e), as a foam with propyllithium (that consists of n-propyl bromide and lithium in ether).

$^1$H-NMR (300 MHz, CDCl$_3$): δ=0.57 ppm (s, 3H); 0.90 (t, 3H); 1.00 (m, 2H); 1.05 (d, 3H); 1.20 (m, 2H); 2.13 (t, 2H); 3.25 (brs, 1H); 4.10 (m, 1H); 4.23 (m, 1H); 4.43 (m, 1H); 5.00 (brs, 1H); 5.32 (brs, 1H); 5.38 (dd, 1H); 5.50 (dd, 1H); 6.01 (d, 1H); 6.38 (d, 1H)

EXAMPLE 5

(5Z,7E,22E)-(1S,3R,24R)-25-(1-Oxohexyl)-26,27-cyclo-9,10-secocholesta-5,7,10(19),22-tetraene-1,3,24-triol (9b)

Starting with the epimer mixture 4a and 4b, title compound 9b is obtained, analogously to Example 1d)–e), as a foam with pentyllithium (that consists of n-pentyl bromide and lithium in ether).

$^1$H-NMR (300 MHz, CDCl$_3$): δ=0.57 ppm (s, 3H); 0.90 (t, 3H); 1.00 (m, 2H); 1.05 (d, 3H); 1.22 (m, 2H); 2.13 (t, 2H); 3.30 (brs, 1H); 4.08 (m, 1H); 4.23 (m, 1H); 4.43 (m, 1H); 5.00 (brs, 1H); 5.32 (brs, 1H); 5.37 (dd, 1H); 5.50 (dd, 1H); 6.01 (d, 1H); 6.38 (d, 1H)

EXAMPLE 6 (10b)

(5Z,7E,22E)-(1S,3R,24R)-25-Benzoyl-26,27-cyclo-9,10-secocholesta-5,7,10(19),22-tetraene-1,3,24-triol Starting with the epimer mixture 4a and 4b, title compound 10b is obtained, analogously to Example 1d)–e), as a foam with phenyllithium.

$^1$H-NMR (300 MHz, CDCl$_3$): δ=0.57 ppm (s, 3H); 1.01 (d, 3H); 1.08 (m, 2H); 1.22 (m, 2H); 2.20 (brd, 1H); 4.23 (m, 1H); 4.45 (m, 2H); 5.00 (brs, 1H); 5.31 (dd, 1H); 5.32 (dd, 1H); 5.48 (dd, 1H); 6.01 (d, 1H); 6.38 (d, 1H); 7.45 (m, 3H); 7.75 (d, 2H)

EXAMPLE 7

(5Z,7E,22E)-(1S,3R,24R)-25-(2-Furanylcarbonyl)-26,27-cyclo-9,10-secocholesta-5,7,10(19),22-tetraene-1,3,24-triol (11b)

Starting with the epimer mixture 4a and 4b, title compound 11b is obtained, analogously to Example 1d)–e), as a solid with 2-furyllithium (production of furan with n-butyllithium in THF) in the case of inverse addition (−78° C., then 0° C., 1 hour).

$^1$H-NMR (300 MHz, CDCl$_3$): δ=0.57 ppm (s, 3H); 1.02 (d, 3H); 1.08 (m, 2H); 1.18 (m, 2H); 3.12 (brd, 1H); 4.22 (m, 2H); 4.42 (m, 1H); 5.00 (brs, 1H); 5.32 (dd, 1H); 5.43 (dd, 1H); 5.53 (dd, 1H); 6.01 (d, 1H); 6.38 (d, 1H); 6.50 (m, 1H); 7.20 (d, 1H); 7.51 (brs, 1H)

EXAMPLE 8

(5Z,7E,22E)-(1S,3R,24R)-25-(Cyclopropylcarbonyl)-26,27-cyclo-9,10-secocholesta-5,7,10(19),22-tetraene-1,3,24-triol (12b)

Starting with the epimer mixture 4a and 4b, the title compound is obtained, analogously to Example 1d)–e), as a foam with cyclopropyl lithium (that consists of cyclopropyl bromide and lithium in ether).

$^1$H-NMR (300 MHz, CDCl$_3$): δ=0.57 ppm (s, 3H); 0.83 (m, 2H); 1.05 (m, 10H); 3.48 (brd, 1H); 4.13 (m, 1H); 4.23 (m, 1H); 4.45 (m, 1H); 5.00 (brs, 1H); 5.32 (dd, 1H); 5.40 (dd, 1H); 5.50 (dd, 1H); 6.01 (d, 1H); 6.38 (d, 1H) cl

EXAMPLE 9

(5Z,7E,22E)-(1S,3R,24R)-25-(2,2-Dimethyl-1-oxopropyl)-26,27-cyclo-9,10-secocholesta-5,7,10 (19),22-tetraene-1,3,24-triol (15b)

a) 580 mg of (5Z,7E,22E)-(1S,3R,24R)-1,3-bis[[dimethyl (1,1-dimethylethyl)silyl]oxy]-24-hydroxy-26,27-cyclo-9,10-secocholesta-5,7,10(19),22-tetraene-25-carboxylic acid ethyl ester 13b (WO 94/07853) in 6.4 ml of diethyl ether is mixed drop by drop with 2.04 ml of tert-butyllithium (1.7 M in pentane) at −78° C. After 1 hour at −78° C., ammonium chloride solution is added, extracted with ethyl acetate, the organic phase is washed with sodium chloride solution, dried on sodium sulfate and concentrated by evaporation. Chromatography of the oily residue on silica gel with ethyl acetate/hexane yields 220 mg of (5Z,7E,22E)-(1S,3R,24R)-1,3-bis[[dimethyl(1,1-dimethylethyl)silyl]oxy]-25-(2,2-dimethyl-1-oxopropyl)-26,27-cyclo-9,10-secocholesta-5,7,10(19),22-tetraen-24-ol 14b as an oil.

b) 220 mg of 14b is dissolved in 8.8 ml of THF and allowed to stand with 467 mg of tetrabutylammonium fluoride (trihydrate) overnight at room temperature. Working-up and isolation are carried out analogously to Example 1e), whereby title compound 15b accumulates as a solid.

$^1$H-NMR (300 MHz, CDCl$_3$): δ=0.57 ppm (s, 3H); 0.80–1.00 (m, 4H); 1.05 (d, 3H); 1.20 (s, 9H); 3.00 (brs, 1H); 4.09 (m, 1H); 4.23 (m, 1H); 4.43 (m, 1H); 5.00 (brs, 1H); 5.29 (dd, 1H); 5.32 (brs, 1H); 5.52 (dd, 1H); 6.01 (d, 1H); 6.38 (d, 1H)

EXAMPLE 10

(5Z,7E,22E)-(1S,3R,24R)-25-(1-Oxoheptyl)-26,27-cyclo-9,10-secocholesta-5,7,10(19),22-tetraene-1,3,24-triol (16b)

Starting with the epimer mixture 4a and 4b, title compound 16b is obtained, analogously to Example 1d)–e), as a colorless foam with hexyllithium (that consists of 1-hexyl bromide and lithium in ether).

$^1$H-NMR (300 MHz, CDCl$_3$): δ=0.57 ppm (s, 3H); 0.90 (m, 5H); 1.05 (d, 3H); 2.13 (t, 2H); 3.30 (brd, 1H); 4.08 (m, 1H); 4.23 (m, 1H); 4.43 (m, 1H); 5.00 (brs, 1H); 5.32 (brs, 1H); 5.37 (dd, 1H); 5.50 (dd, 1H); 6.01 (d, 1H); 6.38 (d, 1H)

EXAMPLE 11

(5Z,7E,22E)-(1S,3R,24R)-25-(2-Pyridinylcarbonyl)-26,27-cyclo-9,10-secocholesta-5,7,10(19),22-tetraene-1,3,24-triol (17b)

2.03 ml of 2-bromopyridine in 38 ml of diethyl ether is mixed drop by drop with 13.3 ml of n-butyllithium (1.6 M in hexane) at −78° C. After 30 minutes, 1.98 g of (5Z,7E,22E)-(1S,3R,24R)-1,3-bis-[[dimethyl(1,1-dimethylethyl) silyl]oxy]-24-hydroxy-26,27-cyclo-9,10-secocholesta-5,7,10(19),22-tetraene-25-carboxylic acid ethyl ester 13b (WO 94/07853) in 19 ml of diethyl ether is added in drops. After 1.5 hours at −78° C., the reaction solution is mixed with saturated ammonium chloride solution, then extracted with ethyl acetate, the organic phase is dried on sodium sulfate and concentrated by evaporation. By chromatography on silica gel with ethyl acetate/hexane, 1.52 g of a colorless oil is obtained, which is dissolved in 60.2 ml of THF and allowed to stand with 3.19 g of tetrabutylammonium fluoride (trihydrate) overnight at room temperature. Working-up and isolation are carried out analogously to Example 1e). After recrystallization from isopropanol/water, the title compound with a melting point of 120–121° C. is obtained.

EXAMPLE 12

[5Z,7E,22E,25(E)]-(1S,3R,24R)-25-(1-Oxo-2-hexenyl)-26,27-cyclo-9,10-secocholesta-5,7,10(19), 22-tetraene-1,3,24-triol (18b)

11.5 ml of n-butyllithium (1.6 M in hexane) is added in drops at 0° C. to 3.61 g of (E)-1-iodo-1-pentene [that consists of 1-pentine, DIBAH and iodine analogously to J. K. Stille et al. J. Am. Chem. Soc. 109, 2138 (1987), T. Yokoo Synlett 645 (1994)] in 90 ml of hexane. After 15 minutes, 180 mg of (5Z,7E,22E)-(1S,3R,24R)-N,N-dimethyl-1,3,24-trihydroxy-26,27-cyclo-9,10-secocholesta-5,7,10(19),22-tetraene-25-carboxylic acid amide [obtained from the epimer mixture 4a and 4b (Example 1c) by chromatography on silica gel and treatment with tetrabutylammonium fluoride (trihydrate)] in 18 ml of THF is added in drops. After 3 hours at 0° C. in ice-cold ammonium chloride solution, the reaction mixture is stirred in. After extraction with ethyl acetate, drying of the organic phase on sodium sulfate and chromatography on silica gel with ethyl acetate/hexane, the title compound is obtained as a colorless foam.

$^1$H-NMR (300 MHz, CDCl$_3$): δ=0.57 ppm (s, 3H); 0.90 (t, 3H); 1.05 (d, 5H); 3.45 (brs, 1H); 4.11 (m, 1H); 4.23 (m, 1H); 4.43 (m, 1H); 5.00 (brs, 1H); 5.35 (brs, 1H); 5.40 (dd, 1H); 5.56 (dd, 1H); 5.91 (d, 1H); 6.01 (d, 1H); 6.38 (d, 1H); 6.98 (dt, 1H)

EXAMPLE 13

(5Z,7E,22E)-(1S,3R,24R)-25-(1-Oxo-2-hexinyl)-26,27-cyclo-9,10-secocholesta-5,7,10(19),22-tetraene-1,3,24-triol (19b)

5.75 ml of n-butyllithium (1.6 M in hexane) is added in drops to 0.9 ml of 1-pentine in 45 ml of hexane at −5° C. After 1 hour at −5° C., 90 mg of (5Z,7E,22E)-(1S,3R,24R)-N,N-dimethyl-1,3,24-trihydroxy-26,27-cyclo-9,10-secocholesta-5,7,10(19),22-tetraene-25-carboxylic acid amide in 9 ml of THF is added in drops. After 3 hours at 0° C., the reaction mixture is stirred into saturated ammonium chloride solution. After extraction with ethyl acetate, drying of the organic phase on sodium sulfate and chromatography on silica gel with ethyl acetate/hexane, the title compound is obtained as a colorless solid.

$^1$H-NMR (300 MHz, CDCl$_3$): δ=0.57 ppm (s, 3H); 1.00 (m, 6H); 1.10 (m, 2H); 1.45 (m, 2H); 2.32 (t, 4H); 3.12 (brd, 1H); 4.23 (m, 2H); 4.43 (m, 1H); 5.00 (brs, 1H); 5.32 (brs, 1H); 5.37 (dd, 1H); 5.51 (dd, 1H); 6.01 (d, 1H); 6.38 (d, 1H)

EXAMPLE 14

[5Z,7E,22E,25(E)]-(1S,3R,24R)-25-(3-Ethoxy-3-oxo-1-propenyl)-26,27-cyclo-9,10-secocholesta-5,7,10(19),22-tetraene-1,3,24-triol (24b)

a) 2.02 g of (5Z,7E,22E)-(1S,3R,24R)-1,3-bis[[dimethyl(1,1-dimethylethyl)silyl]oxy]-24-hydroxy-26,27-cyclo-9,10-secocholesta-5,7,10(19),22-tetraene-25-carboxylic acid ethyl ester 13b (WO 94/07853) is dissolved in 20 ml of DMF and mixed with 761 mg of imidazole as well as 843 mg of t-butyldimethylsilyl chloride. It is stirred overnight at room temperature and worked up in aqueous form (addition of sodium chloride solution, ethyl acetate extraction, washing of the organic phase with sodium chloride solution, drying on sodium sulfate, concentration by evaporation). By chromatography on silica gel with ethyl acetate/hexane, 2.12 g of (5Z,7E,22E)-(1S,3R,24R)-1,3,24-tris[[dimethyl(1,1-dimethlethyl)silyl]oxy]-26,27-cyclo-9,10-secocholesta-5,7,10(19),22-tetraene-25-carboxylic acid ethyl ester 20b is obtained as a colorless foam.

$^1$H-NMR (300 MHz, CDCl$_3$): δ=0.05 ppm (s, 18H); 0.52 (s, 3H); 0.87 (s, 27H); 1.01 (d, 3H); 1.22 (t, 3H); 4.08 (q, 2H); 4.18 (m, 1H); 4.37 (m, 1H); 4.68 (d, 1H); 4.85 (brs, 1H); 5.08 (brs, 1H); 5.22 (dd, 1H); 5.43 (dd, 1H); 6.00 (d, 1H); 6.22 (d, 1H)

b) 2.10 g of trisilyl ether 20b is dissolved in 15 ml of THF, and 12 ml of DIBAH solution (1 M in toluene) is added in drops at 0° C. It is stirred for 1 more hour at 0° C., and then 4 ml of water is added. The precipitate is removed by filtration, rewashed with ethyl acetate, the organic phase is washed with water, dried on sodium sulfate and concentrated by evaporation. Chromatography on silica gel with ethyl acetate/hexane yields 1.53 g of (5Z,7E,22E)-(1S,3R,24R)-1,3,24-tris[[dimethyl(1,1-dimethylethyl)silyl]oxy]-26,27-cyclo-9,10-secocholesta-5,7,10(19),22-tetraene-25-methanol 21b as a colorless foam.

$^1$H-NMR (300 MHz, CDCl$_3$): δ=0.06 ppm (s, 18H); 0.54 (s, 3H); 0.90 (s, 27H); 1.05 (d, 3H); 3.05 (m, 2H); 3.61 (d, 1H); 4.00 (d, 1H); 4.19 (m, 1H); 4.38 (m, 1H); 4.86 (brs, 1H); 5.08 (brs, 1H); 5.74 (m, 2H); 6.01 (d, 1H); 6.22 (d, 1H)

c) 1.5 g of alcohol 21b is dissolved in 50 ml of methylene chloride and mixed in portions with a total of 1.2 g of pyridinium chlorochromate at room temperature. It is stirred for 3 more hours at room temperature, diluted with ether, filtered, concentrated by evaporation and the residue is chromatographed on silica gel with ethyl acetate/hexane, whereby 570 mg of (5Z,7E,22E)-(1S,3R,24R)-1,3,24-tris[[dimethyl(1,1-dimethylethyl)silyl]oxy]-26,27-cyclo-9,10-secocholesta-5,7,10(19),22-tetraene-25-carbaldehyde 22b is obtained as a colorless foam.

$^1$H-NMR (300 MHz, CDCl$_3$): δ=0.05 ppm (s, 18H); 0.55 (s, 3H); 0.90 (s, 27H); 1.05 (d, 3H); 4.19 (m, 1H); 4.38 (m, 1H); 4.45 (d, 1H); 4.87 (brs, 1H); 5.08 (brs, 1H); 5.32 (dd, 1H); 5.53 (dd, 1H); 6.01 (d, 1H); 6.23 (d, 1H); 9.29 (s, 1H)

d) 34 mg of sodium hydride (65%) in 5 ml of THF is introduced, and 216 mg of diethylphosphonoacetic acid ethyl ester is added. Then, 100 mg of aldehyde 22b in 5 ml of THF is added in drops and heated for 1 hour to 50° C. After cooling, it is worked up in aqueous form analogously to 14a) and chromatographed on silica gel with ethyl acetate/hexane, whereby 100 mg of [5Z,7E,22E,25(E)]-(1S,3R,24R)-25-(3-ethoxy-3-oxo-1-propenyl)-1,3,24-tris[[dimethyl(1,1-dimethylethyl)silyl]oxy]-26,27-cyclo-9,10-secocholesta-5,7,10(19),22-tetraene 23b is obtained as a colorless foam.

$^1$H-NMR (300 MHz, CDCl$_3$): δ=0.06 ppm (s, 18H); 0.53 (s, 3H); 0.89 (s, 27H); 1.02 (d, 3H); 1.25 (t, 3H); 3.89 (d, 1H); 4.16 (q, 2H); 4.18 (m, 1H); 4.38 (m, 1H); 4.85 (brs, 1H); 5.18 (brs, 1H); 5.30 (dd, 1H); 5.41 (dd, 1H); 5.68 (d, 1H); 6.00 (d, 1H); 6.22 (d, 1H); 6.98 (d, 1H)

e) 100 mg of ester 23b is dissolved in 10 ml of THF, 287 mg of tetrabutylammonium fluoride (trihydrate) is added and stirred overnight at room temperature. Analogously to 14a), it is worked up in aqueous form and chromatographed on silica gel with ethyl acetate/hexane, whereby 39 mg of title compound 24b accumulates as a colorless foam.

$^1$H-NMR (300 MHz, CDCl$_3$): δ=0.53 ppm (s, 3H); 1.05 (d, 3H); 1.27 (t, 3H); 3.91 (d, 1H); 4.15 (q, 2H); 4.20 (m, 1H); 4.41 (m, 1H); 4.97 (brs, 1H); 5.30 (brs, 1H); 5.40 (dd, 1H); 5.58 (dd, 1H); 5.79 (d, 1H); 5.99 (d, 1H); 6.37 (d, 1H); 6.93 (d, 1H)

EXAMPLE 15

[5Z,7E,22E,25(E)]-(1S,3R,24S)-25-(3-Ethoxy-3-oxo-1-propenyl)-26,27-cyclo-9,10-secocholesta-5,7,10(19),22-tetraene-1,3,24-triol (24a)

3.1 g of (5Z,7E,22E)-(1S,3R,24S)-1,3-bis[[dimethyl(1,1-dimethylethyl)silyl]oxy]-24-hydroxy-26,27-cyclo-9,10-secocholesta-5,7,10(19),22-tetraene-25-carboxylic acid ethyl ester 13a (WO 94/07853) is reacted to title compound 24a analogously to 14a), b), c), d) and e), which accumulates as a colorless foam.

$^1$H-NMR (300 MHz, CDCl$_3$): δ=0.56 ppm (s, 3H); 1.02 (d, 3H); 1.28 (t, 3H); 3.93 (d, 1H); 4.16 (q, 2H); 4.21 (m, 1H); 4.41 (m, 1H); 4.99 (brs, 1H); 5.31 (brs, 1H); 5.41 (dd, 1H); 5.61 (dd, 1H); 5.80 (d, 1H); 6.00 (d, 1H); 6.38 (d, 1H); 6.93 (d, 1H)

EXAMPLE 16

[5Z,7E,22E,25(E)]-(1S,3R,24R)-25-[3-(1,1-Dimethylethoxy)-3-oxo-1-propenyl]-26,27-cyclo-9,10-secocholesta-5,7,10(19),22-tetraene-1,3,24-triol (26b)

a) Analogously to 14d), aldehyde 22b is reacted with diethylphosphonoacetic acid-t-butyl ester, whereby [5Z,7E,22E,25(E)]-(1S,3R,24R)-25-[3-(1,1-dimethylethoxy)-3-oxo-1-propenyl]-1,3,24-tris-[[dimethyl(1,1-dimethylethyl)silyl]oxy]-26,27-cyclo-9,10-secocholesta-5,7,10(19),22-tetraene 25b accumulates as a colorless foam.

$^1$H-NMR (300 MHz, CDCl$_3$): δ=0.06 ppm (s, 18H); 0.53 (s, 3H); 0.89 (s, 27H); 1.02 (d, 3H); 1.46 (s, 9H); 3.91 (d, 1H); 4.18 (m, 1H); 4.37 (m, 1H); 4.87 (brs, 1H); 5.18 (brs, 1H); 5.29 (dd, 1H); 5.41 (dd, 1H); 5.59 (d, 1H); 6.00 (d, 1H); 6.22 (d, 1H); 6.81 (d, 1H)

b) Analogously to 14e), title compound 26b is obtained as a colorless foam.

$^1$H-NMR (300 MHz, CDCl$_3$): δ=0.58 ppm (s, 3H); 1.06 (d, 3H); 1.47 (s, 9H); 3.39 (dd, 1H); 4.22 (m, 1H); 4.42 (m, 1H); 5.00 (brs, 1H); 5.23 (dd, 1H); 5.31 (sbr, 1H); 5.52 (dd, 1H); 5.68 (d, 1H); 6.01 (d, 1H); 6.38 (d, 1H); 6.79 (d, 1H)

EXAMPLE 17

(5Z,7E,22E)-[1S,3R,24S,25(S)]-25-(1-Hydroxy-2,2,
3,3,4,4,5,5,6,6,7,7,7-tridecafluoroheptyl)-26,27-
cyclo-9,10-secocholesta-5,7,10(19),22-tetraene-1,3,
24-triol (27aα) and (5Z,7E,22E)-[1S,3R,24S,25
(R)]-25-(1-hydroxy-2,2,3,3,4,4,5,5,6,6,7,7,7-
tridecafluoroheptyl)-26,27-cyclo-9,10-secocholesta-
5,7,10(19),22-tetraene-1,3,24-triol (27aβ)

60 mg of aldehyde 22a [synthesis analogous to 22b from 13a instead of 13b, see 14a)–c)] with 107 mg of perfluorohexyl iodide in diethyl ether is introduced at −78° C., and 0.12 ml of methyllithium/lithium bromide complex (1.6 M in ether) is added in drops. After 30 minutes at −78° C., it is worked up in aqueous form analogously to 14a), and the residue is purified by chromatography on silica gel with ethyl acetate/hexane. The product that accumulates (22 mg) is dissolved in 10 ml of THF, mixed with 60 mg of tetrabutylammonium fluoride (trihydrate) and stirred overnight at room temperature. After renewed aqueous working-up, the diastereomeric alcohols are now separated by preparative thin-layer chromatography with ethyl acetate/hexane as mobile solvent, whereby 0.9 mg of title compound 27aα and 2.45 mg of title compound 27aβ accumulate as colorless foams.

$^1$H-NMR (300 MHz, CD$_2$Cl$_2$):

27aα δ=0.54 ppm (s, 3H); 1.00 (d, 3H); 3.35 (dd, 1H); 4.15 (m, 2H); 4.35 (m, 1H); 4.75 (brs, 1H); 4.93 (brs, 1H); 4.97 (d, 1H); 5.08 (dd, 1H); 5.27 (dd, 1H); 5.53 (dd, 1H); 6.00 (d, 1H); 6.34 (d, 1H)

27aβ δ=0.55 ppm (s, 3H); 1.02 (d, 3H); 3.36 (d, 1H); 3.76 (d, 1H); 4.07 (dd, 1H); 4.16 (m, 1H); 4.36 (m, 1H); 4.95 (brs, 1H); 5.18 (brs, 1H); 5.51 (dd, 1H); 5.62 (dd, 1H); 6.00 (d, 1H); 6.35 (d, 1H)

EXAMPLE 18

(5Z,7E,22E)-[1S,3R,24R,25(S)]-25-(1-Hydroxy-2,2,
3,3,4,4,5,5,6,6,7,7,7-tridecafluoroheptyl)-26,27-
cyclo-9,10-secocholesta-5,7,10(19),22-tetraene-1,3,
24-triol (27bα) and (5Z,7E,22E)-[1S,3R,24R,25
(R)]-25-(1-hydroxy-2,2,3,3,4,4,5,5,6,6,7,7,7-
tridecafluoroheptyl)-26,27-cyclo-9,10-secocholesta-
5,7,10(19),22-tetraene-1,3,24-triol (27bβ)

Analogously to 17), 50 mg of aldehyde 22b is reacted, whereby ultimately 4.50 mg of title compound 27bα and 3.15 mg of title compound 27bβ accumlate as colorless foams.

$^1$H-NMR (300 MHz, CD$_2$Cl$_2$):

27bα δ=0.54 ppm (s, 3H); 1.02 (d, 3H); 3.33 (dd, 1H); 4.15 (m, 1H); 4.16 (m, 1H); 4.36 (m, 1H); 4.84 (brs, 1H); 4.95 (brs, 1H); 4.99 (d, 1H); 5.07 (dd, 1H); 5.17 (dd, 1H); 5.51 (dd, 1H); 6.00 (d, 1H); 6.35 (d, 1H)

27bβ δ=0.55 ppm (s, 3H); 1.03 (d, 3H); 3.52 (d, 1H); 3.73 (dd, 1H); 3.98 (s, 1H); 4.17 (m, 2H); 4.36 (m, 1H); 4.95 (brs, 1H); 5.18 (brs, 1H); 5.56 (m, 2H); 6.00 (d, 1H); 6.35 (d, 1H)

EXAMPLE 19

(5Z,7E,22E)-(1S,3R,24R)-25-Acetyl-20-methyl-26,
27-cyclo-9,10-secocholesta-5,7,10(19),22-tetraene-1,
3,24-triol (33b) and (5Z,7E,22E)-(1S,3R,24S)-25-
acetyl-20-methyl-26,27-cyclo-9,10-secocholesta-5,7,
10(19),22-tetraene-1,3,24-triol (33a)

a) Lithium diisopropylamide (LDA) is prepared from 3.4 ml of diisopropylamine and 8.7 ml of n-butyllithium solution (2.5 M in hexane) in 250 ml of THF at 0° C. under argon, and the solution is then cooled to −78° C. 3.5 g of 1-acetylcyclopropanecarboxylic acid methyl ester [D. F. Taber et al. J. Org. Chem. 57, 456 (1992)] is now added in drops and stirred for 1 hour. Then, 3.2 g of (5Z,7E)-(1S, 3R)-1,3-bis[[dimethyl(1,1-dimethylethyl)silyl]oxy]-20-methyl-9,10-secopregna-5,7,10(19)-triene-20-carbaldehyde (WO 93/12081) 28 in 20 ml of THF is added in drops and stirred for 2 hours at 0° C. After saturated ammonium chloride solution is added at −20° C., it is diluted with saturated sodium chloride solution, extracted with ethyl acetate with the addition of 5% oxalic acid, dried on sodium sulfate and concentrated by evaporation. The thus obtained crude product (5Z,7E,22E)-(1S,3R)-1,3-bis[[dimethyl(1,1-dimethylethyl)silyl]oxy]-20-methyl-24-oxo-26,27-cyclo-9,10-secocholesta-5,7,10(19),22-tetraene-25-carboxylic acid 29 (4.3 g of a solid compound) is further reacted without additional purification.

b) An amount of 2.23 g of 29, 990 mg of dicyclohexyl-carbodiimide and 552 mg of N-hydroxysuccinimide are dissolved in 30 ml of methylene chloride and stirred for 2 hours under argon. 0.81 ml of dimethylamine is now added, and the mixture is stirred overnight at room temperature. It is diluted with sodium chloride solution, extracted with methylene chloride, dried on sodium sulfate, the solvent is removed, and the residue is purified by chromatography on silica gel with ethyl acetate/hexane, whereby 1.5 g of (5Z,7E,22E)-(1S,3R)-1,3-bis[[dimethyl(1,1-dimethylethyl)silyl]oxy]-24-oxo-N,N,20-trimethyl-26,27-cyclo-9,10-secocholesta-5,7,10(19),22-tetraene-25-carboxylic acid amide 30 accumulates as a colorless foam.

$^1$H-NMR (300 MHz, CDCl$_3$): δ=0.07 ppm (s, 12H); 0.48 (s, 3H); 0.86 (s, 18H); 1.07 (s, 3H); 1.10 (s, 3H); 2.91 (s, 3H); 2.98 (s, 3H); 4.18 (m, 1H); 4.37 (m, 1H); 4.82 (brs, 1H); 5.18 (brs, 1H); 5.97 (d, 1H); 6.13 (d, 1H); 6.19 (d, 1H); 7.20 (d, 1H)

c) 3.2 g of 30 is reacted analogously to 1b), and, after chromatography on silica gel with ethyl acetate/hexane, 2.7 g of (5Z,7E,22E)-(1S,3R)-1,3-bis[[dimethyl(1,1-dimethylethyl)silyl]oxy]-24-hydroxy-N,N,20-trimethyl-26,27-cyclo-9,10-secocholesta-5,7,10(19),22-tetraene-25-carboxylic acid dimethylamide 31 is obtained as a diastereomer mixture relative to C-24 as a colorless foam.

$^1$H-NMR (300 MHz, CDCl$_3$): δ=0.07 ppm (s, 12H); 0.55 (s, 3H); 0.89 (s, 18H); 1.02/1.03 (2×s, 3H); 1.08/1.09 (2×s, 3H); 3.04 (brs, 6H); 4.02 (m, 1H); 4.19 (m, 1H); 4.39 (m, 1H); 4.87 (brs, 1H); 5.20 (brs, 1H); 5.27 (d, 1H); 5.88 (d, 1H); 6.00 (d, 1H); 6.22 (d, 1H)

d) 300 mg of 31 in 2 ml of diethyl ether is introduced, and 1.03 ml of methyllithium solution (1.3 M in diethyl ether) is added in drops at −78° C. under argon. It is stirred for 30 minutes at −78° C. and for another 30 minutes at −30° C. Then, it is quenched with sodium chloride solution, extracted with ethyl acetate, the combined organic phases are washed with sodium chloride solution, dried on sodium sulfate, and the solvent is removed. Chromatography of the crude product on silica gel with ethyl acetate/hexane yields 165 mg of (5Z,7E,22E)-(1S,3R)-25-acetyl-1,3-bis[[dimethyl(1,1-dimethylethyl)silyl]oxy]-20-methyl-26,27-cyclo-9,10-secocholesta-5,7,10(19),22-tetraen-24-ol 32 as a colorless foam.

$^1$H-NMR (300 MHz, CD$_2$Cl$_2$): δ=0.04 ppm (s, 12H); 0.53 (s, 3H); 0.84 (s, 18H); 1.02/1.03 (2×s, 3H); 1.05/1.06 (2×s, 3H); 1.93/1.94 (2×s, 3H); 2.90/2.94 (2×d, OH); 4.04/4.09 (2×t, 1H); 4.16 (m, 1H); 4.35 (m, 1H); 4.82 (brs, 1H); 5.17 (brs, 1H); 5.29/5.30 (2×dd, 1H); 5.79 (d, 1H); 5.98 (d, 1H); 6.22 (d, 1H)

e) 160 mg of 32 is treated analogously to 1e), and, after chromatography on silica gel with ethyl acetate/hexane as well as diastereomeric separation by HPLC on a chiral phase with hexane/isopropanol/ethanol in succession, 12 mg of 33b and 21 mg of 33a are obtained as colorless foams.

$^1$H-NMR (300 MHz, CD$_2$Cl$_2$):

33b δ=0.56 ppm (s, 3H); 1.02 (s, 3H); 1.07 (s, 3H); 1.95 (s, 3H); 3.00 (d, OH); 4.08 (m, 1H); 4.17 (m, 1H); 4.38 (m, 1H); 4.95 (brs, 1H); 5.29 (brs, 1H); 5.30 (dd, 1H); 5.80 (d, 1H); 5.99 (d, 1H); 6.35 (d, 1H)

33a δ=0.57 ppm (s, 3H); 1.01 (s, 3H); 1.08 (s, 3H); 1.95 (s, 3H); 2.95 (d, OH); 4.13 (m, 1H); 4.16 (m, 1H); 4.38 (m, 1H); 4.96 (brs, 1H); 5.29 (brs, 1H); 5.30 (dd, 1H); 5.82 (d, 1H); 5.99 (d, 1H); 6.35 (d, 1H)

EXAMPLE 20

(5Z,7E,22E)-(1S,3R,24R)-20-Methyl-25-(1-oxobutyl)-26,27-cyclo-9,10-secocholesta-5,7,10(19),22-tetraene-1,3,24-triol (35b) and (5Z,7E,22E)-(1S,3R,24S)-20-methyl-25-(1-oxobutyl)-26,27-cyclo-9,10-secocholesta-5,7,10(19),22-tetraene-1,3,24-triol (35a)

a) 0.9 ml of propyl iodide in 20 ml of diethyl ether is introduced, and 8 ml of t-butyllithium solution (1.5 M in pentane) is added in drops at −78° C. under argon. This mixture is stirred for 30 minutes at −78° C., and then added in drops to a solution of 300 mg of 31 in 2 ml of diethyl ether at −78° C. under argon. It is now stirred for 3 hours at −78° C. and then quenched with sodium chloride solution. It is then extracted with ethyl acetate, the combined organic phases are washed with sodium chloride solution, dried on sodium sulfate, and the solvent is removed. The residue is chromatographed on silica gel with ethyl acetate/hexane, whereby 180 mg of (5Z,7E,22E)-(1S,3R)-1,3-bis[[dimethyl(1,1-dimethylethyl)silyl]oxy]-20-methyl-25-(1-oxobutyl)-26,27-cyclo-9,10-secocholesta-5,7,10(19),22-tetraen-24-ol 34 accumulates as a colorless foam.

$^1$H-NMR (300 MHz, CD$_2$Cl$_2$): δ=0.03 ppm (s, 12H); 0.53 (s, 3H); 0.86 (s, 18H); 0.86 (t, 3H); 1.00/1.01 (2×s, 3H); 1.05/1.06 (2×s, 3H); 2.14 (t, 2H); 3.02/3.07 (2×d, OH); 4.02/4.05 (2×t, 1H); 4.17 (m, 1H); 4.37 (m, 1H); 4.83 (brs, 1H); 5.17 (brs, 1H); 5.29/5.30 (2×dd, 1H); 5.78 (d, 1H); 5.98 (d, 1H); 6.23 (d, 1H)

b) 160 mg of 34 is treated analogously to 1e), and, after chromatography on silica gel with ethyl acetate/hexane as well as diastereomeric separation by HPLC on a chiral phase with hexane/isopropanol/ethanol in succession, 14 mg of 35b and 27 mg of 35a are obtained as colorless foams.

$^1$H-NMR (300 MHz, CD$_2$Cl$_2$):

35b δ=0.55 ppm (s, 3H); 0.88 (t, 3H); 1.02 (s, 3H); 1.07 (s, 3H); 2.14 (t, 2H); 3.10 (brs, OH); 4.05 (m, 1H); 4.17 (m, 1H); 4.38 (m, 1H); 4.95 (brs, 1H); 5.29 (brs, 1H); 5.30 (dd, 1H); 5.79 (d, 1H); 5.99 (d, 1H); 6.35 (d, 1H)

35a δ=0.55 ppm (s, 3H); 0.88 (t, 3H); 1.00 (s, 3H); 1.09 (s, 3H); 2.16 (t, 2H); 3.06 (brs, OH); 4.08 (m, 1H); 4.17 (m, 1H); 4.37 (m, 1H); 4.95 (brs, 1H); 5.29 (brs, 1H); 5.30 (dd, 1H); 5.81 (d, 1H); 5.99 (d, 1H); 6.35 (d, 1H)

EXAMPLE 21

(5Z,7E,22E)-(1S,3R,24R)-20-Methyl-25-(1-oxopentyl)-26,27-cyclo-9,10-secocholesta-5,7,10(19),22-tetraene-1,3,24-triol (37b) and (5Z,7E,22E)-(1S,3R,24S)-20-methyl-25-(1-oxopentyl)-26,27-cyclo-9,10-secocholesta-5,7,10(19),22-tetraene-1,3,24-triol (37a)

a) 250 mg of 31 in 10 ml of THF is introduced under argon and cooled to −78° C. At this temperature, 1 ml of n-butyllithium solution (1.6 M in hexane) is added in drops and stirred for 4 more hours. It is then quenched with sodium chloride solution, extracted with ethyl acetate, dried on sodium sulfate, the solvent is removed, and the residue is chromatographed on silica gel with ethyl acetate/hexane, whereby 160 mg of (5Z,7E,22E)-(1S,3R)-1,3-bis[[dimethyl(1,1-dimethylethyl)silyl]oxy]-20-methyl-25-(1-oxopentyl)-26,27-cyclo-9,10-secocholesta-5,7,10(19),22-tetraen-24-ol 36 is obtained as a colorless foam.

$^1$H-NMR (300 MHz, CDCl$_3$): δ=0.05 ppm (s, 12H); 0.54 (s, 3H); 0.88 (s, 18H); 0.90 (t, 3H); 1.02/1.03 (2×s, 3H); 1.07/1.08 (2×s, 3H); 3.27/3.28 (2×d, OH); 4.08 (m, 1H); 4.20 (m, 1H); 4.38 (m, 1H); 4.87 (brs, 1H); 5.19 (brs, 1H); 5.32/5.33 (2×dd, 1H); 5.80 (d, 1H); 5.99 (d, 1H); 6.22 (d, 1H)

b) 150 mg of 36 is treated analogously to 1e), and, after chromatography on silica gel with ethyl acetate/hexane as well as diastereomeric separation by HPLC on a chiral phase with hexane/isopropanol/ethanol in succession, 12 mg of 37b and 22 mg of 37a are obtained as colorless foams.

$^1$H-NMR (300 MHz, CD$_2$Cl$_2$):

37b δ=0.55 ppm (s, 3H); 0.89 (t, 3H); 1.01 (s, 3H); 1.07 (s, 3H); 2.18 (t, 2H); 3.09 (d, OH); 4.04 (t, 1H); 4.17 (m, 1H); 4.38 (m, 1H); 4.96 (brs, 1H); 5.30 (brs, 1H); 5.31 (dd, 1H); 5.80 (d, 1H); 5.99 (d, 1H); 6.35 (d, 1H)

37a δ=0.56 ppm (s, 3H); 0.88 (t, 3H); 1.00 (s, 3H); 1.08 (s, 3H); 2.19 (t, 2H); 2.99 (d, OH); 4.08 (m, 1H); 4.17 (m, 1H); 4.38 (m, 1H); 4.96 (brs, 1H); 5.30 (brs, 1H); 5.31 (dd, 1H); 5.82 (d, 1H); 5.99 (d, 1H); 6.35 (d, 1H)

EXAMPLE 22

(5Z,7E,22E)-(1S,3R,24R)-20-Methyl-25-(1-oxohexyl)-26,27-cyclo-9,10-secocholesta-5,7,10(19),22-tetraene-1,3,24-triol (39b)

a) Analogously to 20a), 150 mg of 31 is reacted with 1-pentyllithium (that consists of 1-iodopentane and t-butyllithium), whereby 170 mg of (5Z,7E,22E)-(1S,3R)-1,3-bis[[dimethyl(1,1-dimethylethyl)silyl]oxy]-20-methyl-25-(1-oxohexyl)-26,27-cyclo-9,10-secocholesta-5,7,10(19),22-tetraen-24-ol 38 is obtained as a colorless foam. The separation of the diastereomers was carried out by repeated chromatography on aluminum oxide plates with ethyl acetate/hexane. 25 mg of (5Z,7E,22E)-(1S,3R,24R)-1,3-bis[[dimethyl(1,1-dimethylethyl)-silyl]oxy]-20-methyl-25-(1-oxohexyl)-26,27-cyclo-9,10-secocholesta-5,7,10(19),22-tetraen-24-ol 38b and 18 mg of (5Z,7E,22E)-(1S,3R,24S)-1,3-bis[[dimethyl(1,1-dimethylethyl)-silyl]oxy]-20-methyl-25-(1-oxohexyl)-26,27-cyclo-9,10-secocholesta-5,7,10(19),22-tetraen-24-ol 38a were obtained as colorless foams.

$^1$H-NMR (300 MHZ, CDCl$_3$):

38b δ=0.06 ppm (s, 12H); 0.53 (s, 3H); 0.87 (t, 3H); 0.88 (s, 18H); 0.99 (s, 3H); 1.05 (s, 3H); 3.09 (d, OH); 4.02 (t, 1H); 4.18 (m, 1H); 4.39 (m, 1H); 4.83 (brs, 1H); 5.19 (brs, 1H); 5.31 (dd, 1H); 5.79 (d, 1H); 5.99 (d, 1H); 6.22 (d, 1H)

38a δ=0.06 ppm (s, 12H); 0.52 (s, 3H); 0.87 (t, 3H); 0.88 (s, 18H); 0.99 (s, 3H); 1.08 (s, 3H); 3.03 (d, OH); 4.06 (t, 1H); 4.18 (m, 1H); 4.38 (m, 1H); 4.83 (brs, 1H); 5.19 (brs, 1H); 5.30 (dd, 1H); 5.79 (d, 1H); 5.99 (d, 1H); 6.23 (d, 1H)

b) 24 mg of 38b is treated analogously to 1e), and, after chromatography on silica gel with ethyl acetate/hexane, 6 mg of 39b is obtained as a colorless foam.

$^1$H-NMR (300 MHz, CD$_2$Cl$_2$): δ=0.55 ppm (s, 3H); 0.88 (t, 3H); 1.00 (s, 3H); 1.08 (s, 3H); 3.10 (brs, OH); 4.03 (m, 1H); 4.18 (m, 1H); 4.38 (m, 1H); 4.94 (brs, 1H); 5.29 (brs, 1H); 5.29 (dd, 1H); 5.79 (d, 1H); 5.99 (d, 1H); 6.34 (d, 1H)

EXAMPLE 23

(5Z,7E,22E)-(1S,3R,24S)-20-Methyl-25-(1-oxohexyl)-26,27-cyclo-9,10-secocholesta-5,7,10(19),22-tetraene-1,3,24-triol (39a)

17 mg of 38a is treated analogously to 1e), and, after chromatography on silica gel with ethyl acetate/hexane, 5 mg of 39a is obtained as a colorless foam.

$^1$H-NMR (300 MHz, CD$_2$Cl$_2$): δ=0.56 ppm (s, 3H); 0.87 (t, 3H); 1.00 (s, 3H); 1.07 (s, 3H); 3.05 (brs, OH); 4.07 (m, 1H); 4.18 (m, 1H); 4.37 (m, 1H); 4.95 (brs, 1H); 5.29 (brs, 1H); 5.29 (dd, 1H); 5.80 (d, 1H); 5.98 (d, 1H); 6.35 (d, 1H)

EXAMPLE 24

(5Z,7E,22E)-(1S,3R,24R)-20-Methyl-25-(1-oxoheptyl)-26,27-cyclo-9,10-secocholesta-5,7,10(19),22-tetraene-1,3,24-triol (41b) and (5Z,7E,22E)-(1S,3R,24S)-20-methyl-25-(1-oxoheptyl)-26,27-cyclo-9,10-secocholesta-5,7,10(19),22-tetraene-1,3,24-triol (41a)

a) Analogously to 20a), 300 mg of 31 is reacted with 1-hexyllithium (that consists of 1-iodohexane and t-butyllithium), whereby 150 mg of (5Z,7E,22E)-(1S,3R)-1,3-bis[[dimethyl(1,1-dimethylethyl)silyl]oxy]-20-methyl-25-(1-oxoheptyl)-26,27-cyclo-9,10-secocholesta-5,7,10(19),22-tetraen-24-ol 40 in addition to 230 mg of the starting material are obtained as colorless foams.

$^1$H-NMR (300 MHz, CDCl$_3$): δ=0.06 ppm (s, 12H); 0.53 (s, 3H); 0.87 (t, 3H); 0.89 (s, 18H); 1.02/1.03 (2×s, 3H); 1.08/1.09 (2×s, 3H); 3.25/3.29 (2×d, OH); 4.06/4.08 (2×t, 1H); 4.19 (m, 1H); 4.38 (m, 1H); 4.87 (brs, 1H); 5.20 (brs, 1H); 5.32/5.34 (dd, 1H); 5.80 (d, 1H); 5.99 (d, 1H); 6.22 (d, 1H)

b) 145 mg of 40 is treated analogously to 1e), and, after chromatography on silica gel with ethyl acetate/hexane as well as diastereomeric separation by HPLC on a chiral phase with hexane/isopropanol/ethanol in succession, 19 mg of 41b and 11 mg of 41a are obtained as colorless foams.

$^1$H-NMR (300 MHz, CD$_2$Cl$_2$):

41b δ=0.55 ppm (s, 3H); 0.89 (t, 3H); 1.01 (s, 3H); 1.07 (s, 3H); 2.17 (t, 2H); 3.10 (d, OH); 4.03 (t, 1H); 4.17 (m, 1H); 4.38 (m, 1H); 4.95 (brs, 1H); 5.29 (brs, 1H); 5.30 (dd, 1H); 5.79 (d, 1H); 5.99 (d, 1H); 6.35 (d, 1H)

41a δ=0.55 ppm (s, 3H); 0.88 (t, 3H); 1.00 (s, 3H); 1.07 (s, 3H); 2.17 (t, 2H); 3.07 (brs, OH); 4.08 (m, 1H); 4.17 (m, 1H); 4.38 (m, 1H); 4.94 (brs, 1H); 5.28 (brs, 1H); 5.30 (dd, 1H); 5.80 (d, 1H); 5.99 (d, 1H); 6.35 (d, 1H)

EXAMPLE 25

(5Z,7E,22E)-(1S,3R,24R)-20-Methyl-25-(1-oxooctyl)-26,27-cyclo-9,10-secocholesta-5,7,10(19),22-tetraene-1,3,24-triol (43b) and (5Z,7E,22E)-(1S,3R,24S)-20-methyl-25-(1-oxooctyl)-26,27-cyclo-9,10-secocholesta-5,7,10(19),22-tetraene-1,3,24,triol (43a)

a) Analogously to 20a), 300 mg of 31 is reacted with 1-heptyllithium (that consists of 1-iodoheptane and t-butyllithium), whereby 160 mg of (5Z,7E,22E)-(1S,3R)-1,3-bis[[dimethyl(1,1-dimethylethyl)silyl]oxy]-20-methyl-25-(1-oxooctyl)-26,27-cyclo-9,10-secocholesta-5,7,10(19),22-tetraen-24-ol 42 in addition to 210 mg of the starting material are obtained as colorless foams.

$^1$H-NMR (300 MHz, CDCl$_3$): δ=0.06 ppm (s, 12H); 0.52 (s, 3H); 0.88 (t, 3H); 0.89 (s, 18H); 1.00/1.01 (2×s, 3H); 1.05/1.06 (2×s, 3H); 3.21/3.28 (2×d, OH); 4.04/4.07 (2×t, 1H); 4.18 (m, 1H); 4.37 (m, 1H); 4.85 (brs, 1H); 5.18 (brs, 1H); 5.31/5.32 (dd, 1H); 5.79 (d, 1H); 5.98 (d, 1H); 6.21 (d, 1H)

b) 155 mg of 42 is treated analogously to 1e), and, after chromatography on silica gel with ethyl acetate/hexane as well as diastereomeric separation by HPLC on a chiral phase with hexane/isopropanol/ethanol in succession, 31 mg of 43b and 25 mg of 43a are obtained as colorless foams.

$^1$H-NMR (300 MHz, CD$_2$Cl$_2$):

43b δ=0.55 ppm (s, 3H); 0.88 (t, 3H); 1.01 (s, 3H); 1.06 (s, 3H); 2.17 (t, 2H); 3.12 (d, OH); 4.03 (t, 1H); 4.17 (m, 1H); 4.37 (m, 1H); 4.95 (brs, 1H); 5.29 (brs, 1H); 5.32 (dd, 1H); 5.80 (d, 1H); 5.99 (d, 1H); 6.34 (d, 1H)

43a δ=0.54 ppm (s, 3H); 0.87 (t, 3H); 0.99 (s, 3H); 1.07 (s, 3H); 2.17 (t, 2H); 3.04 (brs, OH); 4.07 (m, 1H); 4.17 (m, 1H); 4.37 (m, 1H); 4.95 (brs, 1H); 5.29 (brs, 1H); 5.31 (dd, 1H); 5.80 (d, 1H); 5.99 (d, 1H); 6.34 (d, 1H)

EXAMPLE 26

(7E,22E)-(1R,3R,24R)-25-Acetyl-26,27-cyclo-19-nor-9,10-secocholesta-5,7,22-triene-1,3,24-triol (55b)

a) 6.70 g of [1R-[1α(S*),3aβ,4α,7aα]]-α,7a-dimethyloctahydro-4-[(triethylsilyl)oxy]-1H-inden-1-acetaldehyde 44 [H. H. Inhoffen et al. Chem. Ber. 91, 780 (1958), Chem. Ber. 92, 1772 (1959), W. G. Dauben et al. Tetrahedron Lett. 30, 677 (1989), Triethylsilyl Protective Group at C-4-OH] is reacted analogously to 19a), and 11.6 g of [1R-[1α[R*-(E)],3aβ,4α,7aα]]-1-[4-[7a-methyloctahydro-4-[(triethylsilyl)oxy]-1H-inden-1-yl]-1-oxo-2-pentenyl]cyclopropanecarboxylic acid 45 is obtained as a yellow oil.

b) 15 g of crude product 45 is reacted analogously to 19b), and 11.9 g of [1R-[1α[R*-(E)],3aβ,4α,7aα]]-N,N-dimethyl-1-[4-[7a-methyloctahydro-4-[(triethylsilyl)oxy]-1H-inden-1-yl]-1-oxo-2-pentenyl]cyclopropanecarboxylic acid amide 46 is obtained as a colorless oil.

$^1$H-NMR (300 MHz, CDCl$_3$): δ=0.52 ppm (q, 6H); 0.92 (s, 3H); 0.93 (t, 9H); 2.95 (s, 3H); 3.00 (s, 3H); 4.01 (s, 1H); 6.15 (d, 1H); 6.82 (d, 1H)

c) 11.6 g of 46 is reacted analogously to 1b), and 8.7 g of [1R-[1α[R*-(E)],3aβ,4α,7aα]]-N,N-dimethyl-1-[1-hydroxy-4-[7a-methyloctahydro-4-[(triethylsilyl)oxy]-1H-inden-1-yl]-2-pentenyl]cyclopropanecarboxylic acid amide 47 is obtained as a colorless oil.

$^1$H-NMR (300 MHz, CDCl$_3$): δ=0.54 ppm (q, 6H); 0.89 (s, 3H); 0.94 (t, 9H); 2.62 (brd, OH); 3.04 (brs, 6H); 4.02 (s, 1H); 5.27/5.29 (2×dd, 1H); 5.51/5.54 (2×dd, 1H)

d) 5.34 g of 47 in 70 ml of methylene chloride is stirred with 3.2 ml of dihydropyran and 187 mg of pyridinium-p-toluenesulfonate under argon at room temperature for 3 days. Then, sodium chloride solution is added, extracted with methylene chloride, the combined organic phases are washed with sodium bicarbonate solution and sodium chloride solution, dried on sodium sulfate and liberated of solvent. The residue is chromatographed on silica gel with ethyl acetate/hexane, whereby 4.91 g of [1R-[1α[R*-(E)],3aβ,4α,7aα]]-N,N-dimethyl-1-[4-[7a-methyloctahydro-4-[(triethylsilyl)oxy]-1H-inden-1-yl]-1-[(tetrahydro-2H-pyran-2-yl)oxy]-2-pentenyl]cyclopropanecarboxylic acid amide 48 is obtained as a colorless oil.

e) 5.92 g of 48 is treated analogously to 1e), and 2.99 g of [1R-[1α[R*-(E)],3aβ,4α,7aα]]-N,N-dimethyl-1-[4-(4- hydroxy-7a-methyloctahydro-1H-inden-1-yl)-1-[(tetrahydro-2H-pyran-2-yl)oxy]-2-pentenyl]cyclopropanecarboxylic acid amide 49 is obtained as a colorless oil.

f) 2.67 g of 49 is dissolved in 130 ml of methylene chloride, 1.87 g of pyridinium chlorochromate is added in portions and stirred for 2 hours under argon at room temperature. Then, it is diluted with diethyl ether, filtered, and the solvent is removed. The residue is chromatographed on silica gel with ethyl acetate/hexane, whereby 2.84 g of [1R-[1α[R*-(E)],3aβ,7aα]]-N,N-dimethyl-1-[4-(7a-methyloctahydro-4-oxo-1H-inden-1-yl)-1-[(tetrahydro-2H-pyran-2-yl)oxy]-2-pentenyl]cyclopropanecarboxylic acid amide 50 is obtained as a colorless oil.

g) 1.0 g of (3R-trans)-[2-[3,5-bis[[dimethyl(1,1-dimethylethyl)silyl]oxy]cyclohexylidene]ethyl]diphenylphosphine oxide 51 [H. F. DeLuca et al. Tetrahedron Lett. 32, 7663 (1991)] in 10 ml of THF is dissolved and cooled under argon to −78° C. 2.1 ml of n-butyllithium solution (2.5 M in hexane) is now added in drops and stirred for 5 more minutes. Then, 381 mg of 50 in 7 ml of THF is added and stirred for 30 minutes at −78° C. Then, it is quenched with potassium/sodium tartrate solution, extracted with ethyl acetate, the organic phase is washed with sodium chloride solution, dried on sodium sulfate, and the solvent is removed. The residue is chromatographed on silica gel with ethyl acetate/hexane, whereby 648 mg of (7E,22E)-(1R,3R)-1,3-bis[[dimethyl(1,1-dimethylethyl)silyl]oxy]-N,N-dimethyl-24ξ-[(tetrahydro-2H-pyran-2-yl)oxy]-26,27-cyclo-19-nor-9,10-secocholesta-5,7,22-triene-25-carboxylic acid amide 52 remains as a colorless foam.

h) 350 mg of 52 is dissolved in 5 ml of THF, and 0.64 ml of methyllithium solution (1.3 M in diethyl ether) is added in drops at −78° C. under argon. After 90 minutes, it is quenched with sodium chloride solution, extracted with ethyl acetate, the organic phase is washed with sodium chloride solution, dried on sodium sulfate, and the solvent is removed. The residue is chromatographed on silica gel with ethyl acetate/hexane, whereby 284 mg of (7E,22E)-(1R,3R)-25-acetyl-1,3-bis[[dimethyl(1,1-dimethylethyl)silyl]oxy]-24ξ-[(tetrahydro-2H-pyran-2-yl)oxy]-26,27-cyclo-19-nor-9,10-secocholesta-5,7,22-triene 53 remains as a colorless foam.

i) 279 mg of 53 is dissolved in 37 ml of methylene chloride and treated at −25° C. under argon with 0.74 ml of dimethylaluminum chloride solution (1 M in hexane). It is stirred for 10 hours at this temperature, and the batch is optionally put overnight in a freezer. Then, it is hydrolyzed with sodium bicarbonate solution, extracted with methylene chloride, the organic phase is washed with sodium chloride solution, dried on sodium sulfate, the solvent is removed, and the residue is chromatographed on silica gel with ethyl acetate/hexane. The separation of the diastereomeric alcohols (relative to C-24) was carried out on aluminum oxide plates with ethyl acetate/hexane. Thus, 69 mg of (7E,22E)-(1R,3R,24S)-25-acetyl-1,3-bis[[dimethyl(1,1-dimethylethyl)silyl]oxy]-26,27-cyclo-19-nor-9,10-secocholesta-5,7,22-trien-24-ol 54a in addition to 36 mg of (7E,22E)-(1R,3R,24R)-25-acetyl-1,3-bis[[dimethyl(1,1-dimethylethyl)silyl]oxy]-26,27-cyclo-19-nor-9,10-secocholesta-5,7,22-trien-24-ol 54b are obtained as colorless foams.

$^1$H-NMR (300 MHz, CD$_2$Cl$_2$):

54a δ=0.05 ppm (s, 12H); 0.52 (s, 3H); 0.85 (s, 18H); 1.01 (d, 3H); 1.93 (s, 3H); 2.89 (d, OH); 4.07 (m, 2H); 4.16 (t, 1H); 5.34 (dd, 1H); 5.52 (dd, 1H); 5.80 (d, 1H); 6.16 (d, 1H)

54b δ=0.05 ppm (s, 12H); 0.52 (s, 3H); 0.85 (s, 18H); 1.02 (d, 3H); 1.93 (s, 3H); 2.95 (d, OH); 4.06 (m, 3H); 5.33 (dd, 1H); 5.46 (dd, 1H); 5.80 (d, 1H); 6.16 (d, 1H)

j) 36 mg of 54b is treated analogously to 1e), and, after chromatography on silica gel with ethyl acetate/hexane, 20 mg of 55b is obtained as a colorless foam.

$^1$H-NMR (300 MHz, CD$_2$Cl$_2$/CD$_3$OD): δ=0.53 ppm (s, 3H); 1.01 (s, 3H); 1.98 (s, 3H); 3.94 (m, 1H); 4.01 (m, 1H); 4.15 (m, 1H); 5.29 (dd, 1H); 5.47 (dd, 1H); 5.83 (d, 1H); 6.23 (d, 1H)

EXAMPLE 27

(7E,22E)-(1R,3R,24S)-25-Acetyl-26,27-cyclo-19-nor-9,10-secocholesta-5,7,22-triene-1,3,24-triol (55a)

a) 69 mg of 54a is treated analogously to 1e), and, after chromatography on silica gel with ethyl acetate/hexane, 25 mg of 55a is obtained as a colorless foam.

$^1$H-NMR (300 MHz, CD$_2$Cl$_2$/CD$_3$OD): δ=0.53 ppm (s, 3H); 0.99 (s, 3H); 1.98 (s, 3H); 3.96 (m, 1H); 4.01 (m, 1H); 4.20 (t, 1H); 5.30 (dd, 1H); 5.50 (dd, 1H); 5.83 (d, 1H); 6.23 (d, 1H)

EXAMPLE 28

(7E,22E)-(1R,3R,24R)-25-(1-Oxopentyl)-26,27-cyclo-19-nor-9,10-secocholesta-5,7,22-triene-1,3,24-triol (58b)

a) 420 mg of 52 is treated analogously to 21a), and, after chromatography on silica gel with ethyl acetate/hexane, 250 mg of (7E,22E)-(1R,3R)-1,3-bis[[dimethyl(1,1-dimethylethyl)silyl]oxy]-25-(1-oxopentyl)-24ξ-[(tetrahydro-2H-pyran-2-yl)oxy]-26,27-cyclo-19-nor-9,10-secocholesta-5,7,22-triene 56 is obtained as a colorless foam.

b) 232 mg of 56 is treated analogously to 26i), and, after chromatography on silica gel with ethyl acetate/hexane together, 64 mg of (7E,22E)-(1R,3R,24S)-1,3-bis[[dimethyl(1,1-dimethylethyl)silyl]oxy]-25-(1-oxopentyl)-26,27-cyclo-19-nor-9,10-secocholesta-5,7,22-trien-24-ol 57a in addition to 42 mg of (7E,22E)-(1R,3R,24R)-1,3-bis[[dimethyl(1,1-dimethylethyl)silyl]oxy]-25-(1-oxopentyl)-26,27-cyclo-19-nor-9,10-secocholesta-5,7,22-trien-24-ol 57b are obtained as colorless foams.

$^1$H-NMR (300 MHz, CD$_2$Cl$_2$):

57a δ=0.04 ppm (s, 12H); 0.52 (s, 3H); 0.85 (s, 18H); 0.87 (t, 3H); 1.01 (d, 3H); 3.00 (d, OH); 4.04 (m, 2H); 4.12 (t, 1H); 5.32 (dd, 1H); 5.51 (dd, 1H); 5.81 (d, 1H); 6.15 (d, 1H)

57b δ=0.04 ppm (s, 12H); 0.52 (s, 3H); 0.85 (s, 18H); 0.87 (t, 3H); 1.01 (d, 3H); 3.05 (d, OH); 4.05 (m, 3H); 5.34 (dd, 1H); 5.44 (dd, 1H); 5.81 (d, 1H); 6.15 (d, 1H)

c) 41 mg of 57b is treated analogously to 1e), and 15 mg of 58b is obtained as a colorless foam.

$^1$H-NMR (300 MHz, CD$_2$Cl$_2$/CD$_3$OD): δ=0.52 ppm (s, 3H); 0.89 (t, 3H); 1.00 (d, 3H); 2.27 (t, 2H); 3.95 (m, 1H); 4.03 (m, 1H); 4.17 (t, 1H); 5.31 (dd, 1H); 5.48 (dd, 1H); 5.82 (d, 1H); 6.22 (d, 1H)

EXAMPLE 29

(7E,22E)-(1R,3R,24S)-25-(1-Oxopentyl)-26,27-cyclo-19-nor-9,10-secocholesta-5,7,22-triene-1,3,24-triol (58a)

62 mg of 57a is treated analogously to 1e), and 27 mg of 58a is obtained as a colorless foam.

¹H-NMR (300 MHz, CD$_2$Cl$_2$/CD$_3$OD): δ=0.51 ppm (s, 3H); 0.87 (t, 3H); 0.99 (d, 3H); 2.23 (t, 2H); 3.95 (m, 1H); 4.02 (m, 1H); 4.19 (t, 1H); 5.32 (dd, 1H); 5.50 (dd, 1H); 5.82 (d, 1H); 6.23 (d, 1H)

EXAMPLE 30

(7E,22E)-(1R,3R,24R)-25-(1-Oxohexyl)-26,27-cyclo-19-nor-9,10-secocholesta-5,7,22-triene-1,3,24-triol (61b)

a) Analogously to 20a), 500 mg of 52 is reacted with 1-pentyllithium (that consists of 1-iodopentane and t-butyllithium), whereby after chromatography with ethyl acetate/hexane, 321 mg of (7E,22E)-(1R,3R)-1,3-bis[[dimethyl(1,1-dimethylethyl)silyl]oxy]-25-(1-oxohexyl)-24ξ-[(tetrahydro-2H-pyran-2-yl)oxy]-26,27-cyclo-19-nor-9,10-secocholesta-5,7,22-triene 59 is obtained as a colorless foam.

b) 213 mg of 59 is treated analogously to 26i), and, after chromatography on silica gel with ethyl acetate/hexane together, 81 mg of (7E,22E)-(1R,3R,24S)-1,3-bis[[dimethyl(1,1-dimethylethyl)silyl]oxy]-25-(1-oxohexyl)-26,27-cyclo-19-nor-9,10-secocholesta-5,7,22-trien-24-ol 60a in addition to 42 mg of (7E,22E)-(1R,3R,24R)-1,3-bis[[dimethyl(1,1-dimethylethyl)silyl]oxy]-25-(1-oxohexyl)-26,27-cyclo-19-nor-9,10-secocholesta-5,7,22-trien-24-ol 60b are obtained as colorless foams.

₁H-NMR (300 MHz, CD$_2$Cl$_2$):

60a δ=0.04 ppm (s, 12H); 0.52 (s, 3H); 0.86 (s, 18H); 0.87 (t, 3H); 1.01 (d, 3H); 2.15 (t, 2H); 3.01 (d, OH); 4.05 (m, 2H); 4.12 (t, 1H); 5.33 (dd, 1H); 5.51 (dd, 1H); 5.81 (d, 1H); 6.15 (d, 1H)

60b δ=0.04 ppm (s, 12H); 0.52 (s, 3H); 0.86 (s, 18H); 0.87 (t, 3H); 1.02 (d, 3H); 2.15 (t, 2H); 3.07 (d, OH); 4.02 (t, 1H); 4.06 (m, 2H); 5.34 (dd, 1H); 5.44 (dd, 1H); 5.81 (d, 1H); 6.15 (d, 1H)

c) 51 mg of 60b is treated analogously to 1e), and 27 mg of 61b is obtained as a colorless foam.

¹H-NMR (300 MHz, CD$_2$Cl$_2$): δ=0.54 ppm (s, 3H); 0.87 (t, 3H); 1.02 (d, 3H); 2.16 (t, 2H); 3.11 (d, OH); 3.95 (m, 1H); 4.03 (m, 1H); 4.05 (t, 1H); 5.34 (dd, 1H); 5.46 (dd, 1H); 5.83 (d, 1H); 6.24 (d, 1H)

EXAMPLE 31

(7E,22E)-(1R,3R,24S)-25-(1-Oxohexyl)-26,27-cyclo-19-nor-9,10-secocholesta-5,7,22-triene-1,3,24-triol (61a)

63 mg of 60a is treated analogously to 1e), and 32 mg of 61a is obtained as a colorless foam.

¹H-NMR (300 MHz, CD$_2$Cl$_2$): δ=0.54 ppm (s, 3H); 0.87 (t, 3H); 1.01 (d, 3H); 2.16 (t, 2H); 3.04 (d, OH); 3.95 (m, 1H); 4.03 (m, 1H); 4.13 (t, 1H); 5.34 (dd, 1H); 5.51 (dd, 1H); 5.83 (d, 1H); 6.24 (d, 1H)

EXAMPLE 32

(7E,22E)-(1R,3R,24R)-25-(1-Oxoheptyl)-26,27-cyclo-19-nor-9,10-secocholesta-5,7,22-triene-1,3,24-triol (64b)

a) Analogously to 20a), 500 mg of 52 is reacted with 1-hexyllithium (that consists of 1-iodohexane and t-butyllithium), whereby after chromatography with ethyl acetate/hexane, 255 mg of (7E,22E)-(1R,3R)-1,3-bis[[dimethyl(1,1-dimethylethyl)silyl]oxy]-25-(1-oxoheptyl)-24ξ-[(tetrahydro-2H-pyran-2-yl)oxy]-26,27-cyclo-19-nor-9,10-secocholesta-5,7,22-triene 62 is obtained as a colorless foam.

b) 190 mg of 62 is treated analogously to 26i), and, after chromatography on silica gel with ethyl acetate/hexane together, 53 mg of (7E,22E)-(1R,3R,24S)-1,3-bis[[dimethyl(1,1-dimethylethyl)silyl]oxy]-25-(1-oxoheptyl)-26,27-cyclo-19-nor-9,10-secocholesta-5,7,22-trien-24-ol 63a in addition to 29 mg of (7E,22E)-(1R,3R,24R)-1,3-bis[[dimethyl(1,1-dimethylethyl)silyl]oxy]-25-(1-oxoheptyl)-26,27-cyclo-19-nor-9,10-secocholesta-5,7,22-trien-24-ol 63b are obtained as colorless foams.

¹H-NMR (300 MHz, CD$_2$Cl$_2$):

63a δ=0.03 ppm (s, 12H); 0.53 (s, 3H); 0.85 (s, 18H); 0.87 (t, 3H); 1.01 (d, 3H); 2.16 (t, 2H); 3.00 (d, OH); 4.05 (m, 2H); 4.12 (t, 1H); 5.32 (dd, 1H); 5.51 (dd, 1H); 5.81 (d, 1H); 6.14 (d, 1H)

63b δ=0.03 ppm (s, 12H); 0.53 (s, 3H); 0.85 (s, 18H); 0.87 (t, 3H); 1.02 (d, 3H); 2.16 (t, 2H); 3.05 (d, OH); 4.03 (t, 1H); 4.05 (m, 2H); 5.34 (dd, 1H); 5.44 (dd, 1H); 5.81 (d, 1H); 6.14 (d, 1H)

c) 29 mg of 63b is treated analogously to 1e), and 17 mg of 64b is obtained as a colorless foam.

¹H-NMR (300 MHz, CD$_2$Cl$_2$): δ=0.53 ppm (s, 3H); 0.88 (t, 3H); 1.03 (d, 3H); 2.17 (t, 2H); 3.12 (d, OH); 3.98 (m, 1H); 4.05 (m, 1H); 4.08 (t, 1H); 5.35 (dd, 1H); 5.48 (dd, 1H); 5.84 (d, 1H); 6.26 (d, 1H)

EXAMPLE 33

(7E,22E)-(1R,3R,24S)-25-(1-Oxoheptyl)-26,27-cyclo-19-nor-9,10-secocholesta-5,7,22-triene-1,3,24-triol (64a)

52 mg of 63a is treated analogously to 1e), and 27 mg of 64a is obtained as a colorless foam.

¹H-NMR (300 MHz, CD$_2$Cl$_2$): δ=0.53 ppm (s, 3H); 0.88 (t, 3H); 1.02 (d, 3H); 2.16 (t, 2H); 3.08 (d, OH); 3.98 (m, 1H); 4.05 (m, 1H); 4.12 (t, 1H); 5.33 (dd, 1H); 5.51 (dd, 1H); 5.84 (d, 1H); 6.27 (d, 1H)

EXAMPLE 34

(7E,22E)-(1R,3R,24R)-25-(1-Oxooctyl)-26,27-cyclo-19-nor-9,10-secocholesta-5,7,22-triene-1,3,24-triol (67b)

a) Analogously to 20a), 380 mg of 52 is reacted with 1-heptyllithium (that consists of 1-iodoheptane and t-butyllithium), whereby after chromatography with ethyl acetate/hexane, 224 mg of (7E,22E)-(1R,3R)-1,3-bis[[dimethyl(1,1-dimethylethyl)silyl]oxy]-25-(1-oxooctyl)-24ξ-[(tetrahydro-2H-pyran-2-yl)oxy]-26,27-cyclo-19-nor-9,10-secocholesta-5,7,22-triene 65 is obtained as a colorless foam.

b) 103 mg of 65 is treated analogously to 26i), and, after chromatography on silica gel with ethyl acetate/hexane together, 28 mg of (7E,22E)-(1R,3R,24S)-1,3-bis[[dimethyl(1,1-dimethylethyl)silyl]oxy]-25-(1-oxooctyl)-26,27-cyclo-19-nor-9,10-secocholesta-5,7,22-trien-24-ol 66a in addition to 24 mg of (7E,22E)-(1R,3R,24R)-1,3-Bis[[dimethyl(1,1-dimethylethyl)silyl]oxy]-25-(1-oxooctyl)-26,27-cyclo-19-nor-9,10-secocholesta-5,7,22-trien-24-ol 66b are obtained as colorless foams.

¹H-NMR (300 MHz, CD$_2$Cl$_2$):

66a δ=0.04 ppm (s, 12H); 0.53 (s, 3H); 0.85 (s, 18H); 0.86 (t, 3H); 1.00 (d, 3H); 2.17 (t, 2H); 3.01 (d, OH); 4.06 (m, 2H); 4.12 (t, 1H); 5.32 (dd, 1H); 5.51 (dd, 1H); 5.80 (d, 1H); 6.14 (d, 1H)

66b δ=0.04 ppm (s, 12H); 0.53 (s, 3H); 0.85 (s, 18H); 0.86 (t, 3H); 1.02 (d, 3H); 2.15 (t, 2H); 3.05 (d, OH); 4.02 (t, 1H); 4.06 (m, 2H); 5.35 (dd, 1H); 5.45 (dd, 1H); 5.80 (d, 1H); 6.14 (d, 1H)

c) 24 mg of 66b is treated analogously to 1e), and 10 mg of 67b is obtained as a colorless foam.

$^1$H-NMR (300 MHz, CD$_2$Cl$_2$): δ=0.53 ppm (s, 3H); 0.87 (t, 3H); 1.01 (d, 3H); 2.17 (t, 2H); 3.08 (brs, OH); 3.98 (m, 1H); 4.06 (m, 2H); 5.36 (dd, 1H); 5.48 (dd, 1H); 5.83 (d, 1H); 6.27 (d, 1H)

EXAMPLE 35

(7E,22E)-(1R,3R,24S)-25-(1-Oxooctyl)-26,27-cyclo-19-nor-9,10-secocholesta-5,7,22-triene-1,3,24-triol (67a)

38 mg of 66a is treated analogously to 1e), and 13 mg of 67a is obtained as a colorless foam.

$^1$H-NMR (300 MHz, CD$_2$Cl$_2$): δ=0.53 ppm (s, 3H); 0.85 (t, 3H); 1.00 (d, 3H); 2.15 (t, 2H); 3.00 (brs, OH); 3.97 (m, 1H); 4.06 (m, 1H); 4.11 (t, 1H); 5.35 (dd, 1H); 5.50 (dd, 1H); 5.83 (d, 1H); 6.26 (d, 1H)

EXAMPLE 36

(7E,22E)-(1R,3R,24R)-25-(1-Oxononyl)-26,27-cyclo-19-nor-9,10-secocholesta-5,7,22-triene-1,3,24-triol (70b)

a) Analogously to 20a), 375 mg of 52 is reacted with 1-octyllithium (that consists of 1-iodooctane and t-butyllithium), whereby after chromatography with ethyl acetatehexane, 212 mg of (7E,22E)-(1R,3R)-1,3-bis[[dimethyl(1,1-dimethylethyl)silyl]oxy]-25-(1-oxononyl)-24ξ-[(tetrahydro-2H-pyran-2-yl)oxy]-26,27-cyclo-19-nor-9,10-secocholesta-5,7,22-triene 68 is obtained as a colorless foam.

b) 125 mg of 68 is treated analogously to 26i), and, after chromatography on silica gel with ethyl acetate/hexane together, 36 mg of (7E,22E)-(1R,3R,24S)-1,3-bis[[dimethyl(1,1-dimethylethyl)silyl]oxy]-25-(1-oxononyl)-26,27-cyclo-19-nor-9,10-secocholesta-5,7,22-trien-24-ol 69a in addition to 24 mg of (7E,22E)-(1R,3R,24R)-1,3-bis[[dimethyl(1,1-dimethylethyl)silyl]oxy]-25-(1-oxononyl)-26,27-cyclo-19-nor-9,10-secocholesta-5,7,22-trien-24-ol 69b are obtained as colorless foams.

$^1$H-NMR (300 MHz, CD$_2$Cl$_2$):

69a δ=0.05 ppm (s, 12H); 0.52 (s, 3H); 0.85 (s, 18H); 0.86 (t, 3H); 1.01 (d, 3H); 2.16 (t, 2H); 3.02 (d, OH); 4.05 (m, 2H); 4.12 (t, 1H); 5.32 (dd, 1H); 5.51 (dd, 1H); 5.80 (d, 1H); 6.14 (d, 1H)

69b δ=0.05 ppm (s, 12H); 0.53 (s, 3H); 0.85 (s, 18H); 0.86 (t, 3H); 1.02 (d, 3H); 2.16 (t, 2H); 3.05 (d, OH); 4.02 (t, 1H); 4.05 (m, 2H); 5.34 (dd, 1H); 5.45 (dd, 1H); 5.80 (d, 1H); 6.14 (d, 1H)

c) 36 mg of 69b is treated analogously to 1e), and 17 mg of 70b is obtained as a colorless foam.

$^1$H-NMR (300 MHz, CD$_2$Cl$_2$): δ=0.54 ppm (s, 3H); 0.87 (t, 3H); 1.02 (d, 3H); 2.16 (t, 2H); 3.08 (brs, OH); 3.98 (m, 1H); 4.05 (m, 2H); 5.35 (dd, 1H); 5.48 (dd, 1H); 5.83 (d, 1H); 6.28 (d, 1H)

EXAMPLE 37

(7E,22E)-(1R,3R,24S)-25-(1-Oxononyl)-26,27-cyclo-19-nor-9,10-secocholesta-5,7,22-triene-1,3,24-triol (70a)

24 mg of 69a is treated analogously to 1e), and 8 mg of 70a is obtained as a colorless foam.

$^1$H-NMR (300 MHz, CD$_2$Cl$_2$): δ=0.54 ppm (s, 3H); 0.87 (t, 3H); 1.02 (d, 3H); 2.17 (t, 2H); 3.07 (d, OH); 3.98 (m, 1H); 4.05 (m, 1H); 4.12 (t, 1H); 5.34 (dd, 1H); 5.51 (dd, 1H); 5.83 (d, 1H); 6.28 (d, 1H)

EXAMPLE 38

(7E,22E)-(1R,3R,24S)-25-Acetyl-20-methyl-26,27-cyclo-19-nor-9,10-secocholesta-5,7,22-triene-1,3,24-triol (81a) and (7E,22E)-(1R,3R,24R)-25-acetyl-20-methyl-26,27-cyclo-19-nor-9,10-secocholesta-5,7,22-triene-1,3,24-triol (81b)

a) 1.8 g of sodium hydride (55% in mineral oil) in 105 ml of THF is introduced under argon, and a solution of 10.8 g of [1R-[1α(S*),3aβ,4α,7aα]]-α,7a-dimethyloctahydro-4-[(triethylsilyl)oxy]-1H-inden-1-acetaldehyde 44 [H. H. Inhoffen et al. Chem. Ber. 91, 780 (1958), Chem. Ber. 92, 1772 (1959), W. G. Dauben et al. Tetrahedron Lett. 30, 677 (1989), Triethylsilyl Protective Group at C-4-OH] in 45 ml of THF is added in drops. Then, 6.24 ml of iodomethane is added in drops, and the mixture is stirred overnight at room temperature. The reaction mixture is now carefully poured into ice water and extracted with ethyl acetate. The combined organic phases are washed with sodium chloride solution, dried on sodium sulfate, the solvent is removed, and the residue is chromatographed on silica gel with ethyl acetate/hexane, whereby 7.52 g of [1S-(1α,3aβ,4α,7aα)]-octahydro-4-[(triethylsilyl)oxy]-α,α,7a-trimethyl-1H-inden-1-acetaldehyde 71.

$^1$H-NMR (300 MHz, CDCl$_3$): δ=0.57 ppm (q, 6H); 0.97 (t, 9H); 0.98 (s, 3H); 1.10 (s, 3H); 1.12 (s, 3H); 4.05 (m, 1H); 9.68 (s, 1H)

b) 7.5 g of 71 is reacted analogously to 19a), and 14.6 g of [1R-[1α(E),3aβ,4α,7aα]]-1-[4-methyl-4-[7a-methyloctahydro-4-[(triethylsilyl)oxy]-1H-inden-1-yl]-1-oxo-2-pentenyl]cyclopropanecarboxylic acid 72 is obtained as a yellowish oil.

c) 12.9 g of 72 is reacted analogously to 19b), and 5.8 g of [1R-[1α(E),3aβ,4α,7aα]]-N,N-dimethyl-1-[4-methyl-4-[7a-methyloctahydro-4-[(triethylsilyl)oxy]-1H-inden-1-yl]-1-oxo-2-pentenyl]cyclopropanecarboxylic acid amide 73 is obtained as a colorless oil.

$^1$H-NMR (300 MHz, CDCl$_3$): δ=0.54 ppm (q, 6H); 0.92 (t, 9H); 0.93 (s, 3H); 1.03 (s, 3H); 1.10 (s, 3H); 2.94 (s, 3H); 2.99 (s, 3H); 4.01 (m, 1H); 6.15 (d, 1H); 7.22 (d, 1H)

d) 1.02 g of 73 is reacted analogously to 1b), and 743 mg of [1R-[1α(E),3aβ,4α,7aα]]-N,N-dimethyl-1-[1-hydroxy-4-methyl-4-[7a-methyloctahydro-4-[(triethylsilyl)oxy]-1H-inden-1-yl]-2-pentenyl]cyclopropanecarboxylic acid amide 74 is obtained as a colorless oil.

$^1$H-NMR (300 MHz, CDCl$_3$): δ=0.54 ppm (q, 6H); 0.92 (t, 9H); 0.94 (s, 3H); 1.00/1.01 (2×s, 3H); 1.05, 1.06 (2×s, 3H); 3.03 (br s, 3H); 4.00 (m, 1H); 4.05 (m, 1H); 5.22 (d, 1H); 5.89 (d, 1H)

e) 1.01 g of 74 is treated analogously to 26d), and 938 mg of [1R-[1α(E),3aβ,4α,7aα]]-N,N-dimethyl-1-[4-methyl-4-[7a-methyloctahydro-4-[(triethylsilyl)oxy]-1H-inden-1-yl]-1-[(tetrahydro-2H-pyran-2-yl)oxy]-2-pentenyl]cyclopropanecarboxylic acid amide 75 is obtained as a colorless oil.

f) 1.64 g of 75 is treated analogously to 1e), and 1.08 g of [1R-[1α(E),3aβ,4α,7aα]]-N,N-dimethyl-1-[4-(4-hydroxy-7a-methyloctahydro-1H-inden-1-yl)-4-methyl-1-[(tetrahydro-2H-pyran-2-yl)oxy]-2-pentenyl]cyclopropanecarboxylic acid amide 76 is obtained as a colorless oil.

g) 1.07 g of 76 is treated analogously to 26f), whereby 920 mg of [1R-[1α(E),3aβ,7aα]]-N,N-dimethyl-1-[4-methyl-4-(7a-methyloctahydro-4-oxo-1H-inden-1-yl)-1-[(tetrahydro-2H-pyran-2-yl)oxy]-2-pentenyl]cyclopropanecarboxylic acid amide 77 is obtained as a colorless foam.

h) Analogously to 26g), 583 mg of 77 is reacted with 1.5 g of (3R-trans)-[2-[3,5-bis[[dimethyl(1,1-dimethylethyl)silyl]oxy]cyclohexylidene]ethyl]diphenylphosphine oxide 51, and, after chromatographic purification on silica gel with hexane/ethyl acetate, 1.02 g of (7E,22E)-(1R,3R)-1,3-bis[[dimethyl(1,1-dimethylethyl)silyl]oxy]-24ξ-[(tetrahydro-2H-pyran-2-yl)oxy]-N,N-20-trimethyl-26,27-cyclo-19-nor-9,10-secocholesta-5,7,22-triene-25-carboxylic acid amide 78 is obtained as a colorless foam.

g) 254 mg of 78 is reacted with methyllithium analogously to 26h), and 136 mg of (7E,22E)-(1R,3R)-25-acetyl-1,3-bis[[dimethyl(1,1-dimethylethyl)silyl]oxy]-20-methyl-24ξ-[(tetrahydro-2H-pyran-2-yl)oxy]-26,27-cyclo-19-nor-9,10-secocholesta-5,7,22-triene 79 is obtained as a colorless foam.

h) 135 mg of 79 is treated analogously to 26i), and 51 mg of (7E,22E)-(1R,3R)-25-acetyl-1,3-bis[[dimethyl(1,1-dimethylethyl)silyl]oxy]-20-methyl-26,27-cyclo-19-nor-9,10-secocholesta-5,7,22-trien-24-ol 80 is obtained as a colorless foam.

$^1$H-NMR (300 MHz, CDCl$_3$): δ=0.05 ppm (s, 12H); 0.54 (s, 3H); 0.87 (s, 18H); 1.01/1.02 (2×s, 3H); 1.07/1.08 (2×s, 3H); 1.96/1.97 (2×s, 3H); 3.11/3.15 (m, OH); 4.08 (m, 3H); 5.32/5.34 (2×dd, 1H); 5.78 (d, 1H); 5.82 (d, 1H); 6.15 (d, 1H)

i) 50 mg of 80 is treated analogously to 1e), and, after chromatography on silica gel with ethyl acetate/hexane as well as diastereomeric separation by HPLC on a chiral phase with hexane/isopropanol/ethanol in succession, 4 mg of 81b and 5 mg of 81a are obtained as colorless foams.

$^1$H-NMR (300 MHz, CD$_2$Cl$_2$):

81b δ=0.55 ppm (s, 3H); 1.02 (s, 3H); 1.08 (s, 3H); 1.95 (s, 3H); 3.98 (m, 1H); 4.07 (m, 1H); 4.08 (d, 1H); 5.31 (dd, 1H); 5.80 (d, 1H); 5.82 (d, 1H); 6.28 (d, 1H)

81a δ=0.55 ppm (s, 3H); 1.01 (s, 3H); 1.08 (s, 3H); 1.96 (s, 3H); 2.94 (brs, OH); 3.99 (m, 1H); 4.08 (m, 1H); 4.12 (d, 1H); 5.31 (dd, 1H); 5.82 (d, 1H); 5.82 (d, 1H); 6.28 (d, 1H)

EXAMPLE 39

(7E,22E)-(1R,3R,24S)-20-Methyl-25-(1-oxopentyl-26,27-(cyclo-19-nor-9,10-secocholesta-5,7,22-triene-1,3,24-triol (84a) and (7E,22E)-(1R,3R,24R)-20-methyl-25-(1-oxopentyl)-26,27-cyclo-19-nor-9,10-secocholesta-5,7,22-triene-1,3,24-triol (84b)

a) 250 mg of 78 is reacted analogously to 21a), and, after chromatography on silica gel with ethyl acetate/hexane, 200 mg of (7E,22E)-(1R,3R)-1,3-bis[[dimethyl(1,1-dimethylethyl)silyl]oxy]-20-methyl-25-(1-oxopentyl)-24ξ-[(tetrahydro-2H-pyran-2-yl)oxy]-26,27-cyclo-19-nor-9,10-secocholesta-5,7,22-triene 82 is obtained as a colorless foam.

b) 195 mg of 82 is treated analogously to 26i), and 89 mg of (7E,22E)-(1R,3R)-1,3-bis[[dimethyl(1,1-dimethylethyl)silyl]oxy]-20-methyl-25-(1-oxopentyl)-26,27-cyclo-19-nor-9,10-secocholesta-5,7,22-trien-24-ol 83 is obtained as a colorless foam.

$^1$H-NMR (300 MHz, CDCl$_3$): δ=0.06 ppm (s, 12H); 0.55 (s, 3H); 0.88 (s, 18H); 0.90 (t, 3H); 1.01/1.02 (2×s, 3H); 1.07/1.08 (2×s, 3H); 2.14/2.15 (2×t, 2H); 3.23/3.29 (2×d, OH); 4.08 (m, 3H); 5.33/5.34 (2×dd, 1H); 5.79 (d, 1H); 5.82 (d, 1H); 6.16 (d, 1H)

c) 85 mg of 83 is treated analogously to 1e), and, after chromatography on silica gel with ethyl acetate/hexane as well as diastereomeric separation by HPLC on a chiral phase with hexane/isopropanol/ethanol in succession, 12 mg of 84b and 16 mg of 84a are obtained as colorless foams.

$^1$H-NMR (300 MHz, CD$_2$Cl$_2$):

84b δ=0.55 ppm (s, 3H); 0.91 (t, 3H); 1.03 (s, 3H); 1.09 (s, 3H); 2.20 (t, 2H); 3.09 (d, OH); 4.00 (m, 1H); 4.07 (m, 2H); 5.31 (dd, 1H); 5.82 (d, 1H); 5.83 (d, 1H); 6.28 (d, 1H)

84a δ=0.55 ppm (s, 3H); 0.91 (t, 3H); 1.02 (s, 3H); 1.10 (s, 3H); 2.20 (t, 2H); 3.09 (d, OH); 4.00 (m, 1H); 4.08 (m, 1H); 4.10 (m, 1H); 5.31 (dd, 1H); 5.82 (d, 1H); 5.82 (d, 1H); 6.28 (d, 1H)

EXAMPLE 40

(7E,22E)-(1R,3R,24S)-20-Methyl1-25-(1-oxohexyl)-26,27-cyclo-19-nor-9,10-secocholesta-5,7,22-triene-1,3,24-triol (87a) and (7E,22E)-(1R,3R,24R)-20-methyl-25-(1-oxohexyl)-26,27-cyclo-19-nor-9,10-secocholesta-5,7,22-triene-1,3,24-triol (87b)

a) 250 mg of 78 is reacted analogously to 20a) with 1-pentyllithium (that consists of 1-iodopentane and t-butyllithium), and, after chromatography on silica gel with ethyl acetate/hexane, 192 mg of (7E,22E)-(1R,3R)-1,3-bis[[dimethyl(1,1-dimethylethyl)silyl]oxy]-20-methyl-25-(1-oxohexyl)-24ξ-[(tetrahydro-2H-pyran-2-yl)oxy]-26,27-cyclo-19-nor-9,10-secocholesta-5,7,22-triene 85 is obtained as a colorless foam.

b) 187 mg of 85 is treated analogously to 26i), and 91 mg of (7E,22E)-(1R,3R)-1,3-bis[[dimethyl(1,1-dimethylethyl)silyl]oxy]-20-methyl-25-(1-oxohexyl)-26,27-cyclo-19-nor-9,10-secocholesta-5,7,22-trien-24-ol 86 is obtained as a colorless foam.

$^1$H-NMR (300 MHz, CDCl$_3$): δ=0.06 ppm (s, 12H); 0.55 (s, 3H); 0.88 (s, 18H); 0.89 (t, 3H); 1.01/1.02 (2×s, 3H); 1.07/1.08 (2×s, 3H); 2.14/2.15 (2×t, 2H); 3.25/3.30 (2×d, OH); 4.08 (m, 3H); 5.34/5.35 (2×dd, 1H); 5.79 (d, 1H); 5.80 (d, 1H); 6.17 (d, 1H)

c) 91 mg of 86 is treated analogously to 1e), and, after chromatography on silica gel with ethyl acetate/hexane as well as diastereomeric separation by HPLC on a chiral phase with hexane/isopropanol/ethanol in succession, 12 mg of 87b and 13 mg of 87a are obtained as colorless foams.

$^1$H-NMR (300 MHz, CD$_2$Cl$_2$):

87b δ=0.53 ppm (s, 3H); 0.87 (t, 3H); 1.01 (s, 3H); 1.07 (s, 3H); 2.17 (t, 2H); 3.12 (d, OH); 3.97 (m, 1H); 4.03 (m, 2H); 5.30 (dd, 1H); 5.78 (d, 1H); 5.80 (d, 1H); 6.26 (d, 1H)

87a δ=0.53 ppm (s, 3H); 0.87 (t, 3H); 0.99 (s, 3H); 1.06 (s, 3H); 2.16 (t, 2H); 3.07 (d, OH); 3.96 (m, 1H); 4.07 (m, 2H); 5.30 (dd, 1H); 5.79 (d, 1H); 5.80 (d, 1H); 6.26 (d, 1H)

EXAMPLE 41

(7E,22E)-(1R,3R,24S)-20-Methyl-25-(1-oxoheptyl)-26,27-cyclo-19-nor-9,10-secocholesta-5,7,22-triene-1,3,24-triol (90a) and (7E,22E)-(1R,3R,24R)-20-methyl-25-(1-oxoheptyl)-26,27-cyclo-19-nor-9,10-secocholesta-5,7,22-triene-1,3,24-triol (90b)

a) 250 mg of 78 is reacted with 1-hexyllithium (that consists of 1-iodohexane and t-butyllithium) analogously to 20a), and, after chromatography on silica gel with ethyl acetate/hexane, 174 mg of (7E,22E)-(1R,3R)-1,3-bis

[[dimethyl(1,1-dimethylethyl)silyl]oxy]-20-methyl-25-(1-oxoheptyl)-24ξ-[(tetrahydro-2H-pyran-2-yl)oxy]-26,27-cyclo-19-nor-9,10-secocholesta-5,7,22-triene 88 is obtained as a colorless foam.

b) 169 mg of 88 is treated analogously to 26i), and 68 mg of (7E,22E)-(1R,3R)-1,3-bis[[dimethyl(1,1-dimethylethyl)silyl]oxy]-20-methyl-25-(1-oxoheptyl)-26,27-cyclo-19-nor-9,10-secocholesta-5,7,22-trien-24-ol 89 is obtained as a colorless foam.

$^1$H-NMR (300 MHz, CDCl$_3$): δ=0.06 ppm (s, 12H); 0.56 (s, 3H); 0.88 (s, 18H); 0.89 (t, 3H); 1.01/1.02 (2×s, 3H); 1.07/1.08 (2×s, 3H); 2.14/2.15 (2×t, 2H); 3.25/3.30 (2×d, OH); 4.08 (m, 3H); 5.33/5.34 (2×dd, 1H); 5.79 (d, 1H); 5.81 (d, 1H); 6.17 (d, 1H)

c) 66 mg of 89 is treated analogously to 1e), and, after chromatography on silica gel with ethyl acetate/hexane as well as diastereomeric separation by HPLC on a chiral phase with hexane/isopropanol/ethanol in succession, 8 mg of 90b and 11 mg of 90a are obtained as colorless foams.

$^1$H-NMR (300 MHz, CD$_2$Cl$_2$):

90b δ=0.54 ppm (s, 3H); 0.88 (t, 3H); 1.01 (s, 3H); 1.07 (s, 3H); 2.17 (t, 2H); 3.11 (brs, OH); 3.97 (m, 1H); 4.04 (m, 2H); 5.30 (dd, 1H); 5.78 (d, 1H); 5.80 (d, 1H); 6.26 (d, 1H)

90a δ=0.54 ppm (s, 3H); 0.88 (t, 3H); 1.02 (s, 3H); 1.08 (s, 3H); 2.17 (t, 2H); 3.06 (d, OH); 3.97 (m, 1H); 4.05 (m, 1H); 4.06 (m, 1H); 5.30 (dd, 1H); 5.79 (d, 1H); 5.80 (d, 1H); 6.26 (d, 1H)

EXAMPLE 42

(7E,22E)-(1R,3R,24S)-20-Methyl-25-(1-oxooctyl)-26,27-cyclo-19-nor-9,10-secocholesta-5,7,22-triene-1,3,24-triol (93a) and (7E,22E)-(1R,3R,24R)-20-methyl-25-(1-oxooctyl)-26,27-cyclo-19-nor-9,10-secocholesta-5,7,22-triene-1,3,24-triol (93b)

a) 250 mg of 78 is reacted with 1-heptyllithium (that consists of 1-iodoheptane and t-butyllithium) analogously to 20a), and, after chromatography on silica gel with ethyl acetate/hexane, 191 mg of (7E,22E)-(1R,3R)-1,3-bis[[dimethyl(1,1-dimethylethyl)silyl]oxy]-20-methyl-25-(1-oxooctyl)-24ξ-[(tetrahydro-2H-pyran-2-yl)oxy]-26,27-cyclo-19-nor-9,10-secocholesta-5,7,22-triene 91 is obtained as a colorless foam.

b) 186 mg of 91 is treated analogously to 26i), and 67 mg of (7E,22E)-(1R,3R)-1,3-bis[[dimethyl(1,1-dimethylethyl)silyl]oxy]-20-methyl-25-(1-oxooctyl)-26,27-cyclo-19-nor-9,10-secocholesta-5,7,22-trien-24-ol 92 is obtained as a colorless foam.

$^1$H-NMR (300 MHz, CDCl$_3$): δ=0.06 ppm (s, 12H); 0.55 (s, 3H); 0.88 (s, 18H); 0.89 (t, 3H); 1.01/1.02 (2×s, 3H); 1.07/1.08 (2×s, 3H); 2.14/2.15 (2×t, 2H); 3.25/3.30 (2×d, OH); 4.08 (m, 3H); 5.34/5.35 (2×dd, 1H); 5.80 (d, 1H); 5.80 (d, 1H); 6.16 (d, 1H)

c) 65 mg of 92 is treated analogously to 1e), and, after chromatography on silica gel with ethyl acetate/hexane as well as diastereomeric separation by HPLC on a chiral phase with hexane/isopropanol/ethanol in succession, 6 mg of 93b and 8 mg of 93a are obtained as colorless foams.

$^1$H-NMR (300 MHz, CD$_2$Cl$_2$):

93b δ=0.54 ppm (s, 3H); 0.88 (t, 3H); 1.02 (s, 3H); 1.06 (s, 3H); 2.17 (t, 2H); 3.11 (brs, OH); 3.98 (m, 1H); 4.03 (m, 2H); 5.30 (dd, 1H); 5.79 (d, 1H); 5.80 (d, 1H); 6.26 (d, 1H)

93a δ=0.54 ppm (s, 3H); 0.88 (t, 3H); 1.01 (s, 3H); 1.07 (s, 3H); 2.17 (t, 2H); 3.07 (d, OH); 3.97 (m, 1H); 4.08 (m, 2H); 5.30 (dd, 1H); 5.80 (d, 1H); 5.80 (d, 1H); 6.26 (d, 1H)

EXAMPLE 43

(5Z,7E,22E)-[1S,3R,25(S)]-1,3-Dihydroxy-25-(1-hydroxy-2,2,3,3,4,4,5,5,5-nonafluoropentyl)-26,27-cyclo-9,10-secocholesta-5,7,10(19),22-tetraen-24-one (106a) and (5Z,7E,22E)-[1S,3R,25(R)]-1,3-dihydroxy-25-(1-hydroxy-2,2,3,3,4,4,5,5,5-nonafluoropentyl)-26,27-cyclo-9,10-secocholesta-5,7,10(19),22-tetraen-24-one (106b)

a) 18.7 g of 1-(1-oxoethyl)cyclopropanecarboxylic acid methyl ester 94 [D. F. Taber et al. J. Org. Chem. 57, 436 (1992)] in 500 ml of benzene is dissolved, 30 ml of ethylene glycol and 500 mg of p-toluenesulfonic acid are added and heated to boiling in a water separator for 12 hours under argon. After cooling, the organic phase is washed with sodium bicarbonate solution and sodium chloride solution, dried on sodium sulfate, and the solvent is removed. The residue is distilled in a vacuum, whereby 18.6 g of 1-(2-methyl-1,3-dioxolan-2-yl)cyclopropanecarboxylic acid methyl ester 95 accumulates as a colorless oil (boiling point: 90° C., 1 mbar).

$^1$H-NMR (300 MHz, CDCl$_3$): δ=1.02 ppm (m, 2H); 1.16 (m, 2H); 1.61 (s, 3H); 3.69 (s, 3H); 3.92 (m, 4H)

b) 24 g of 95 in 700 ml of toluene is dissolved, cooled to 0° C. under argon, and then 620 ml of DIBAH solution (1.2 M in toluene) is added in drops. It is stirred for 2 hours at this temperature, and then 15 ml of isopropanol and 150 ml of water are added and allowed to stir overnight. Then, it is filtered, thoroughly rewashed with toluene, the organic phase is dried on sodium sulfate, and the solvent is removed. The product 1-(2-methyl-1,3-dioxolan-2-yl)cyclopropanemethanol 96 (yellowish oil) is directly further reacted.

$^1$H-NMR (300 MHz, CDCl$_3$): δ=0.47 ppm (m, 2H); 0.72 (m, 2H); 1.41 (s, 3H); 2.92 (t, OH); 3.53 (d, 2H); 3.97 (m, 4H)

c) 10 g of 96 in 500 ml of methylene chloride is dissolved, and 3.7 g of sodium acetate (anhydrous) and 19.3 g of pyridinium chlorochromate are added. It is now stirred for 2 hours under argon. It is diluted with 1 l of diethyl ether and then filtered on Celite. Concentration by evaporation of the solvent followed by chromatographic purification on silica gel with ethyl acetate/hexane yields 8.1 g of 1-(2-methyl-1,3-dioxolan-2-yl)cyclopropanecarbaldehyde 97 as a colorless oil.

$^1$H-NMR (300 MHz, CDCl$_3$): δ=1.16 ppm (m, 4H); 1.57 (s, 3H); 3.97 (m, 4H); 9.49 (s, 1H)

d) 1.2 g of 97 and 3.92 ml of perfluorobutyl iodide in 40 ml of diethyl ether are introduced under argon and methyllithium/lithium bromide complex (1.5 M in diethyl ether) is added in drops at −78° C. After 30 minutes, it is quenched with sodium chloride solution and diluted with ethyl acetate. Extraction with ethyl acetate, washing of the combined organic phases with sodium chloride solution, drying on sodium sulfate, removal of the solvent and chromatography on silica gel with ethyl acetate/hexane yields 2.1 g of 1-(2-methyl-1,3-dioxolan-2-yl)-α-(1,1,2,2,3,3,4,4,4-nonafluorobutyl)cyclopropanemethanol 98 as a colorless oil.

$^1$H-NMR (300 MHz, CDCl$_3$): δ=0.80 ppm (m, 1H); 0.97 (m, 1H); 1.22 (m, 2H); 1.38 (s, 3H); 3.80 (d, 1H); 3.98 (s, 4H)

e) 3.2 g of 98 in 50 ml of methylene chloride/methanol 1:1 is dissolved, and 750 mg of p-toluenesulfonic acid is added. It is stirred under argon for 2 hours at room temperature.

Sodium chloride solution is added, extracted with methylene chloride, the organic phase is washed with sodium bicarbonate solution and sodium chloride solution, dried on sodium sulfate and concentrated by evaporation. The residue is chromatographed on silica gel with ethyl acetate/hexane, whereby 2.7 g of 1-[1-(1-hydroxy-2,2,3,3,4,4,5,5,5-nonafluoropentyl)cyclopropyl]ethanone 99 is obtained as a colorless oil.

$^1$H-NMR (300 MHz, CDCl$_3$): δ=1.24 ppm (m, 2H); 1.57 (m, 2H); 1.95 (s, 3H); 3.80 (ddd, 1H); 5.01 (d, OH)

f) 7.5 g of (5E,7E)-(1S,3R)-1,3-bis[[dimethyl(1,1-dimethylethyl)silyl]oxy]-9,10-secopregna-5,7,10(19)-triene-20-carbaldehyde 100 [M. J. Calverley Tetrahedron 43, 4609 (1987)] in 200 ml of toluene is dissolved, 2 g of anthracene and 0.5 ml of triethylamine are added and irradiated with nitrogen passing through in a pyrex apparatus with a mercury high-pressure lamp for 30 minutes. Then, it is filtered, concentrated by evaporation, and the residue is chromatographed on silica gel with ethyl acetate/hexane, whereby 7.1 g of (5Z,7E)-(1S,3R)-1,3-bis[[dimethyl(1,1-dimethylethyl)silyl]oxy]-9,10-secopregna-5,7,10(19)-triene-20-carbaldehyde 101 is obtained as a colorless foam.

$^1$H-NMR (300 MHz, CDCl$_3$): δ=0.05 ppm (m, 12H); 0.55 (s, 3H); 0.88 (s, 18H); 1.11 (d, 3H); 2.37 (m, 1H); 4.18 (m, 1H); 4.37 (m, 1H); 4.84 (brs, 1H); 5.17 (brs, 1H); 6.00 (d, 1H); 6.22 (1H); 9.58 (d, 1H)

g) Lithium diisopropylamide is produced from 5.0 ml of diisopropylamine and 12 ml of n-butyllithium solution (2.5 M in hexane) in 60 ml of THF under argon, and 4 g of 99 in 10 ml of THF is added in drops. After 30 minutes at this temperature, 3.5 g of 101 in 5 ml of THF is added in drops, and stirring is continued for 2 hours. It is quenched with sodium chloride solution, extracted with ethyl acetate, the organic phase is washed with sodium chloride solution, dried on sodium sulfate, and the solvent is removed. Chromatography on silica gel with ethyl acetate/hexane yields 2.9 g of (5Z,7E)-(1S,3R)-1,3-bis[[dimethyl(1,1-dimethylethyl)silyl]oxy]-22-hydroxy-25-(1-hydroxy-2,2,3,3,4,4,5,5,5-nona-fluoropentyl)-26,27-cyclo-9,10-secocholesta-5,7,10(19)-trien-24-one 102 as a colorless foam.

h) A mixture of 1.3 g of 102, 3.8 ml of triethylamine, 2.1 ml of acetic anhydride and a spatula-tip full of DMAP in 50 ml of methylene chloride are stirred for 2 hours under argon at room temperature. Then, saturated sodium bicarbonate solution is added and stirred for 30 more minutes. Extraction with ethyl acetate, washing of the organic phase with sodium bicarbonate solution and sodium chloride solution, drying on sodium sulfate, concentration by evaporation and chromatography on silica gel with ethyl acetate/hexane yield 850 mg of (5Z,7E)-(1S,3R)-22-(acetyloxy)-25-[1-(acetyloxy)-2,2,3,3,4,4,5,5,5-nonafluoropentyl]-1,3-bis[[dimethyl(1,1-dimethylethyl)silyl]oxy]-26,27-cyclo-9,10-secocholesta-5,7,10(19)-trien-24-one 103.

i) 850 mg of 103 is dissolved in 5 ml of toluene and mixed with 8 ml of diazabicycloundecane (DBU). It is stirred for 1 hour at 40° C., then diluted with ethyl acetate, and the organic phase is washed with dilute hydrochloric acid as well as sodium bicarbonate solution and sodium chloride solution. Drying on sodium sulfate, concentration by evaporation and chromatography on silica gel with ethyl acetate/hexane yield 460 mg of (5Z,7E,22E)-(1S,3R)-25-[1-(acetyloxy)-2,2,3,3,4,4,5,5,5-nonafluoropentyl]-1,3-bis[[dimethyl(1,1-dimethylethyl)silyl]oxy]-26,27-cyclo-9,10-secocholesta-5,7,10(19),22-tetraen-24-one 104.

j) 110 mg of 104 in 5 ml of methanol is dissolved, 83 mg of potassium carbonate is added and stirred for 1 hour at room temperature under argon. Then, sodium chloride solution is added, extracted with ethyl acetate, washed with sodium chloride solution, dried on sodium sulfate, concentrated by evaporation and chromatographed on silica gel with ethyl acetate/hexane, whereby 39 mg of (5Z,7E,22E)-(1S,3R)-1,3-bis[[dimethyl(1,1-dimethylethyl)silyl]oxy]-25-(1-hydroxy-2,2,3,3,4,4,5,5,5-nonafluoropentyl)-26,27-cyclo-9,10-secocholesta-5,7,10(19),22-tetraen-24-one 105 accumulates as a colorless foam.

k) A mixture of 35 mg of 105 and 350 mg of Dowex ion exchanger (acidic, pretreated with hydrochloric acid and methanol) in 10 ml of methylene chloride/methanol (1:9) is stirred under argon overnight. It is filtered, thoroughly rewashed with ethyl acetate, then the organic phase is washed with sodium bicarbonate solution as well as sodium chloride solution, dried on sodium sulfate, concentrated by evaporation and chromatographed on silica gel with ethyl acetate/hexane, whereby 12 mg of 106a and 9 mg of 106b are obtained in succession as colorless foams.

$^1$H-NMR (300 MHz, CD$_2$Cl$_2$):

106a δ=0.58 ppm (s, 3H); 1.08 (d, 3H); 3.63 (m, 1H); 4.17 (m, 1H); 4.38 (m, 1H); 4.97 (s, 1H); 5.19 (d, OH); 5.30 (m, 1H); 5.83 (d, 1H); 6.01 (d, 1H); 6.37 (1H); 6.92 (dd, 1H)

106b δ=0.50 ppm (s, 3H); 0.99 (d, 3H); 3.63 (m, 1H); 4.17 (m, 1H); 4.38 (m, 1H); 4.97 (s, 1H); 5.18 (d, OH); 5.30 (m, 1H); 5.89 (d, 1H); 6.01 (d, 1H); 6.37 (1H); 6.97 (dd, 1H)

EXAMPLE 44

(5Z,7E,22E)-(3S,24R)-25-(1-Oxopentyl)-26,27-cyclo-9,10-secocholesta-5,7,10(19),22-tetraene-3,24-diol (113b)

a) 5 g of (5E,7E)-(3S)-3-[[dimethyl(1,1-dimethylethyl)silyl]oxy]-9,10-secopregna-5,7,10(19)-triene-20-carbaldehyde 107 [for production, see M. J. Calverley Tetrahedron 43, 4609 (1987), Verzicht auf die Stufen zur 1α-Funktionalisierung [Elimination of Steps to 1α-Functionalization]] is subjected to the procedure described in 43f), and, after chromatography on silica gel with ethyl acetate/hexane, 4.2 g of (5Z,7E)-(3S)-3-[[dimethyl(1,1-dimethylethyl)silyl]oxy]-9,10-secopregna-5,7,10(19)-triene-20-carbaldehyde 108 is obtained as a colorless foam.

$^1$H-NMR (300 MHz, CDCl$_3$): δ=0.08 ppm (s, 6H); 0.60 (s, 3H); 0.89 (d, 9H); 1.14 (d, 3H); 3.83 (m, 1H); 4.78 (s, 1H); 5.01 (s, 1H); 6.03 (d, 1H); 6.18 (d, 1H); 9.59 (s, 1H)

b) Analogously to 19a), 4.2 g of 108 is reacted, whereby 5.3 g of the crude product (5Z,7E,22E)-(3S)-3-[[dimethyl(1,1-dimethylethyl)silyl]oxy]-24-oxo-26,27-cyclo-9,10-secocholesta-5,7,10(19),22-tetraene-25-carboxylic acid 109 is obtained as a yellowish oil.

c) Analogously to 19b), 2.5 g of 109 is reacted, and, after chromatography with ethyl acetate/hexane on silica gel, 1.5 g of (5Z,7E,22E)-(3S)-N,N-dimethyl-3-[[dimethyl(1,1-dimethylethyl)silyl]oxy]-24-oxo-26,27-cyclo-9,10-secocholesta-5,7,10(19),22-tetraene-25-carboxylic acid amide 110 is obtained as a colorless foam.

$^1$H-NMR (300 MHz, CDCl$_3$): δ=0.06 ppm (s, 6H); 0.55 (s, 3H); 0.87 (d, 9H); 1.07 (d, 3H); 2.94 (s, 3H); 2.99 (s, 3H); 3.80 (m, 1H); 4.75 (s, 1H); 4.99 (s, 1H); 5.98 (d, 1H); 6.13 (d, 1H); 6.18 (d, 1H); 6.84 (dd, 1H)

d) 3.16 g of 110 is reacted analogously to 1b), and, after chromatography on silica gel with ethyl acetate/hexane, 2.06 g of (5Z,7E,22E)-(3S)-N,N-dimethyl-3-[[dimethyl(1,1-dimethylethyl)silyl]oxy]-24-hydroxy-26,27-cyclo-9,10- secocholesta-5,7,10(19),22-tetraene-25-carboxylic acid amide 111 is obtained as a colorless foam.

$^1$H-NMR (300 MHz, CDCl$_3$): δ=0.05 ppm (s, 6H); 0.53 (s, 3H); 0.88 (d, 9H); 1.02 (d, 3H); 3.04 (brs, 6H); 3.80 (m, 1H); 4.00 (m, 1H); 4.77 (s, 1H); 5.00 (s, 1H); 5.30/5.32 (2×dd, 1H); 5.55/5.57 (2×dd, 1H); 5.99 (d, 1H); 6.14 (d, 1H)

e) 200 mg of 111 is reacted with n-butyllithium analogously to 21a), and, after chromatography on silica gel with ethyl acetate/hexane, 132 mg of the diastereomeric mixture relative to C-24, which is separated by repeated chromatography on aluminum oxide plates with ethyl acetate/hexane in 60 mg of (5Z,7E,22E)-(3S,24S)-3-[[dimethyl(1,1-dimethylethyl)silyl]oxy]-25-(1-oxopentyl)-26,27-cyclo-9,10-secocholesta-5,7,10(19),22-tetraen-24-ol 112a, as well as 42 mg of (5Z,7E,22E)-(3S,24R)-3-[[dimethyl(1,1-dimethylethyl)silyl[oxy]-25-(1-oxopentyl)-26,27-cyclo-9,10-secocholesta-5,7,10(19),22-tetraen-24-ol 112b are obtained.

$^1$H-NMR (300 MHz, CD$_2$Cl$_2$):

112a δ=0.04 ppm (s, 6H); 0.52 (s, 3H); 0.85 (d, 9H); 0.86 (t, 3H); 1.00 (d, 3H); 2.15 (t, 2H); 3.20 (d, OH); 3.81 (m, 1H); 4.10 (t, 1H); 4.72 (s, 1H); 4.99 (s, 1H); 5.30 (dd, 1H); 5.50 (dd, 1H); 5.98 (d, 1H); 6.14 (d, 1H)

112b δ=0.04 ppm (s, 6H); 0.52 (s, 3H); 0.85 (d, 9H); 0.86 (t, 3H); 1.01 (d, 3H); 2.14 (t, 2H); 3.04 (d, OH); 3.81 (m, 1H); 4.03 (t, 1H); 4.72 (s, 1H); 4.99 (s, 1H); 5.33 (dd, 1H); 5.44 (dd, 1H); 5.98 (d, 1H); 6.14 (d, 1H)

f) 42 mg of 112b is treated analogously to 1e), and, after chromatography on silica gel with ethyl acetate/hexane, 18 mg of 113b is obtained.

$^1$H-NMR (300 MHz, CD$_2$Cl$_2$): δ=0.53 ppm (s, 3H); 0.88 (t, 3H); 2.18 (t, 2H); 3.10 (brs, OH); 3.88 (m, 1H); 4.05 (m, 1H); 4.79 (s, 1H); 5.03 (s, 1H); 5.34 (dd, 1H); 5.48 (dd, 1H); 6.01 (d, 1H); 6.22 (d, 1H)

EXAMPLE 45

(5Z,7E,22E)-(3S,24S)-25-(1-Oxopentyl)-26,27-cyclo-9,10-secocholesta-5,7,10(19),22-tetraene-3,24-diol (113a)

60 mg of 112a is treated analogously to 1e), and, after chromatography on silica gel with ethyl acetate/hexane, 22 mg of 113a is obtained.

$^1$H-NMR (300 MHz, CD$_2$Cl$_2$): δ=0.54 ppm (s, 3H); 0.88 (t, 3H); 2.18 (t, 2H); 3.05 (d, OH); 3.88 (m, 1H); 4.13 (m, 1H); 4.78 (s, 1H); 5.03 (s, 1H); 5.33 (dd, 1H); 5.52 (dd, 1H); 6.01 (d, 1H); 6.22 (d, 1H)

EXAMPLE 46

[5Z,7E,22E,25(E)]-(1S,3R,24S)-25-[3-(1,1-Dimethylethoxy)-3-oxo-1-propenyl]-24-methoxy-26,27-cyclo-9,10-secocholesta-5,7,10(19),22-tetraene-1,3-diol (114a) and [5Z,7E,22E,25(E)]-(1S,3R,24R)-25-[3-(1,1-dimethylethoxy)-3-oxo-1-propenyl]-24-methoxy-26,27-cyclo-9,10-secocholesta-5,7,10(19),22-tetraene-1,3-diol (114b)

260 mg of 25b (see 16a) in 20 ml of methylene chloride/methanol (1:9) is dissolved, 2 g of Dowex-WX8 ion exchanger (acidic) is added and stirred under argon at room temperature for 3 days. Then, it is filtered, concentrated by evaporation and chromatographed on silica gel with ethyl acetate/hexane. The residue is separated via HPLC on a chiral phase with hexane/isopropanol/ethanol, whereby 6 mg of 114a in addition to 5 mg of 114b accumulated as colorless foams.

$^1$H-NMR (300 MHz, CDCl$_3$):

114a: δ=0.57 ppm (s, 3H); 1.05 (d, 3H); 1.47 (s, 9H); 3.30 (s, 3H); 3.40 (d, 1H); 4.22 (m, 1H); 4.43 (m, 1H); 5.00 (s, 1H); 5.23 (dd, 1H); 5.32 (s, 1H); 5.52 (dd, 1H); 5.68 (d, 1H); 6.02 (d, 1H); 6.38 (d, 1H); 6.79 (d, 1H)

114b: δ=0.57 ppm (s, 3H); 1.07 (d, 3H); 1.48 (s, 9H); 3.28 (s, 3H); 3.38 (d, 1H); 4.23 (m, 1H); 4.44 (m, 1H); 5.00 (s, 1H); 5.23 (dd, 1H); 5.32 (s, 1H); 5.51 (dd, 1H); 5.68 (d, 1H); 6.02 (d, 1H); 6.38 (d, 1H); 6.79 (d, 1H)

EXAMPLE 47

(5Z,7E,22E)-(1S,3R,24R)-25-Hydroxymethyl-26,27-cyclo-9,10-secocholesta-5,7,10(19),22-tetraene-1,3,24-triol (115b)

100 mg of 21b is treated (see 14b) analogously to 1e), and, after chromatography on silica gel with ethyl acetate/hexane, 36 mg of 115b is obtained as a colorless foam.

$^1$H-NMR (300 MHz, CDCl$_3$): δ=0.57 ppm (s, 3H); 1.06 (d, 3H); 3.32 (dd, 1H); 3.84 (br s, OH); 3.88 (dd, 1H); 4.23 (m, 1H); 4.43 (m, 1H); 5.00 (s, 1H); 5.32 (s, 1H); 5.47 (dd, 1H); 5.57 (dd, 1H); 6.02 (d, 1H); 6.38 (d, 1H)

EXAMPLE 48

[5Z,7E,22E,25(E)]-(1S,3R,24R)-25-(3-Oxo-1-heptenyl)-26,27-cyclo-9,10-secocholesta-5,7,10(19),22-tetraene-1,3,24-triol (117b)

a) 70 mg of aldehyde 22b is reacted, analogously to 14d), with (2-oxohexyl)-phosphonic acid dimethyl ester [P. Mathey Tetrahedron 34, 649 (1978)] and sodium hydride, and, after chromatography on silica gel with ethyl acetate/hexane, 59 mg of [5Z,7E,22E,25(E)]-(1S,3R,24R)-25-(3-oxo-1-heptenyl)-1,3,24-tris[[dimethyl(1,1-dimethylethyl)silyl]oxy]-26,27-cyclo-9,10-secocholesta-5,7,10(19),22-tetraene 116b is obtained as a colorless foam.

$^1$H-NMR (300 MHz, CDCl$_3$): δ=0.06 ppm (s, 18H); 0.55 (s, 3H); 0.90 (s, 27H); 0.92 (t, 3H); 1.05 (d, 3H); 2.50 (t, 2H); 3.85 (d, 1H); 4.20 (m, 1H); 4.38 (m, 1H); 4.88 (s, 1H); 5.18 (s, 1H); 5.33 (dd, 1H); 5.47 (dd, 1H); 5.97 (d, 1H); 6.02 (d, 1H); 6.23 (d, 1H); 6.93 (d, 1H)

b) 45 mg of 116b is treated analogously to 1e), and, after chromatography on silica gel with ethyl acetate/hexane, 12 mg of 117b is obtained.

$^1$H-NMR (300 MHz, CDCl$_3$): δ=0.58 ppm (s, 3H); 0.92 (t, 3H); 1.07 (d, 3H); 2.50 (t, 2H); 3.94 (d, 1H); 4.23 (m, 1H); 4.43 (m, 1H); 5.00 (brs, 1H); 5.22 (brs, 1H); 5.42 (dd, 1H); 5.60 (dd, 1H); 6.00 (d, 1H); 6.08 (d, 1H); 6.38 (d, 1H); 6.89 (d, 1H).

EXAMPLE 49

[5Z,7E,22E,25(E,E)]-(1S,3R,24R)-25-(1-Oxo-2,4-hexadienyl)-26,27-cyclo-9,10-secocholesta-5,7,10(19),22-tetraene-1,3,24-triol (118b)

5.94 ml of n-butyllithium (1.6 M in hexane) is added in drops to 1.46 ml of diisopropylamine in 67 ml of THF under nitrogen at 0° C. After 15 minutes, the reaction mixture is cooled to −78° C., and 540 mg of 7b (see 3) in 2.2 ml of THF is added in drops. After heating to 0° C., the reaction mixture is stirred into saturated ammonium chloride solution, extracted with ethyl acetate, the organic phase is dried on sodium sulfate and concentrated by evaporation. Chromatography on silica gel with ethyl acetate/hexane yields 65 mg of 118b as a colorless foam.

¹H-NMR (300 MHz, CDCl₃): δ=0.57 ppm (s, 3H); 0.97 (m, 2H); 1.05 (d, 3H); 1.20 (m, 2H); 1.88 (d, 3H); 3.50 (m, 1H); 4.10 (m, 1H); 4.23 (m, 1H); 4.43 (m, 1H); 5.00 (brs, 1H); 5.32 (brs, 1H); 5.42 (dd, 1H); 5.53 (dd, 1H); 5.92 (d, 1H); 6.00 (d, 1H); 6.18 (m, 1H); 6.38 (d, 1H); 7.30 (dd, 1H)

What is claimed is:

1. A vitamin D derivative with substituents at C-25 of general formula I

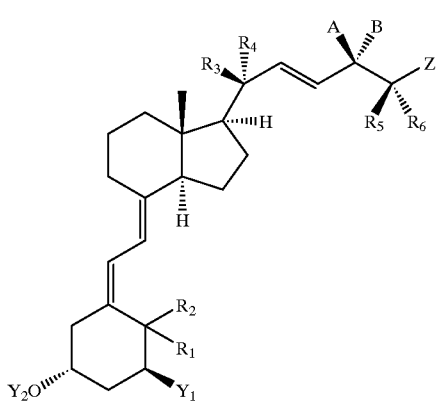

in which

- $Y_1$ means a hydrogen atom, a hydroxyl group, an alkanoyloxy group with 1 to 12 C atoms or an aroyloxy group,
- $Y_2$ means a hydrogen atom or an alkanoyl group with 1 to 12 C atoms or an aroyl group,
- $R_1$ and $R_2$ each mean a hydrogen atom or together an exocyclic methylene group,
- $R_3$ and $R_4$, independently of one another, mean a hydrogen atom, a chlorine or fluorine atom, an alkyl group with 1 to 4 carbon atoms, together a methylene group or together with quaternary carbon atom 20 a 3- to 7-membered, saturated or unsaturated carbocyclic ring,
- A and B together mean a keto group or A means a group OR' and B means a hydrogen atom or B means a group OR' and A means a hydrogen atom, whereby R' is a hydrogen atom or a straight-chain or branched-chain, saturated alkanoyl group with up to 9 carbon atoms or an aroyl group,
- $R_5$ and $R_6$ at the same time each mean a hydrogen atom, a chlorine or fluorine atom, a trifluoromethyl group, a straight-chain or branched-chain, saturated or unsaturated hydrocarbon radical with up to 4 carbon atoms or $R_5$ and $R_6$ together with carbon atom 25 mean a 3- to 7-membered, saturated or unsaturated carbocyclic ring and
- Z means a straight-chain or branched-chain, saturated or unsaturated hydrocarbon radical with up to 12 carbon atoms, which can also have a carbocyclic or heterocyclic structure or partial structure and at any positions can exhibit keto groups, hydroxy groups (in α- or β-position) that in turn can be etherified or esterified, amino groups, halogen atoms or carboxylic acid ester or amide units and is linked with carbon atom 25 by a carbonyl group, a hydroxymethylene group or an ethenediyl unit (E- or Z-geometry).

2. A vitamin D derivative according to claim 1, (5Z,7E,22E)-(1S,3R,24R)-25-(1-Oxopentyl)-26,27-cyclo-9,10-secocholesta-5,7,10(19),22-tetraene-1,3,24-triol (5Z,7E,22E)-(1S,3R,24S)-25-(1-oxopentyl)-26,27-cyclo-9,10-secocholesta-5,7,10(19),22-tetraene-1,3,24-triol (5Z,7E,22E)-(1S,3R,24R)-25-acetyl-26,27-cyclo-9,10-secocholesta-5,7,10(19),22-tetraene-1,3,24-triol (5Z,7E,22E)-(1S,3R,24S)-25-acetyl-26,27-cyclo-9,10-secocholesta-5,7,10(19),22-tetraene-1,3,24-triol (5Z,7E,22E)-(1S,3R,24R)-25-(1-oxopropyl)-26,27-cyclo-9,10-secocholesta-5,7,10(19),22-tetraene-1,3,24-triol (5Z,7E,22E)-(1S,3R,24S)-25-(1-oxopropyl)-26,27-cyclo-9,10-secocholesta-5,7,10(19),22-tetraene-1,3,24-triol (5Z,7E,22E)-(1S,3R,24R)-25-(1-oxobutyl)-26,27-cyclo-9,10-secocholesta-5,7,10(19),22-tetraene-1,3,24-triol (5Z,7E,22E)-(1S,3R,24S)-25-(1-oxobutyl)-26,27-cyclo-9,10-secocholesta-5,7,10(19),22-tetraene-1,3,24-triol (5Z,7E,22E)-(1S,3R,24R)-25-(1-oxohexyl)-26,27-cyclo-9,10-secocholesta-5,7,10(19),22-tetraene-1,3,24-triol (5Z,7E,22E)-(1S,3R,24S)-25-(1-oxohexyl)-26,27-cyclo-9,10-secocholesta-5,7,10(19),22-tetraene-1,3,24-triol (5Z,7E,22E)-(1S,3R,24R)-25-(1-oxoheptyl)-26,27-cyclo-9,10-secocholesta-5,7,10(19),22-tetraene-1,3,24-triol (5Z,7E,22E)-(1S,3R,24S)-25-(1-oxoheptyl)-26,27-cyclo-9,10-secocholesta-5,7,10(19),22-tetraene-1,3,24-triol (5Z,7E,22E)-(1S,3R,24R)-25-(1-oxooctyl)-26,27-cyclo-9,10-secocholesta-5,7,10(19),22-tetraene-1,3,24-triol (5Z,7E,22E)-(1S,3R,24S)-25-(1-oxooctyl)-26,27-cyclo-9,10-secocholesta-5,7,10(19),22-tetraene-1,3,24-triol (5Z,7E,22E)-(1S,3R,24R)-25-(1-oxononyl)-26,27-cyclo-9,10-secocholesta-5,7,10(19),22-tetraene-1,3,24-triol (5Z,7E,22E)-(1S,3R,24S)-25-(1-oxononyl)-26,27-cyclo-9,10-secocholesta-5,7,10(19),22-tetraene-1,3,24-triol (5Z,7E,22E)-(1S,3R,24R)-25-benzoyl-26,27-cyclo-9,10-secocholesta-5,7,10(19),22-tetraene-1,3,24-triol (5Z,7E,22E)-(1S,3R,24S)-25-benzoyl-26,27-cyclo-9,10-secocholesta-5,7,10(19),22-tetraene-1,3,24-triol (5Z,7E,22E)-(1S,3R,24R)-25-(2-furanylcarbonyl)-26,27-cyclo-9,10-secocholesta-5,7,10(19),22-tetraene-1,3,24-triol (5Z,7E,22E)-(1S,3R,24S)-25-(2-furanylcarbonyl)-26,27-cyclo-9,10-secocholesta-5,7,10(19),22-tetraene-1,3,24-triol (5Z,7E,22E)-(1S,3R,24R)-25-(2,2-dimethyl-1-oxopropyl)-26,27-cyclo-9,10-secocholesta-5,7,10(19),22-tetraene-1,3,24-triol (5Z,7E,22E)-(1S,3R,24S)-25-(2,2-dimethyl-1-oxopropyl)-26,27-cyclo-9,10-secocholesta-5,7,10(19),22-tetraene-1,3,24-triol (5Z,7E,22E)-(1S,3R,24R)-25-(2-pyridinylcarbonyl)-26,27-cyclo-9,10-secocholesta-5,7,10(19),22-tetraene-1,3,24-triol (5Z,7E,22E)-(1S,3R,24S)-25-(2-pyridinylcarbonyl)-26,27-cyclo-9,10-secocholesta-5,7,10(19),22-tetraene-1,3,24-triol

[5Z,7E,22E,25(E)]-(1S,3R,24R)-25-(1-oxo-2-hexenyl)-26,27-cyclo-9,10-secocholesta-5,7,10(19),22-tetraene-1,3,24-triol

[5Z,7E,22E,25(E)]-(1S,3R,24S)-25-(1-oxo-2-hexenyl)-26,27-cyclo-9,10-secocholesta-5,7,10(19),22-tetraene-1,3,24-triol (5Z,7E,22E)-(1S,3R,24R)-25-(1-oxo-2-hexinyl)-26,27-cyclo-9,10-secocholesta-5,7,10(19),22-tetraene-1,3,24-triol (5Z,7E,22E)-(1S,3R,24S)-25-(1-oxo-2-hexinyl)-26,27-cyclo-9,10-secocholesta-5,7,10(19),22-tetraene-1,3,24-triol (5Z,7E,22E)-(1S,3R,24R)-25-(cyclopropylcarbonyl)-26,27-cyclo-9,10-secocholesta-5,7,10(19),22-tetraene-1,3,24-triol (5Z,7E,22E)-(1S,3R,24S)-25-(cyclopropylcarbonyl)-26,27-cyclo-9,10-secocholesta-5,7,10(19),22-tetraene-1,3,24-triol

[5Z,7E,22E,25(E)]-(1S,3R,24R)-25-(3-ethoxy-3-oxo-1-propenyl)-26,27-cyclo-9,10-secocholesta-5,7,10(19),22-tetraene-1,3,24-triol

[5Z,7E,22E,25(E)]-(1S,3R,24S)-25-(3-ethoxy-3-oxo-1-propenyl)-26,27-cyclo-9,10-secocholesta-5,7,10(19),22-tetraene-1,3,24-triol

[5Z,7E,22E,25(E)]-(1S,3R,24R)-25-[3-(1,1-dimethylethoxy)-3-oxo-1-propenyl]-26,27-cyclo-9,10-secocholesta-5,7,10(19),22-tetraene-1,3,24-triol

[5Z,7E,22E,25(E)]-(1S,3R,24S)-25-[3-(1,1-dimethylethoxy)-3-oxo-1-propenyl]-26,27-cyclo-9,10-secocholesta-5,7,10(19),22-tetraene-1,3,24-triol

[5Z,7E,22E,25(E)]-(1S,3R,24R)-25-(3-propoxy-3-oxo-1-propenyl)-26,27-cyclo-9,10-secocholesta-5,7,10(19),22-tetraene-1,3,24-triol

[5Z,7E,22E,25(E)]-(1S,3R,24S)-25-(3-propoxy-3-oxo-1-propenyl)-26,27-cyclo-9,10-secocholesta-5,7,10(19),22-tetraene-1,3,24-triol

[5Z,7E,22E,25(E)]-(1S,3R,24R)-25-(3-butoxy-3-oxo-1-propenyl)-26,27-cyclo-9,10-secocholesta-5,7,10(19),22-tetraene-1,3,24-triol

[5Z,7E,22E,25(E)]-(1S,3R,24S)-25-(3-butoxy-3-oxo-1-propenyl)-26,27-cyclo-9,10-secocholesta-5,7,10(19),22-tetraene-1,3,24-triol (5Z,7E,22E)-[1S,3R,24S,25(S)]-25-(1-hydroxy-2,2,3,3,4,4,5,5,5-nonafluoropentyl)-26,27-cyclo-9,10-secocholesta-5,7,10(19),22-tetraene-1,3,24-triol (5Z,7E,22E)-[1S,3R,24S,25(R)]-25-(1-hydroxy-2,2,3,3,4,4,5,5,5-nonafluoropentyl)-26,27-cyclo-9,10-secocholesta-5,7,10(19),22-tetraene-1,3,24-triol (5Z,7E,22E)-[1S,3R,24R,25(S)]-25-(1-hydroxy-2,2,3,3,4,4,5,5,5-nonafluoropentyl)-26,27-cyclo-9,10-secocholesta-5,7,10(19),22-tetraene-1,3,24-triol (5Z,7E,22E)-[1S,3R,24R,25(R)]-25-(1-hydroxy-2,2,3,3,4,4,5,5,5-nonafluoropentyl)-26,27-cyclo-9,10-secocholesta-5,7,10(19),22-tetraene-1,3,24-triol (5Z,7E,22E)-[1S,3R,24S,25(S)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol (5Z,7E,22E)-[1S,3R,24S,25(R)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol (5Z,7E,22E)-[1S,3R,24R,25(S)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol (5Z,7E,22E)-[1S,3R,24R,25(R)]-25-(1-hydroxy-2,2,3,3,4,4,5,5,6,6,7,7,7-tridecafluoroheptyl)-26,27-cyclo-9,10-secocholesta-5,7,10(19),22-tetraene-1,3,24-triol (5Z,7E,22E)-(1S,3R,24R)-25-(trifluoroacetyl)-26,27-cyclo-9,10-secocholesta-5,7,10(19),22-tetraene-1,3,24-triol (5Z,7E,22E)-(1S,3R,24S)-25-(trifluoroacetyl)-26,27-cyclo-9,10-secocholesta-5,7,10(19),22-tetraene-1,3,24-triol (5Z,7E,22E)-(1S,3R,24R)-25-(perfluoroethylcarbonyl)-26,27-cyclo-9,10-secocholesta-5,7,10(19),22-tetraene-1,3,24-triol (5Z,7E,22E)-(1S,3R,24S)-25-(perfluoroethylcarbonyl)-26,27-cyclo-9,10-secocholesta-5,7,10(19),22-tetraene-1,3,24-triol (5Z,7E,22E)-(1S,3R,24R)-25-(perfluoropropylcarbonyl)-26,27-cyclo-9,10-secocholesta-5,7,10(19),22-tetraene-1,3,24-triol (5Z,7E,22E)-(1S,3R,24S)-25-(perfluoropropylcarbonyl)-26,27-cyclo-9,10-secocholesta-5,7,10(19),22-tetraene-1,3,24-triol (5Z,7E,22E)-(1S,3R,24R)-25-(perfluorobutylcarbonyl)-26,27-cyclo-9,10-secocholesta-5,7,10(19),22-tetraene-1,3,24-triol (5Z,7E,22E)-(1S,3R,24S)-25-(perfluorobutylcarbonyl)-26,27-cyclo-9,10-secocholesta-5,7,10(19),22-tetraene-1,3,24-triol (5Z,7E,22E)-(1S,3R,24R)-25-(perfluoropentylcarbonyl)-26,27-cyclo-9,10-secocholesta-5,7,10(19),22-tetraene-1,3,24-triol (5Z,7E,22E)-(1S,3R,24S)-25-(perfluoropentylcarbonyl)-26,27-cyclo-9,10-secocholesta-5,7,10(19),22-tetraene-1,3,24-triol (5Z,7E,22E)-(1S,3R,24R)-25-(perfluorohexylcarbonyl)-26,27-cyclo-9,10-secocholesta-5,7,10(19),22-tetraene-1,3,24-triol (5Z,7E,22E)-(1S,3R,24S)-25-(perfluorohexylcarbonyl)-26,27-cyclo-9,10-secocholesta-5,7,10(19),22-tetraene-1,3,24-triol (5Z,7E,22E)-(1S,3R,24R)-25-acetyl-20-methyl-26,27-cyclo-9,10-secocholesta-5,7,10(19),22-tetraene-1,3,24-triol (5Z,7E,22E)-(1S,3R,24S)-25-acetyl-20-methyl-26,27-cyclo-9,10-secocholesta-5,7,10(19),22-tetraene-1,3,24-triol (5Z,7E,22E)-(1S,3R,24R)-20-methyl-25-(1-oxopropyl)-26,27-cyclo-9,10-secocholesta-5,7,10(19),22-tetraene-1,3,24-triol (5Z,7E,22E)-(1S,3R,24S)-20-methyl-25-(1-oxopropyl)-26,27-cyclo-9,10-secocholesta-5,7,10(19),22-tetraene-1,3,24-triol (5Z,7E,22E)-(1S,3R,24R)-20-methyl-25-(1-oxobutyl)-26,27-cyclo-9,10-secocholesta-5,7,10(19),22-tetraene-1,3,24-triol (5Z,7E,22E)-(1S,3R,24S)-20-methyl-25-(1-oxobutyl)-26,27-cyclo-9,10-secocholesta-5,7,10(19),22-tetraene-1,3,24-triol (5Z,7E,22E)-(1S,3R,24R)-20-methyl-25-(1-oxopentyl)-26,27-cyclo-9,10-secocholesta-5,7,10(19),22-tetraene-1,3,24-triol (5Z,7E,22E)-(1S,3R,24S)-20-methyl-25-(1-oxopentyl)-26,27-cyclo-9,10-secocholesta-5,7,10(19),22-tetraene-1,3,24-triol (5Z,7E,22E)-(1S,3R,24R)-20-methyl-25-(1-oxohexyl)-26,27cyclo-9,10-secocholesta-5,7,10(19),22-tetraene-1,3,24-triol (5Z,7E,22E)-(1S,3R,24S)-20-methyl-25-(1-oxohexyl)-26,27-cyclo-9,10-secocholesta-5,7,10(19),22-tetraene-1,3,24-triol (5Z,7E,22E)-(1S,3R,24R)-20-methyl-25-(1-oxoheptyl)-26,27-cyclo-9,10-secocholesta-5,7,10(19),22-tetraene-1,3,24-triol (5Z,7E,22E)-(1S,3R,24S)-20-methyl-25-(1-oxoheptyl)-26,27-cyclo-9,10-secocholesta-5,7,10(19),22-tetraene-1,3,24-triol (5Z,7E,22E)-(1S,3R,24R)-20-methyl-25-(1-oxooctyl)-26,27-cyclo-9,10-secocholesta-5,7,10(19),22-tetraene-1,3,24-triol (5Z,7E,22E)-(1S,3R,24S)-20-methyl-25-(1-oxooctyl)-26,27-cyclo-9,10-secocholesta-5,7,10(19),22-tetraene-1,3,24-triol (5Z,7E,22E)-(1S,3R,24R)-20-methyl-25-(1-oxononyl)-26,27-cyclo-9,10-secocholesta-5,7,10(19),22-tetraene-1,3,24-triol (5Z,7E,22E)-(1S,3R,24S)-20-methyl-25-(1-oxononyl)-26,27-cyclo-9,10-secocholesta-5,7,10(19),22-tetraene-1,3,24-triol (7E,22E)-(1R,3R,24R)-25-acetyl-26,27-cyclo-19-nor-9,10-secocholesta-5,7,22-triene-1,3,24-triol (7E,22E)-(1R,3R,24S)-25-acetyl-26,27-cyclo-19-nor-9,10-secocholesta-5,7,22-triene-1,3,24-triol
(7E,22E)-(1R,3R,24R)-25-(1-oxopropyl)-26,27-cyclo-19-nor-9,10-secocholesta-5,7,22-triene-1,3,24-triol
(7E,22E)-(1R,3R,24S)-25-(1-oxopropyl)-26,27-cyclo-19-nor-9,10-secocholesta-5,7,22-triene-1,3,24-triol
(7E,22E)-(1R,3R,24R)-25-(1-oxobutyl)-26,27-cyclo-19-nor-9,10-secocholesta-5,7,22-triene-1,3,24-triol
(7E,22E)-(1R,3R,24S)-25-(1-oxobutyl)-26,27-cyclo-19-nor-9,10-secocholesta-5,7,22-triene-1,3,24-triol
(7E,22E)-(1R,3R,24R)-25-(1-oxopentyl)-26,27-cyclo-19-nor-9,10-secocholesta-5,7,22-triene-1,3,24-triol
(7E,22E)-(1R,3R,24S)-25-(1-oxopentyl)-26,27-cyclo-19-nor-9,10-secocholesta-5,7,22-triene-1,3,24-triol
(7E,22E)-(1R,3R,24R)-25-(1-oxohexyl)-26,27-cyclo-19-nor-9,10-secocholesta-5,7,22-triene-1,3,24-triol
(7E,22E)-(1R,3R,24S)-25-(1-oxohexyl)-26,27-cyclo-19-nor-9,10-secocholesta-5,7,22-triene-1,3,24-triol
(7E,22E)-(1R,3R,24R)-25-(1-oxoheptyl)-26,27-cyclo-19-nor-9,10-secocholesta-5,7,22-triene-1,3,24-triol
(7E,22E)-(1R,3R,24S)-25-(1-oxoheptyl)-26,27-cyclo-19-nor-9,10-secocholesta-5,7,22-triene-1,3,24-triol
(7E,22E)-(1R,3R,24R)-25-(1-oxooctyl)-26,27-cyclo-19-nor-9,10-secocholesta-5,7,22-triene-1,3,24-triol
(7E,22E)-(1R,3R,24S)-25-(1-oxooctyl)-26,27-cyclo-19-nor-9,10-secocholesta-5,7,22-triene-1,3,24-triol
(7E,22E)-(1R,3R,24R)-25-(1-oxononyl)-26,27-cyclo-19-nor-9,10-secocholesta-5,7,22-triene-1,3,24-triol
(7E,22E)-(1R,3R,24S)-25-(1-oxononyl)-26,27-cyclo-19-nor-9,10-secocholesta-5,7,22-triene-1,3,24-triol
(7E,22E)-(1R,3R,24R)-25-acetyl-20-methyl-26,27-cyclo-19-nor-9,10-secocholesta-5,7,22-triene-1,3,24-triol
(7E,22E)-(1R,3R,24S)-25-acetyl-20-methyl-26,27-cyclo-19-nor-9,10-secocholesta-5,7,22-triene-1,3,24-triol
(7E,22E)-(1R,3R,24R)-20-methyl-25-(1-oxopropyl)-26,27-cyclo-19-nor-9,10-secocholesta-5,7,22-triene-1,3,24-triol
(7E,22E)-(1R,3R,24S)-20-methyl-25-(1-oxopropyl)-26,27-cyclo-19-nor-9,10-secocholesta-5,7,22-triene-1,3,24-triol
(7E,22E)-(1R,3R,24R)-20-methyl-25-(1-oxobutyl)-26,27-cyclo-19-nor-9,10-secocholesta-5,7,22-triene-1,3,24-triol
(7E,22E)-(1R,3R,24S)-20-methyl-25-(1-oxobutyl)-26,27-cyclo-19-nor-9,10-secocholesta-5,7,22-triene-1,3,24-triol
(7E,22E)-(1R,3R,24R)-20-methyl-25-(1-oxopentyl)-26,27-cyclo-19-nor-9,10-secocholesta-5,7,22-triene-1,3,24-triol
(7E,22E)-(1R,3R,24S)-20-methyl-25-(1-oxopentyl)-26,27-cyclo-19-nor-9,10-secocholesta-5,7,22-triene-1,3,24-triol
(7E,22E)-(1R,3R,24R)-20-methyl-25-(1-oxohexyl)-26,27-cyclo-19-nor-9,10-secocholesta-5,7,22-triene-1,3,24-triol
(7E,22E)-(1R,3R,24S)-20-methyl-25-(1-oxohexyl)-26,27-cyclo-19-nor-9,10-secocholesta-5,7,22-triene-1,3,24-triol
(7E,22E)-(1R,3R,24R)-20-methyl-25-(1-oxoheptyl)-26,27-cyclo-19-nor-9,10-secocholesta-5,7,22-triene-1,3,24-triol
(7E,22E)-(1R,3R,24S)-20-methyl-25-(1-oxoheptyl)-26,27-cyclo-19-nor-9,10-secocholesta-5,7,22-triene-1,3,24-triol
(7E,22E)-(1R,3R,24R)-20-methyl-25-(1-oxooctyl)-26,27-cyclo-19-nor-9,10-secocholesta-5,7,22-triene-1,3,24-triol
(7E,22E)-(1R,3R,24S)-20-methyl-25-(1-oxooctyl)-26,27-cyclo-19-nor-9,10-secocholesta-5,7,22-triene-1,3,24-triol
(7E,22E)-(1R,3R,24R)-20-methyl-25-(1-oxononyl)-26,27-cyclo-19-nor-9,10-secocholesta-5,7,22-triene-1,3,24-triol
(7E,22E)-(1R,3R,24S)-20-methyl-25-(1-oxononyl)-26,27-cyclo-19-nor-9,10-secocholesta-5,7,22-triene-1,3,24-triol
(5Z,7E,22E)-[1S,3R,25(R)]-1,3-dihydroxy-25-(1-hydroxy-2,2,3,3,4,4,5,5,5-nonafluoropentyl)-26,27-cyclo-9,10-secocholesta-5,7,10(19),22-tetraen-24-one
(5Z,7E,22E)-[1S,3R,25(S)]-1,3-dihydroxy-25-(1-hydroxy-2,2,3,3,4,4,5,5,5-nonafluoropentyl)-26,27-cyclo-9,10-secocholesta-5,7,10(19),22-tetraen-24-one
(5Z,7E,22E)-[1S,3R,25(R)]-1,3-dihydroxy-25-(1-hydroxy-2,2,3,3,4,4,5,5,6,6,7,7,7-tridecafluoroheptyl)-26,27-cyclo-9,10-secocholesta-5,7,10(19),22-tetraen-24-one
(5Z,7E,22E)-[1S,3R,25(S)]-1,3-dihydroxy-25-(1-hydroxy-2,2,3,3,4,4,5,5,6,6,7,7,7-tridecafluoroheptyl)-26,27-cyclo-9,10-secocholesta-5,7,10(19),22-tetraen-24-one
(5Z,7E,22E)-(3S,24R)-25-acetyl-26,27-cyclo-9,10-secocholesta-5,7,10(19),22-tetraene-3,24-diol
(5Z,7E,22E)-(3S,24S)-25-acetyl-26,27-cyclo-9,10-secocholesta-5,7,10(19),22-tetraene-3,24-diol
(5Z,7E,22E)-(3S,24R)-25-(1-oxopropyl)-26,27-cyclo-9,10-secocholesta-5,7,10(19),22-tetraene-3,24-diol
(5Z,7E,22E)-(3S,24S)-25-(1-oxopropyl)-26,27-cyclo-9,10-secocholesta-5,7,10(19),22-tetraene-3,24-diol
(5Z,7E,22E)-(3S,24R)-25-(1-oxobutyl)-26,27-cyclo-9,10-secocholesta-5,7,10(19),22-tetraene-3,24-diol
(5Z,7E,22E)-(3S,24S)-25-(1-oxobutyl)-26,27-cyclo-9,10-secocholesta-5,7,10(19),22-tetraene-3,24-diol
(5Z,7E,22E)-(3S,24R)-25-(1-oxopentyl)-26,27-cyclo-9,10-secocholesta-5,7,10(19),22-tetraene-3,24-diol
(5Z,7E,22E)-(3S,24S)-25-(1-oxopentyl)-26,27-cyclo-9,10-secocholesta-5,7,10(19),22-tetraene-3,24-diol
(5Z,7E,22E)-(3S,24R)-25-(1-oxohexyl)-26,27-cyclo-9,10-secocholesta-5,7,10(19),22-tetraene-3,24-diol
(5Z,7E,22E)-(3S,24S)-25-(1-oxohexyl)-26,27-cyclo-9,10-secocholesta-5,7,10(19),22-tetraene-3,24-diol
(5Z,7E,22E)-(3S,24R)-25-(1-oxoheptyl)-26,27-cyclo-9,10-secocholesta-5,7,10(19),22-tetraene-3,24-diol
(5Z,7E,22E)-(3S,24S)-25-(1-oxoheptyl)-26,27-cyclo-9,10-secocholesta-5,7,10(19),22-tetraene-3,24-diol
(5Z,7E,22E)-(3S,24R)-25-(1-oxooctyl)-26,27-cyclo-9,10-secocholesta-5,7,10(19),22-tetraene-3,24-diol
(5Z,7E,22E)-(3S,24S)-25-(1-oxooctyl)-26,27-cyclo-9,10-secocholesta-5,7,10(19),22-tetraene-3,24-diol
(5Z,7E,22E)-(3S,24R)-25-(1-oxononyl)-26,27-cyclo-9,10-secocholesta-5,7,10(19),22-tetraene-3,24-diol
(5Z,7E,22E)-(3S,24S)-25-(1-oxononyl)-26,27-cyclo-9,10-secocholesta-5,7,10(19),22-tetraene-3,24-diol
[5Z,7E,22E,25(E)]-(1S,3R,24R)-25-[3-(1,1-dimethylethoxy)-3-oxo-1-propenyl]-24-methoxy-26,27-cyclo-9,10-secocholesta-5,7,10(19),22-tetraene-1,3diol
[5Z,7E,22E,25(E)]-(1S,3R,24S)-25-[3-(1,1-dimethylethoxy)-3-oxo-1-propenyl]-24-methoxy-26,27-cyclo-9,10-secocholesta-5,7,10(19),22-tetraene-1,3diol
(5Z,7E,22E)-(1S,3R,24R)-25-hydroxymethyl-26,27-cyclo-9,10-secocholesta-5,7,10(19),22-tetraene-1,3,24-triol
(5Z,7E,22E)-(1S,3R,24S)-25-hydroxymethyl-26,27-cyclo-9,10-secocholesta-5,7,10(19),22-tetraene-1,3,24-triol
[5Z,7E,22E,25(E)]-(1S,3R,24R)-25-(3-oxo-1-heptenyl)-26,27-cyclo-9,10-secocholesta-5,7,10(19),22-tetraene-1,3,24-triol
[5Z,7E,22E,25(E)]-(1S,3R,24S)-25-(3-oxo-1-heptenyl)-26,27-cyclo-9,10-secocholesta-5,7,10(19),22-tetraene-1,3,24-triol
[5Z,7E,22E,25(E,E)]-(1S,3R,24R)-25-(1-oxo-2,4-hexadienyl)-26,27-cyclo-9,10-secocholesta-5,7,10(19),22-tetraene-1,3,24-triol
[5Z,7E,22E,25(E,E)]-(1S,3R,24S)-25-(1-oxo-2,4-hexadienyl)-26,27-cyclo-9,10-secocholesta-5,7,10(19),22-tetraene-1,3,24-triol.

3. A process for preparing a vitamin D derivative of general formula I according to claim 1 or 2, in which a compound of general formula II,

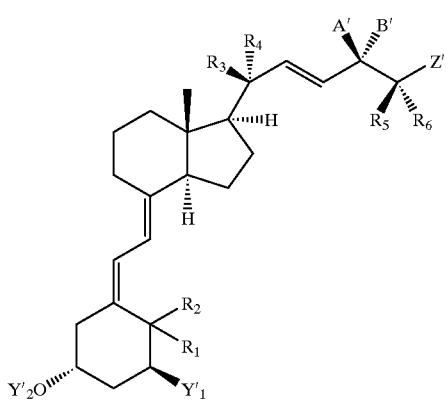

II in which

Y'$_1$ means a hydrogen atom or a protected hydroxy group and Y'$_2$ means a hydroxy protective group, A' and B' together mean a keto group or one of the two substituents means an optionally protected hydroxy group and the other a hydrogen atom, Z' can mean Z or optionally exhibit protective group-carrying substituents, is reacted by simultaneous or successive cleavage of the hydroxy protective groups and optionally by partial, successive or complete esterification of the free hydroxy groups.

4. A method of treating hyperproliferative disease of the skin, tumor disease, cancer, auto-immune disease transplantation rejection disease or atropic skin or wound healing secondary hyperparathyroidism, renal osteodystrophia senile and postmenopausal osteoporosis, and degenerative disease of the peripheral and central nervous system comprising administering an effective amount of a compound according to claim 1.

5. A method of treating hypercalcemia, granulomatous disease, paraneoplastic hypercalcemia in hyperparathyroidism, hirsutism, arteriosclerosis, inflammatory diseases, and birth control, comprising administering an effective amount of a compound according to claim 1.

6. A compound of general formula XII

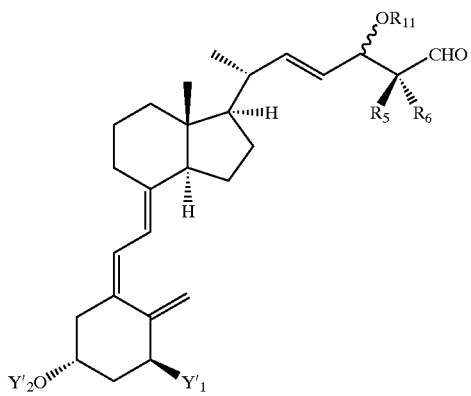

XII wherein

R$_5$ and R$_6$ at the same time each mean a hydrogen atom, a chlorine or fluorine atom, a trifluoromethyl group, a straight-chain or branched-chain, saturated or unsaturated hydrocarbon radical with up to 4 carbon atoms or R$_5$ or R$_6$ together with carbon atom 25 mean a 3- to 7-membered, saturated or unsaturated carbocyclic ring;

Y'$_1$ means a hydrogen atom or a protected hydroxy group and Y'$_2$ means a hydroxy protective group;

R$_{11}$ means an acid-labile protective group of Y'$_1$ or Y'$_2$ or a tetrahydropyranyl, tetrahydrofuranyl, ethoxyethylene, methoxymethyl or methoxyethoxymethyl group.

* * * * *